US006380400B1

(12) United States Patent
Fedij et al.

(10) Patent No.: US 6,380,400 B1
(45) Date of Patent: Apr. 30, 2002

(54) METHODS OF MAKING DIHYDROPYRONE HIV PROTEASE INHIBITORS

(76) Inventors: Victor Fedij, 354 Marquette Ave., Holland, MI (US) 49424; Christopher Andrew Gajda, 2684 Bellwood, Ann Arbor, MI (US) 48104; Brian Keith Huckabee, 12872 Thistlewood La., Holland, MI (US) 49424; Brian Stuart Moon, 16731 Ashley La., Holland, MI (US) 49424; Kenneth Thomas Porter, 14073 Deercove Dr., Holland, MI (US) 49424; Denis Martin Sobieray, 2178 S. Bristol, Holland, MI (US) 48424; Timothy Lee Stuk, 390 Erin Isle Dr., Holland, MI (US) 49424; Bradley Dean Tait, 8431 Congress Dr., Canton, MI (US) 48187; James Norton Wemple, 14211 Deercove Dr., Holland, MI (US) 49424

( * ) Notice: Subject to any disclaimer, the term of this patent is extended or adjusted under 35 U.S.C. 154(b) by 0 days.

(21) Appl. No.: 09/674,381
(22) PCT Filed: Jan. 7, 1999
(86) PCT No.: PCT/US99/15118
 § 371 Date: Oct. 31, 2000
 § 102(e) Date: Oct. 31, 2000
(87) PCT Pub. No.: WO00/15625
 PCT Pub. Date: Mar. 23, 2000

Related U.S. Application Data
(60) Provisional application No. 60/099,944, filed on Sep. 11, 1998.

(51) Int. Cl.$^7$ .................. C07D 309/32; C07C 333/04; C07C 381/04
(52) U.S. Cl. .............. 549/292; 558/234; 558/241; 560/308
(58) Field of Search ............... 558/234, 241; 560/308; 549/292

(56) References Cited

U.S. PATENT DOCUMENTS
5,789,440 A  8/1998  Ellsworth et al. ........... 514/460
5,834,506 A  11/1998  Boyer, Jr. et al. ........... 514/460

FOREIGN PATENT DOCUMENTS
WO  9819997  5/1998

OTHER PUBLICATIONS
PCT International Search Report, PCT/US99/15118 (1999).
Gordon et al., "The synthesis of an electronically asymmetric substituted poly(arylenevinylene); poly {2–(2'–ethylhexyloxy)–5–[(E)–4"–nitrostyryl]–1,4–phenylenevinylene}", J. Mater. Chem., vol. 6, No. 8, (1996,) pp. 1253–1258.
Shokat et al., "Mechanistic Studies of an Antibody–Catalyzed Elimination Reaction", J. Am. Chem. Soc., vol. 116, No. 6, (1994) pp. 2261–2270.
Database WPI, Section Ch, Week 199345, Derwent Publications Ltd., London, BG; Class B05, AN 1993–354003, XP–002126738 (1993).
Chemical Abstracts, vol. 77, No. 13, (1972) abstract No. 88679b, Kaehler et al.
Chatterjee et al., "Xanthene derived potent nonpeptidic inhibitors of recombinant human calpain I", Bioorganic & Medicinal Chemistry Letters, vol. 6, No. 13, (1996) pp. 1619–1622.
Huang et al., "An Efficient and Stereoselective Synthesis of (E)–α–Enones via Arsonium Salts. Preparation of Key Intermediates for the Synthesis of Brassinosteroid and Prostaglandin", Synthesis, DE, Georg Thieme Verlag, Stuttgart, No. 12, (1988), pp. 975–977.
Database Beilstein Commander, Beilstein Institut, Citation No. 5841203, Barker et al., XP–002136226 (1983).
Database Beilstein Commander, Beilstein Institut, Citation No. 1971616, Baeyer et al., XP–002136227 (1883).
Emmer, "Synthesis of (2RS, E)–3–Ethylidene–azetidine–2–carboxylic Acid (rac. Polyoximic Acid)", Tetrahedron, vol. 48, No. 35, (1992,) pp. 7165–7172.
Fors et al., "A Convergent, Scalable Synthesis of HIV Protease Inhibitor PNU–140690", J. Org. Chem., vol. 63, (1998), pp. 7348–7356.
Dillard et al., "Indole Inhibitors of Human Nonpancreatic Secretory Phospholipase A$^2$. I. Indole–3–acetamides", J. Med. Chem., vol. 39, No. 26, (1996) pp. 5119–5136.
Vara Prasad et al., "Nonpeptidic HIV protease inhibitors: 6–alkyl–5, 6–dihydropyran–2–ones possessing achiral 3–(4–amino/carboxamide–2–t–butyl, 5–methylphenyl thio) moiety: antiviral activities and pharmacokinetic properties", Bioorganic & Medicinal Chemistry Letters, vol. 9, No. 11, (1999), pp. 1481–1486.
Morimura et al., "Vilsmeier Reaction of Phenols. I. Synthesis of Aryl Formates", Bull. Chem. So. Jpn., vol. 50, No. 8, (1977), pp. 2189–2190.
Gross et al., "Neue Verfahren zur Darstellung von Phenolaldehyden", Chem. Ber., vol. 96, (1963) pp. 308–313.
Meier et al., "[abc]–Annealated [18]Annulenes", J. Org. Chem., vol. 57, No. 25, (1992) pp. 6847–6852.
Grayson and Tuite, "Knoevenagel Reactions with β–Oxo Acids. Regiospecific Enol Equivalents for Syntheses of α,β–Unsaturated Ketones and of Some β–Ketols", J. Chem. Soc. Perkin Trans. I, (1986), pp. 2137–2142.
Becalski et al., "Catalytic Asymmetric Hydrogenation of Imines. Use of Rhodium(I)Phosphine Complexes and Characterization of Rhodium(I)/Imine Complexes", Inorg. Chem., vol. 30, No. 26 (1991), pp. 5002–5008.
Brooks et al., "C–Acylation under Virtually Neutral Conditions", Angew. Chem. Int. Ed. Engl., vol. 18, No. 1, (1979), pp. 72–74.

Primary Examiner—Bernard Dentz

(57) ABSTRACT

The present invention relates to methods of making dihydropyrone HIV inhibitors.

18 Claims, No Drawings

METHODS OF MAKING DIHYDROPYRONE HIV PROTEASE INHIBITORS

This application is a 371 of PCT/US99/15118 filed Jan. 7, 1999, which claims benefit of Provisional Application No. 60/099,944 filed Sep. 11, 1998.

FIELD OF THE INVENTION

The present invention relates to methods of making dihydropyrone HIV protease inhibitors.

BACKGROUND OF THE INVENTION

Despite efforts to discover effective treatments or a cure, human immuno-deficiency virus (HIV) infection and the disease acquired immunodeficiency syndrome (AIDS) continue to haunt modem society. One way of combating HIV infection and AIDS has been to administer to an affected patient a compound that inhibits the viral enzyme HIV protease, which is required by the virus to reproduce. Some compounds that inhibit HIV protease are currently being marketed to treat HIV infection and AIDS and have been shown to be most effective when used in combination with other compounds that can be used to treat HIV infection and AIDS. The dihydropyrones represent a new chemical class of HIV protease inhibitors. The present invention provides a commercially viable method for making dihydropyrone HIV protease inhibitors. In particular, the present invention relates to the synthesis of (S)-6-[2-(4-Aminophenyl)-ethyl]-3-(2-tert-butyl-4-hydroxymethyl-5-methylphenylsulfanyl)-4-hydroxy-6-isopropyl-5,6-dihydro-pyran-2-one; (S)-3-(2-tert-Butyl-4-hydroxymethyl-5-methyl-phenylsulfanyl)-4-hydroxy-6-[2-(4-hydroxy-phenyl)-ethyl]-6-isopropyl-5,6-dihydro-pyran-2-one; (S)-3-(4-Amino-2-tert-butyl-5-methyl-phenylsulfanyl)-4-hydroxy-6-[2-(4-hydroxy-phenyl)-ethyl]-6-isopropyl-5,6-dihydro-pyran-2-one; and (S)-3-(2-tert-Butyl-4-hydroxymethyl-5-methyl-phenylsulfanyl)-6-cyclopentyl-4-hydroxy-6-[2-(3-hydroxy-phenyl)-ethyl]-5,6-dihydro-pyran-2-one. See, U.S. Pat. No. 5,789,440, U.S. patent application Ser. No. 08/885,743 and U.S. patent application titled "HIV Protease Inhibitors" filed on the same day as the present application listing Boyer, Fred et al. as inventors, which applications and patents are hereby incorporated by reference.

SUMMARY OF THE INVENTION

The present invention provides the compounds dimethylthiocarbamic acid O-(2-tert-butyl-4-formyl-5-methylphenyl) ester;

Dimethylthiocarbamic acid S-(2-tert-butyl-4-formyl-5-methylphenyl) ester;

Dimethylthiocarbamic acid S-(2-tert-butyl-4-hydroxymethyl-5-methylphenyl) ester;

(+/−)-1-Hydroxy-4-methyl-1-(4-nitrophenyl)pentan-3-one;

(+/−)-1-Acetoxy-4-methyl-1-(4-nitrophenyl)pentan-3-one or [Acetic acid 4-methyl-1-(4-nitro-phenyl)-3-oxo-pentyl ester].

1-(4-N-A acetylaminophenyl)-4-methylpentan-3-one or [N-[4-(4-methyl-3-oxo-pentyl)-phenyl]-acetamide].

(+/−)-3-[2-(4-N-Acetylaminophenyl)ethyl]-3-hydroxy-4-methylpentanoic acid or [3-[2-(4-acetylamino-phenyl)-ethyl]-3-hydroxy-4-methyl-pentanoic acid].

(+/−)-3-Hydroxy-3-isopropyl-5-(4-nitrophenyl)-4-pentenoic acid benzyl ester or [3-hydroxy-3-isopropyl-5-(4-nitro-phenyl)-pent-4-enoic acid benzyl ester];

(+/−)-3-Hydroxy-3-isopropyl-5-(4-nitrophenyl)-4-pentenoic acid benzyl ester;

(+/−)-3-[2-(4-Aminophenyl)ethyl]-3-hydroxy-4-methylpentanoic acid;

(S)-3-[2-(4-Acetylaminophenyl)ethyl]-3-hydroxy-4-methylpentanoic acid;

(S)-3-[2-(4-Acetylaminophenyl)ethyl]-3-hydroxy-4-methylpentanoic acid (S)-N-benzyl-α-methylbenzylamine salt;

(S)-6-[2-(4-Acetylaminophenyl)ethyl]-4-hydroxy-6-isopropyl-5,6-dihydropyran-2-one;

(S)-5-[2-(4-Acetylaminophenyl)ethyl]-5-hydroxy-6-methyl-3-oxo-heptanoic acid ethyl ester;

(S)-N-(4-{2-[5-(2-tert-Butyl-4-hydroxymethyl-5-methylphenylsulfanyl)-4-hydroxy-2-isopropyl-6-oxo-3,6-dihydro-2H-pyran-2-yl]ethyl}phenyl)acetamide;

N-(5-tert-Butyl-2-methyl-4-thiocyanatophenyl)carbamic acid tert-butyl ester; and Toluene-4-thiosulfonic acid S-(4-tert-butoxycarbonylamino-2-tert-butyl-5-methylphenyl) ester.

The present invention provides a method of making compounds of Formula I

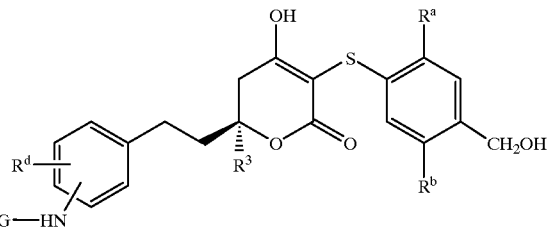

wherein $R^a$ and $R^b$ are independently $C_1$–$C_6$ alkyl;

$R^d$ is hydrogen, $C_1$–$C_6$ alkyl, or halogen;

$R^3$ is $C_2$–$C_8$ cycloalkyl or $C_1$–$C_6$ alkyl; and

PG is a protecting group selected from acetyl, formyl, propionyl, benzoyl, methyl carbamoyl, ethyl carbamoyl, benzyl carbamoyl, or trifluoroacetyl, or isobutyl carbamoyl, the method comprising the step of reacting

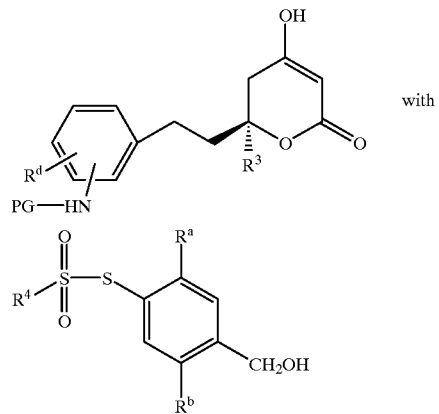

wherein $R^4$ is tolyl, phenyl, or methyl, in the presence of a tertiary amine base to give

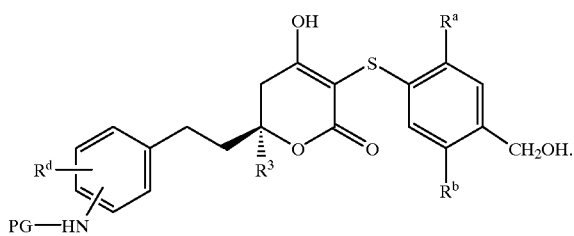

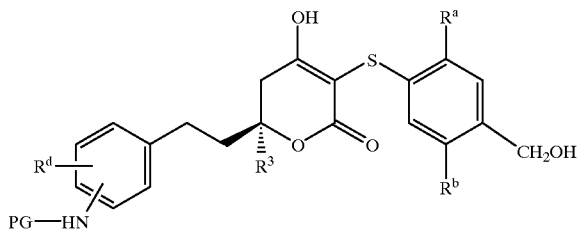

is further reacted with a base to form

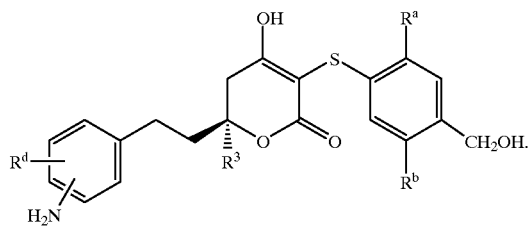

In another preferred embodiment, the reaction in the presence of a tertiary amine base is carried out in a low boiling point, polar, aprotic solvent.

In another preferred embodiment, the reaction in the presence of a tertiary amine base is carried out in acetonitrile or tetrahydrofuran.

In another preferred embodiment, the base is sodium hydroxide, potassium hydroxide, aqueous ammonia, or sodium methoxide.

In another preferred embodiment, the tertiary amine base is triethylamine.

In a more preferred embodiment, $R^3$ is

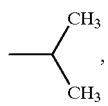, $R^a$ is

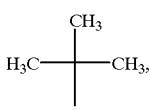, $R^b$ is —$CH_3$, and $R^d$ is hydrogen.

In another more preferred embodiment, the tertiary amine base is triethylamine, and the solvent is acetonitrile.

Also provided is a method of making

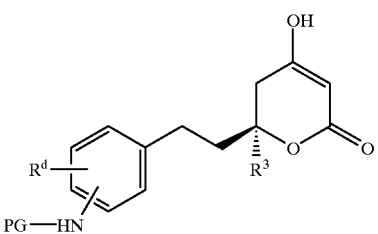

wherein $R^3$ is $C_2$–$C_8$ cycloalkyl or $C_1$–$C_6$ alkyl;

$R^d$ is hydrogen, $C_1$–$C_6$ alkyl, or halogen; and

PG is a protecting group selected from acetyl, formyl, propionyl, benzoyl, methyl carbamoyl, ethyl carbamoyl, benzyl carbamoyl, trifluoroacetyl, or isobutyl carbamoyl, the method comprising the steps of:

a. reacting

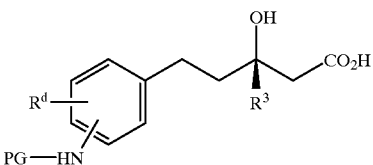

with carbonyl diimidazole to form

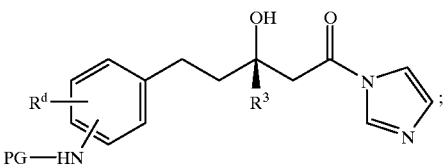;

b. reacting the

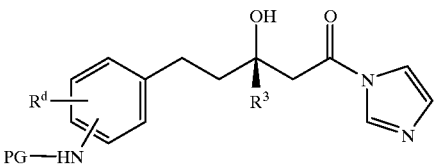

with a compound of the formula

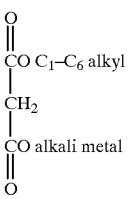

and MgCl$_2$, to form

[Chemical structure: phenyl ring with R$^d$ and PG—HN substituents, connected via ethyl chain to C(OH)(R$^3$) with chain —CH$_2$—C(O)—CH$_2$—C(O)—C$_1$–C$_6$ alkyl]

c. reacting the

[Chemical structure: same as above with C$_1$–C$_6$ alkyl]

with a base to form

[Chemical structure: dihydropyranone with phenyl-ethyl substituent bearing R$^d$ and PG—HN, and R$^3$ at ring carbon]

In a preferred embodiment, the base is NaOH or KOH.
In a preferred embodiment, $$R^3 \text{ is } -CH(CH_3)_2 \text{ or } -\text{cyclopentyl},$$

$$\begin{array}{c}\text{O}\\\|\\\text{CO C}_1\text{–C}_6 \text{ alkyl}\\|\\\text{CH}_2\\|\\\text{CO alkali metal}\\\|\\\text{O}\end{array}$$

is $$\begin{array}{c}\text{O}\\\|\\\text{C—OCH}_2\text{CH}_3,\\|\\\text{CH}_2\\|\\\text{CO}^{\ominus}\text{K}^{\oplus}\\\|\\\text{O}\end{array}$$

and R$^d$ is hydrogen.
Also provided is a method of resolving

[Chemical structure: phenyl-ethyl-C(OH)(R$^3$)-CH$_2$-CO$_2$H with R$^d$ and PG—HN on phenyl] from -continued

[Chemical structure: same (+/-)]

wherein
R$^3$ is C$_2$–C$_8$ cycloalkyl or C$_1$–C$_6$ alkyl;
R$^d$ is hydrogen, halogen, or C$_1$–C$_6$ alkyl; and
PG is a protecting group selected from acetyl, formyl, propionyl, benzoyl, methyl carbamoyl, ethyl carbamoyl, benzyl carbamoyl, trifluoroacetyl, or isobutyl carbamoyl,
the method comprising the steps of:
a. treating

[Chemical structure: (+/-)]

with (S)-N-benzyl-α-methyl benzyl amine;
b. allowing crystals to form;
c. collecting the crystals; and
d. isolating

[Chemical structure with defined stereocenter]

In a preferred embodiment, $$R^3 \text{ is } -\text{cyclopentyl or } -CH(CH_3)_2.$$

Also provided is a method of making

[Chemical structure: (+/-)]

wherein
R$^3$ is C$_2$–C$_8$ cycloalkyl or C$_1$–C$_6$ alkyl;
R$^d$ is hydrogen, halogen, or C$_1$–C$_6$ alkyl; and
PG is a protecting group selected from acetyl, formyl, propionyl, benzyl, methyl carbamoyl, ethyl carbamoyl, benzyl carbamoyl, trifluoroacetyl, or isobutyl carbamoyl, the method comprising the steps of:

a. reacting

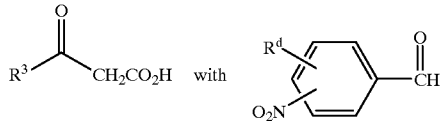

to form

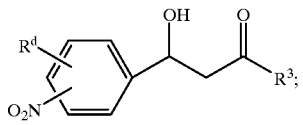

b. reacting

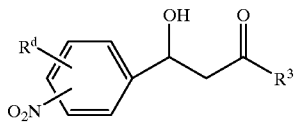

with acetic anhydride to form

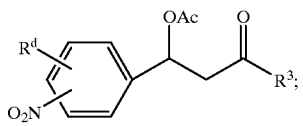

c. reacting the

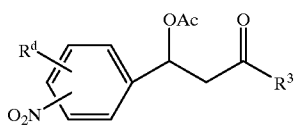

with $H_2$ to form

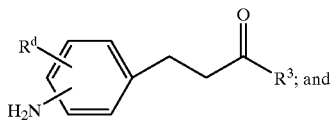

d. reacting the

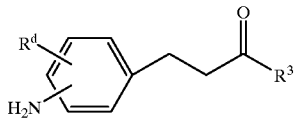

with an acylating agent to form

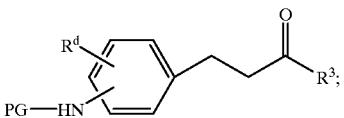

e. reacting the

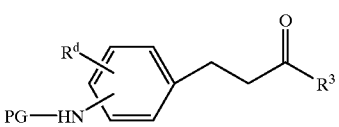

with benzyl acetate or $C_1$–$C_6$ alkyl acetate to form

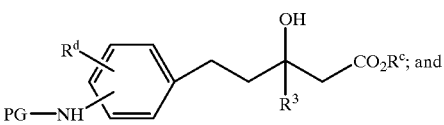

wherein $R^c$ is benzyl or $C_1$–$C_6$ alkyl;

f. reacting the

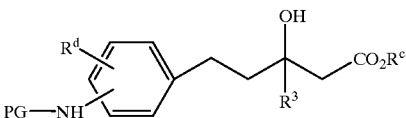

with $H_2$ if $R^c$ is benzyl or aqueous base if $R^c$ is benzyl or $C_1$–$C_6$ alkyl to provide

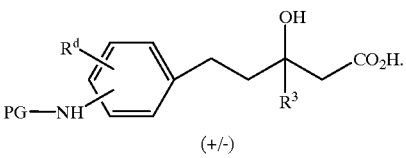

In a preferred embodiment, the acylating agent is acetic anhydride, formic acetic anhydride, methyl formate, ethyl formate chloroformate, benzyl chloroformate, or isobutyl chloroformate, trifluoroacetic anhydride.

In another preferred embodiment, the acylating agent is acetic anhydride.

In another preferred embodiment,

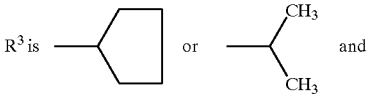

$R^d$ is hydrogen.

Also provided is a method of making
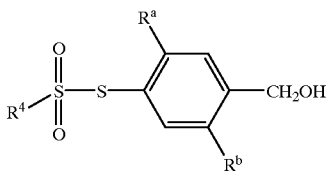
wherein R⁴ is tolyl, phenyl, or methyl, and $R^a$ and $R^b$ are independently $C_1$–$C_6$ alkyl, the method comprising the steps of:
a. reacting
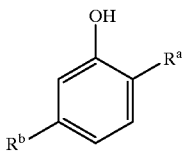
with a Lewis acid catalyst, and tri-$C_1$–$C_6$ alkyl orthoformate or dichloromethyl methyl ether to form
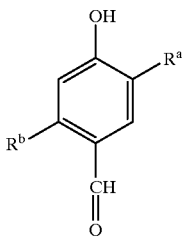
b. reacting
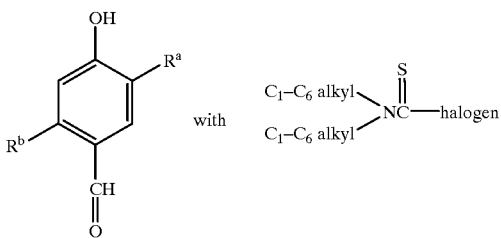
to give
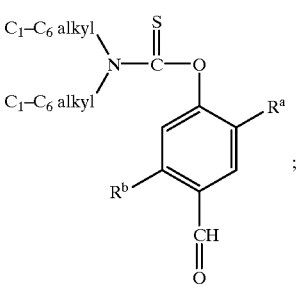
c. heating
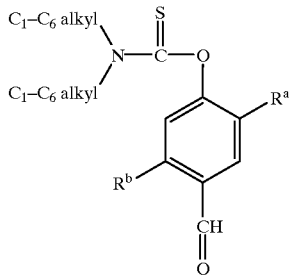
to produce
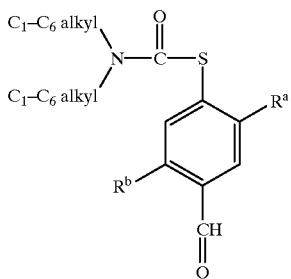
d. reacting
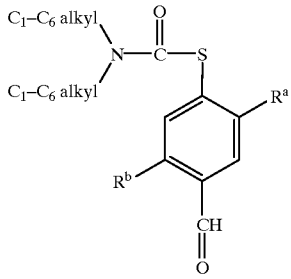
with a reducing agent to give
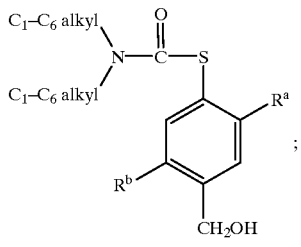

e. heating

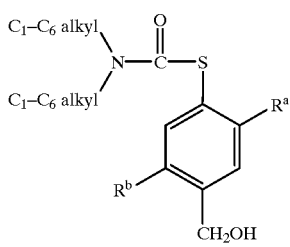

with a base to give

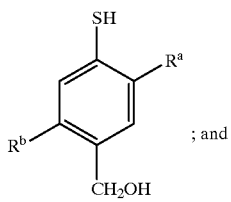
; and f. reacting the

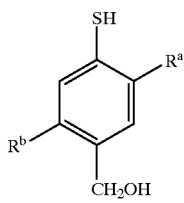

with a sulfonating agent $R^4SO_2$ halogen to give

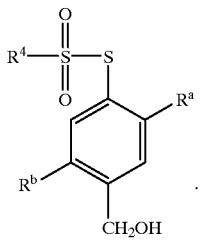
.

In a preferred embodiment of the method, the reducing agent is sodium borohydride or lithium borohydride.

In another preferred embodiment, the sulfonating agent $R^4SO_2$halogen is toluenesulfonyl chloride, benzenesulfonyl chloride, methanesulfonyl chloride, or toluenesulfonylbromide.

In another preferred embodiment, the Lewis acid catalyst is $AlCl_3$.

In another preferred embodiment,

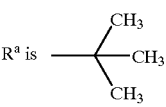

and $R^b$ is $-CH_3$.

Also provided is a method of making

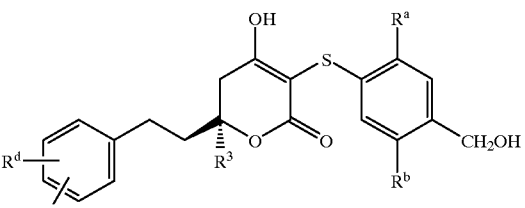

wherein

R3 is $C_2-C_8$ alkyl or $C_1-C_6$ alkyl, $R^a$ and $R^b$ are independently $C_1-C_6$ alkyl, and $R^d$ is hydrogen, halogen, or $C_1-C_6$ alkyl, the method comprising the steps of:

a. reacting

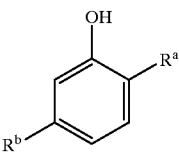

with a Lewis acid catalyst, and tri-$C_1-C_6$ alkyl orthoformate or dichloromethyl methyl ether to form

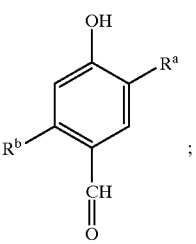
;

b. reacting
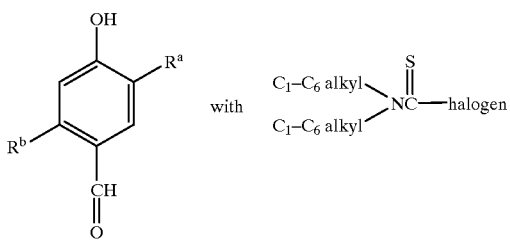
to give
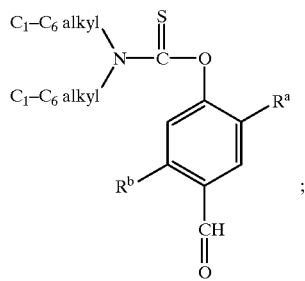
c. heating
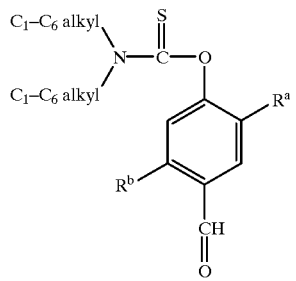
to produce
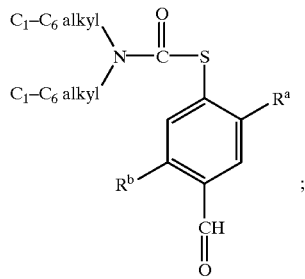
d. reacting
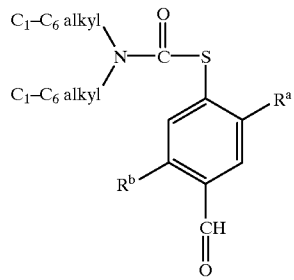
with a reducing agent to give
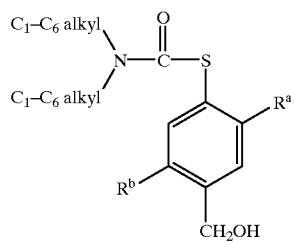
e. heating
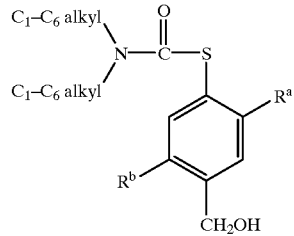
with a base to give
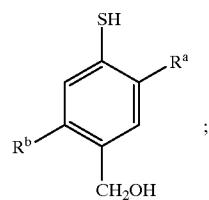
f. reacting the
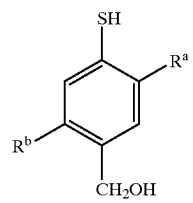
with a sulfonating agent $R^4SO_2$-halogen wherein $R^4$ is tolyl, phenyl, or methyl to give

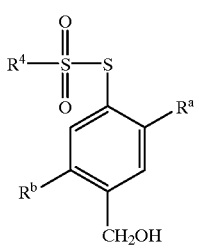

g. reacting

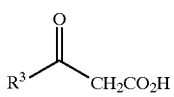 with 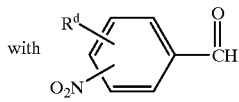

to form

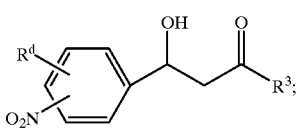

h. reacting

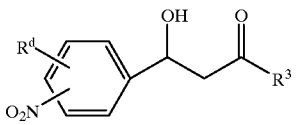

with acetic anhydride to form

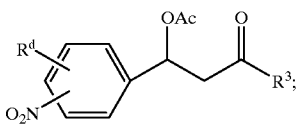

i. reacting

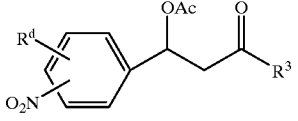

with a base to form

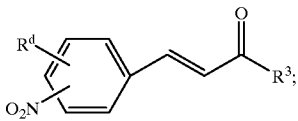

j. reacting

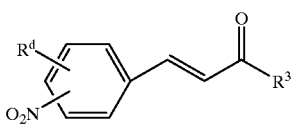

with benzyl acetate or $C_1$–$C_6$ alkyl acetate to form

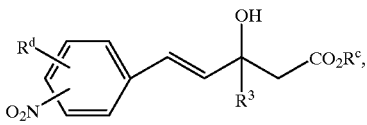

wherein $R^c$ is benzyl or $C_1$–$C_6$ alkyl;

k. reacting

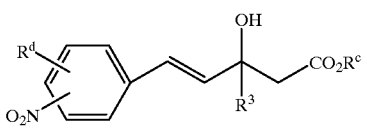

with $H_2$ when $R^c$ is benzyl or aqueous base when $R^c$ is benzyl or $C_1$–$C_6$ alkyl to give

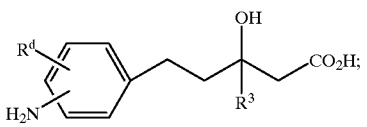

l. reacting

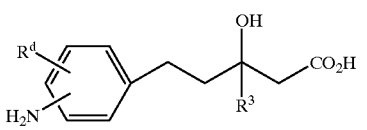

with an acylating agent to form

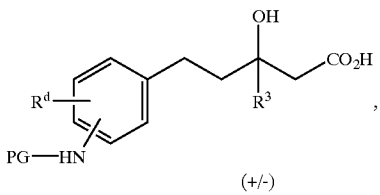

wherein PG is a protecting group selected from acetyl, formyl, propionyl, benzoyl, methyl carbamoyl, ethyl carbamoyl, benzyl carbamoyl, trifluoroacetyl, or isobutyl carbamoyl;

m. treating the
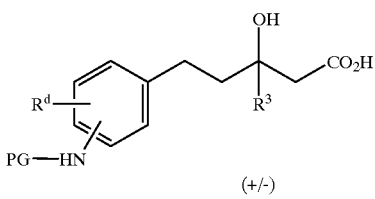
(+/-)
with (S)-N-benzyl-α-methyl benzylamine;
n. allowing crystals to form;
o. collecting the crystals;
p. isolating
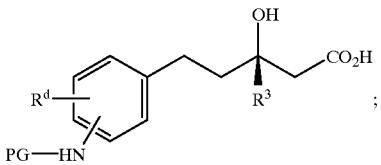
q. reacting
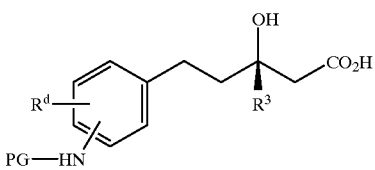
with carbonyl diimidazole to form
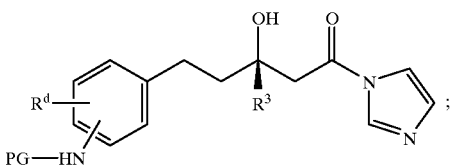
r. reacting the
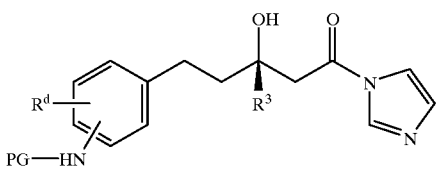
with a compound of the formula
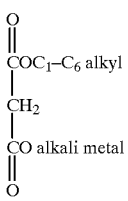
and MgCl$_2$ to form
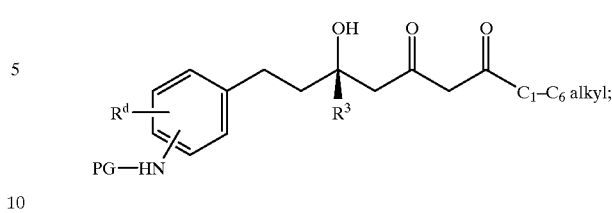
s. reacting the
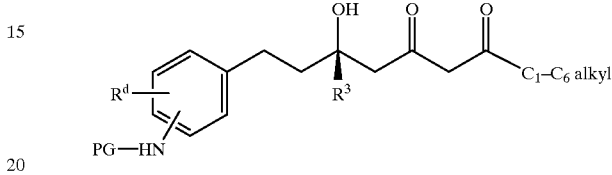
with a base to form
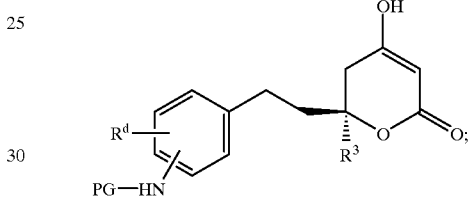
t. reacting
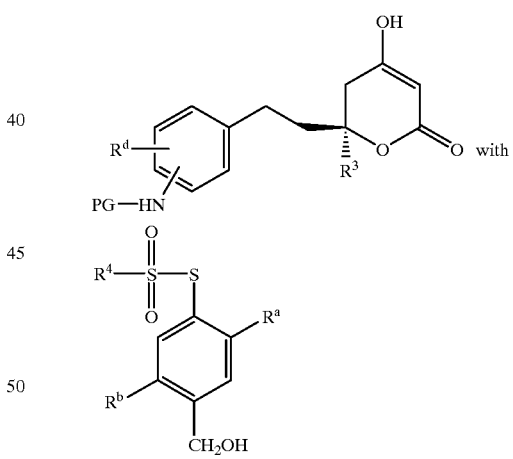
in the presence of a tertiary amine base to give
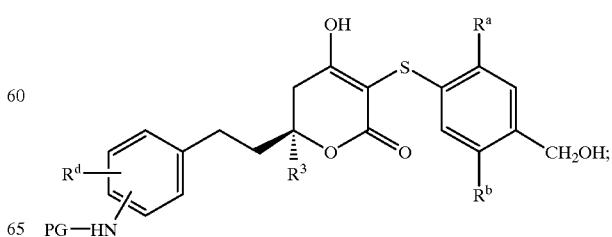

u. reacting

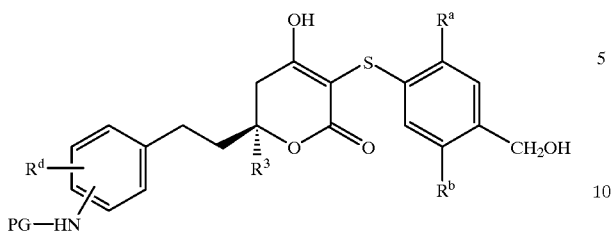

with a base to form

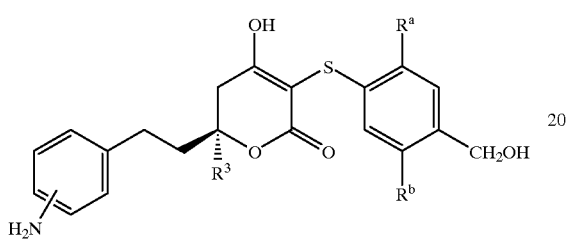

In a preferred embodiment,

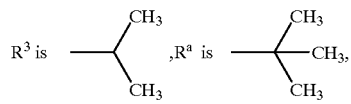

$R^b$ is —CH$_3$, and $R^d$ is hydrogen.

In a preferred embodiment, in Step a the Lewis acid catalyst is AlCl$_3$ and the tri-C$_1$–C$_6$ alkyl orthofornate is triethyl orthoformate. In a preferred embodiment, in Step b the

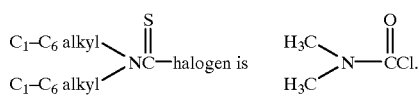

In a preferred embodiment, in Step d the reducing agent is NaBH$_4$.

In a preferred embodiment, in Step e the base is sodium hydroxide.

In a preferred embodiment, in Step f the sulfonating agent R$^4$—SO$_2$-halogen is

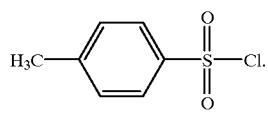

In a preferred embodiment, in Step j the acylating agent is acetic anhydride.

In another preferred embodiment, in Step t the tertiary amine base is triethyl arnine.

In another preferred embodiment, in Step u the base is sodium hydroxide.

Also provided is a method of making

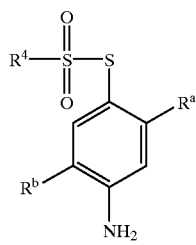

wherein $R^4$ is tolyl, phenyl, or methyl, and $R^a$ and $R^b$ are independently C$_1$–C$_6$ alkyl, the method comprising the steps of:

a. reacting

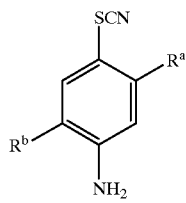

with (tert-butyl OCO)$_2$O to give

b. reacting

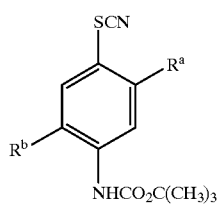

with NaSH and NaBH$_4$ to form

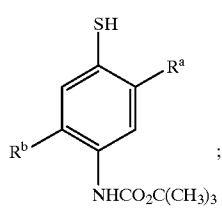

c. reacting

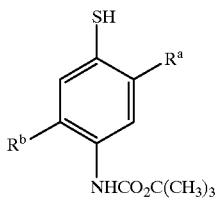

with a sulfonating agent

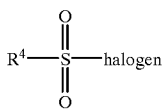

to give

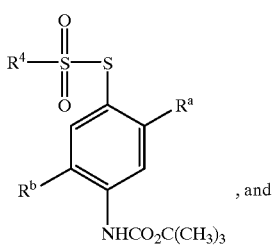

, and d. reacting

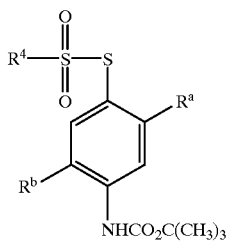

with an acid to form

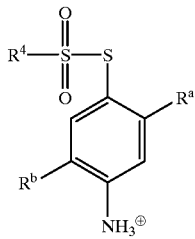

In a preferred embodiment, the sulfonating agent

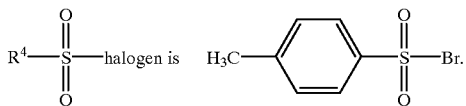

In a preferred embodiment, wherein the acid is HCl.

Also provided is a method of making

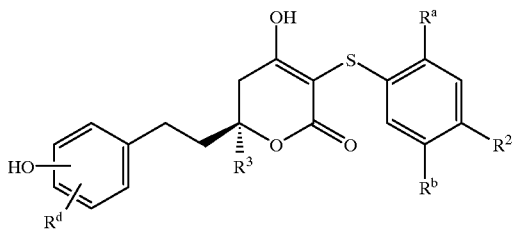

wherein $R^3$ is $C_2$–$C_8$ cycloalkyl or $C_1$–$C_6$ alkyl; $R^a$ and $R^b$ are independently $C_1$–$C_6$ alkyl, $R^d$ is hydrogen, $C_1$–$C_6$ alkyl or halogen, and $R^2$ is $NH_2$ or —$CH_2OH$, the method comprising the step of:

a. reacting

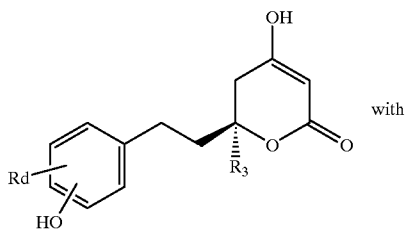 with

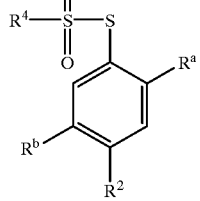

in the presence of a base to form

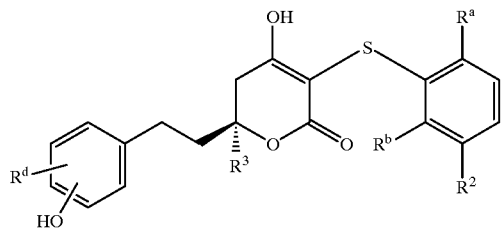

wherein $R^4$ is tolyl, phenyl, or methyl.

In a preferred embodiment, the base is $K_2CO_3$.

In a preferred embodiment, the base is $K_2CO_3$ and the solvent is dimethylformamide.

In a preferred embodiment, $R^3$ is 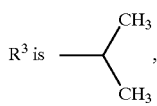, $R^2$ is —NH$_2$, $R^a$ is

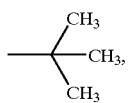

$R^b$ is —CH$_3$ and $R^d$ is hydrogen.
In a preferred embodiment,

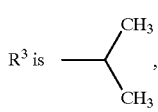

$R^2$ is —CH$_2$OH, and $R^a$ is

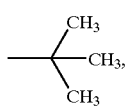

$R^b$ is —CH3 and $R^d$ is hydrogen.
In a preferred embodiment,

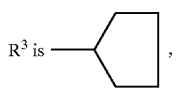

$R^2$ is —CH$_2$OH, and $R^a$ is

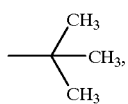

$R^b$ is —CH$_3$ and $R^d$ is hydrogen

Also provided is a method of making

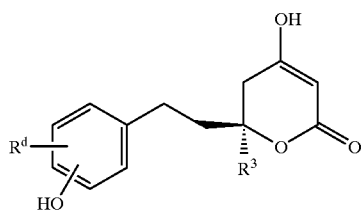

wherein $R^3$ is C$_1$–C$_6$ alkyl or C$_2$–C$_8$ cycloalkyl, $R^d$ is hydrogen, halogen, or C$_1$–C$_6$ alkyl, the method comprising the steps of:

a. reacting

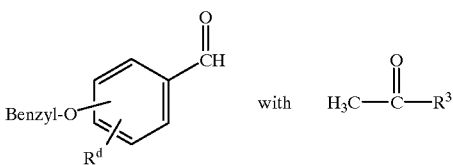

to form

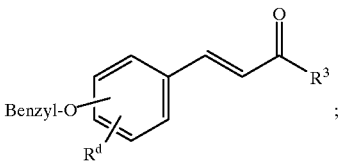

b. reacting

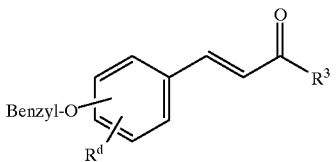

with H$_2$ to give

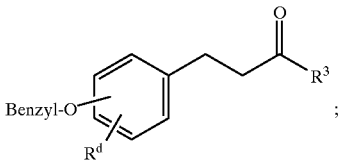

c. reacting

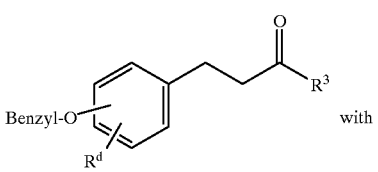

with

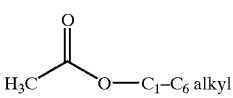

to form

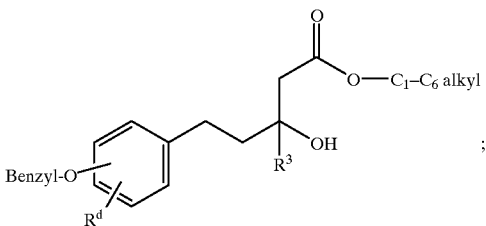

d. reacting

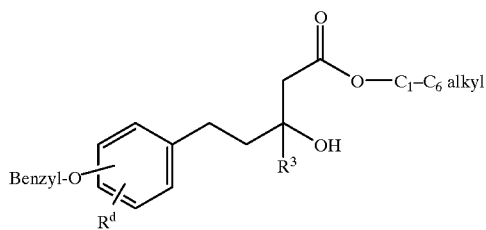

with a base to form

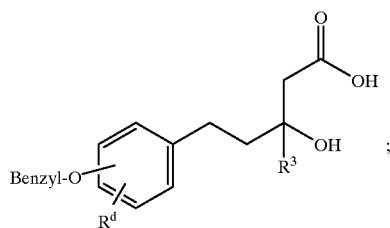

e. reacting

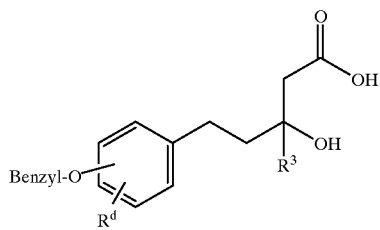

with S-α-methyl benzyl amine;
f. allowing crystals to form;
g. collecting the crystals;
h. isolating

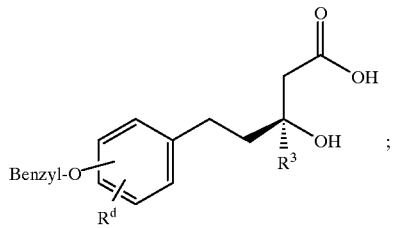

i. reacting

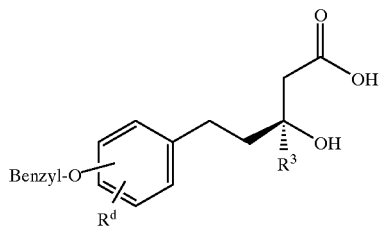

with carbonyl diimidazole to form

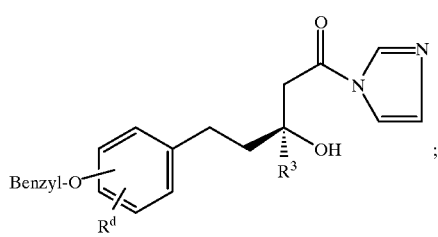

j. reacting

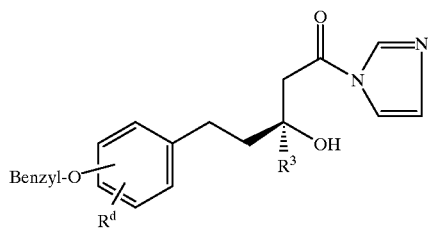

with MgCl$_2$ and $\begin{array}{c}\text{O}\\ \parallel\\ \text{COC}_1\text{–C}_6 \text{ alkyl}\\ \mid\\ \text{CH}_2\\ \mid\\ \text{CO alkali metal}\\ \parallel\\ \text{O}\end{array}$ to produce

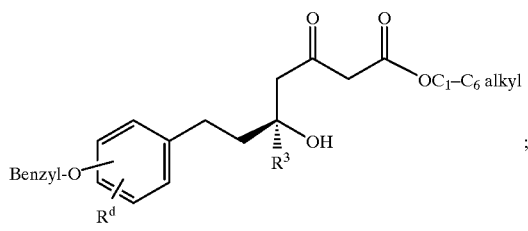

k. reacting

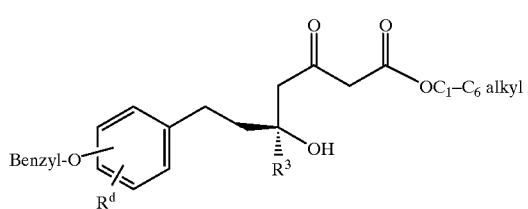

with a base to form

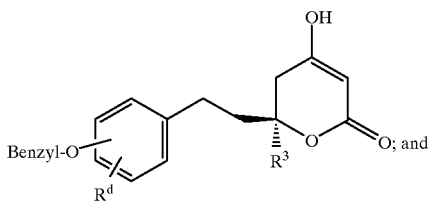

l. reacting

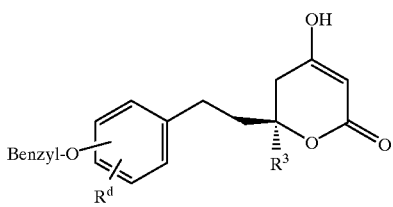

with H₂ to form

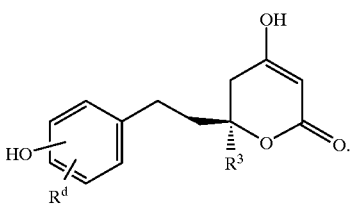

In a preferred embodiment,

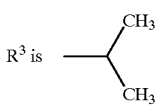

and $R^d$ is hydrogen.
In a preferred embodiment,

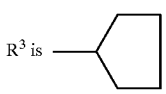

and $R^d$ is hydrogen.
In a preferred embodiment, in Step d the base is potassium hydroxide.
In a preferred embodiment, in Step k the base is potassium hydroxide.
In a preferred embodiment,

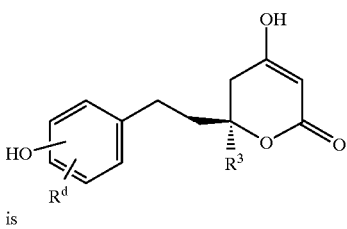

is

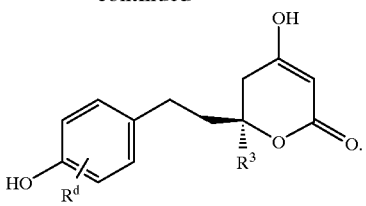

Also provided is a method of making

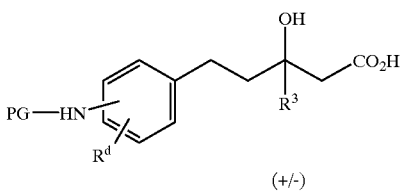

wherein $R^3$ is $C_2$–$C_8$ cycloalkyl or $C_1$–$C_6$ alkyl;

$R^d$ is hydrogen, halogen, or $C_1$–$C_6$ alkyl; and

PG is a protecting group selected from acetyl, formyl, propionyl, benzyl, methyl carbamoyl, ethyl carbamoyl, benzyl carbamoyl, trifluoromethyl, or isobutyl carbamoyl, the method comprising the steps of a. reacting

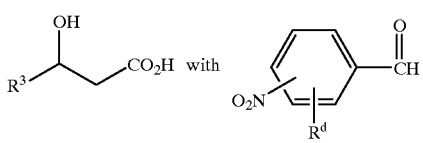

to form

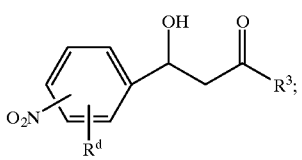

b. reacting

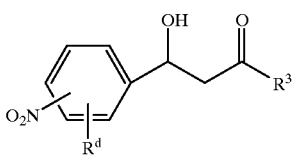

with acetic anhydride to form c. reacting

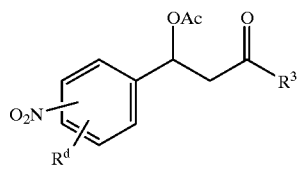

with a base to form

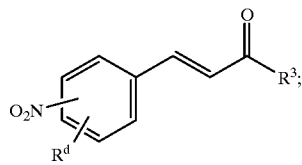

d. reacting

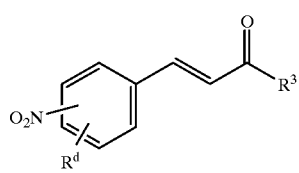

with benzyl acetate or $C_1$–$C_6$ alkyl acetate to form

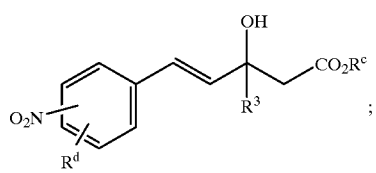

wherein $R^c$ is benzyl or $C_1$–$C_6$ alkyl;

e. reacting

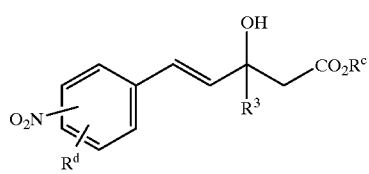

with $H_2$ to give

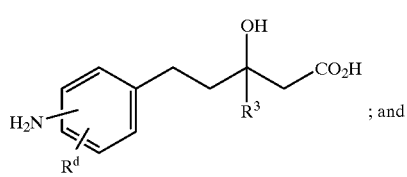

; and f. reacting

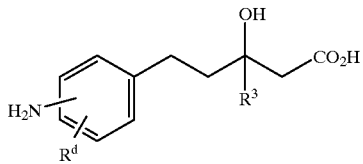

with an acylating agent to form

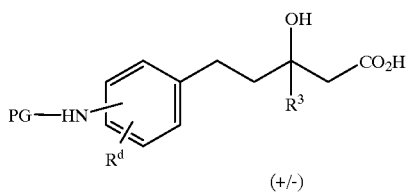

(+/-)

Also provided is a method of making

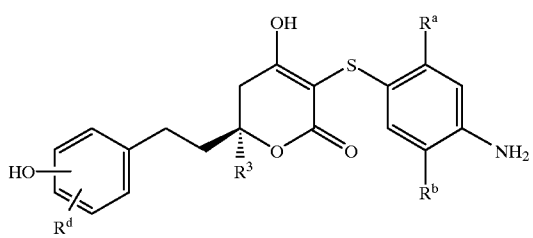

wherein $R^3$ is $C_1$–$C_6$ alkyl or $C_2$–$C_8$ cycloakyl, $R^a$ and $R^b$ are independently $C_1$–$C_6$ alkyl, and $R^d$ is hydrogen, halogen, or $C_1$–$C_6$ alkyl, the method comprising the steps of:

a. reacting

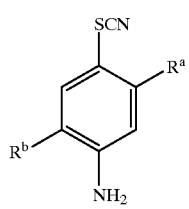

with (tert-butyl $OCO)_2O$ to give

;

b. reacting
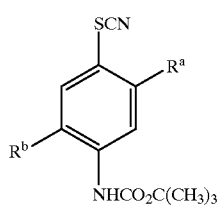
with NaSH and NaBH₄ to form
;
c. reacting
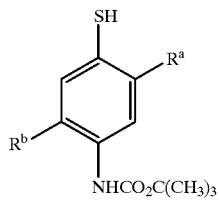
with a sulfonating agent
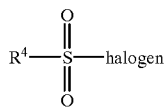
to give
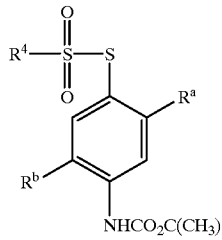
,
wherein R⁴ is tolyl, phenyl, or methyl;
d. reacting
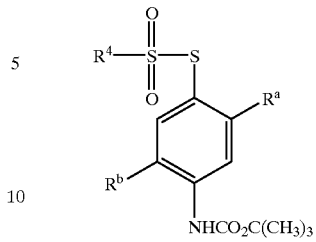
with an acid to form
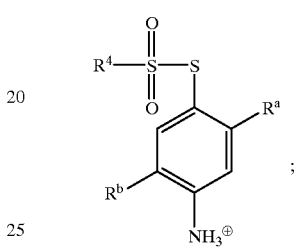
;
e. reacting
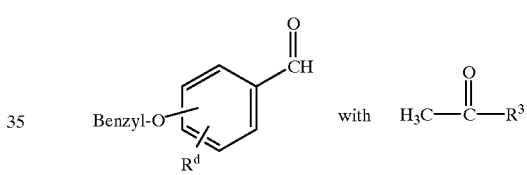 with 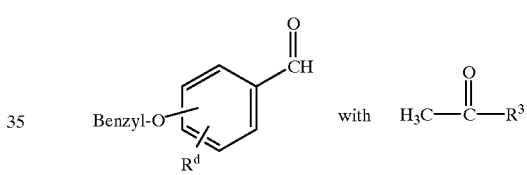
to form
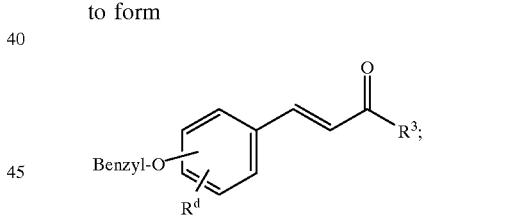
;
f. reacting
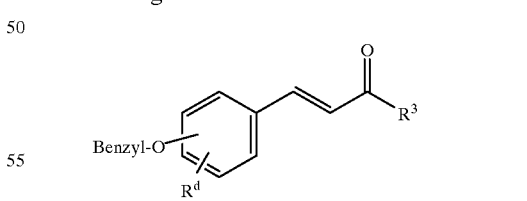
with H₂ to give
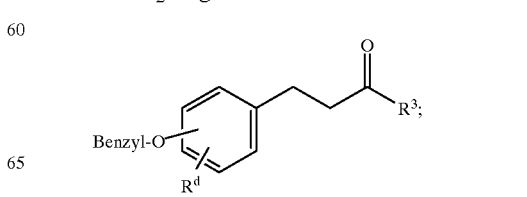

g. reacting
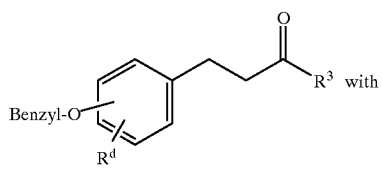
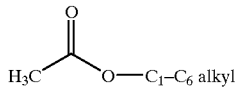
to form
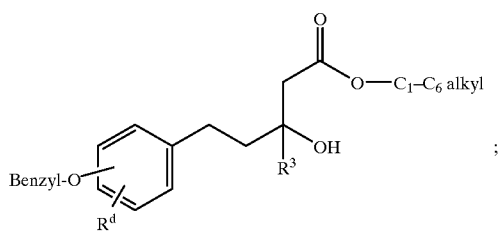
h. reacting
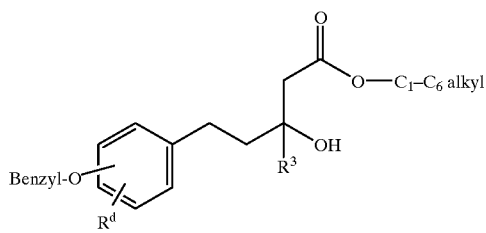
with a base to form
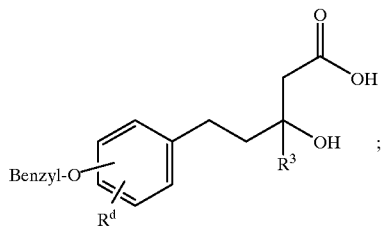
i. reacting
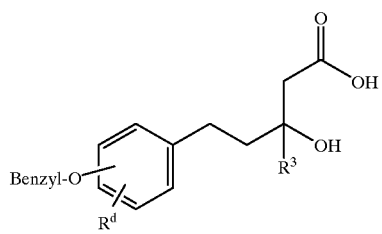
with S-α-methylbenzylamine;
j. allowing crystals to form;
k. collecting the crystals;
l. isolating
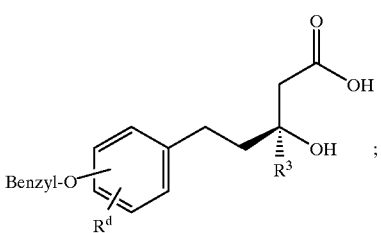
m. reacting
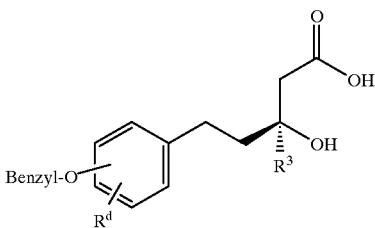
with carbonyl diimidazole to form
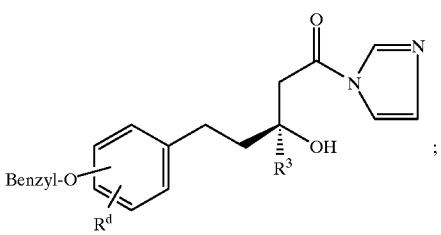
n. reacting
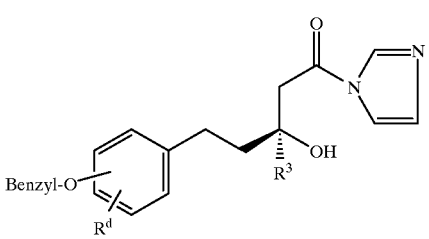
with MgCl$_2$ and 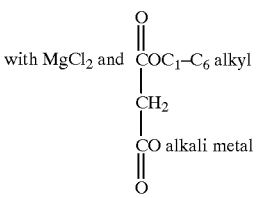

to produce

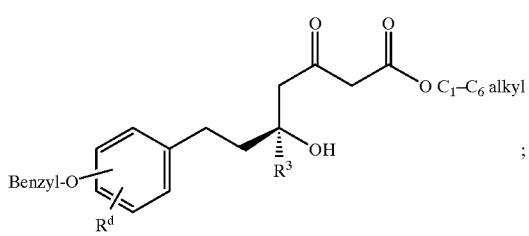

o. reacting

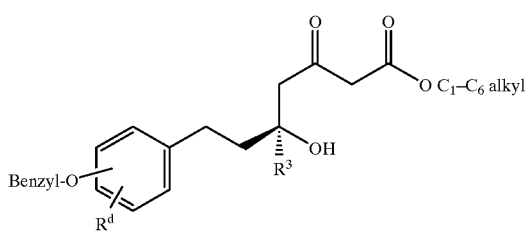

with a base to form

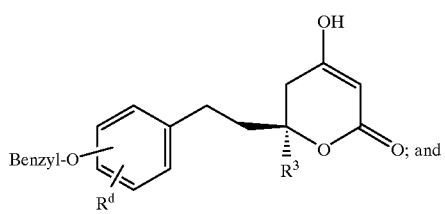; and p. reacting

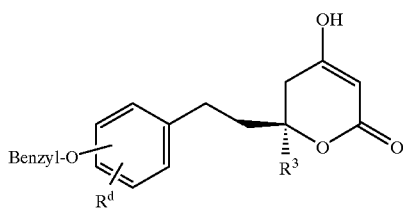

with H₂ to form

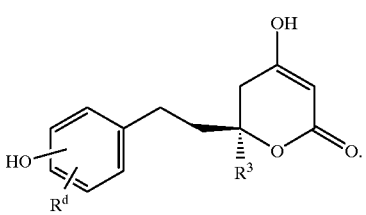

q. reacting

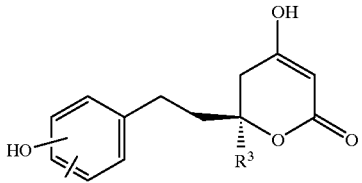

with

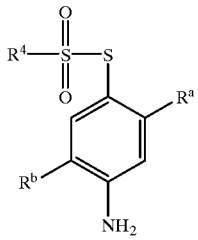

in the presence of a base to form

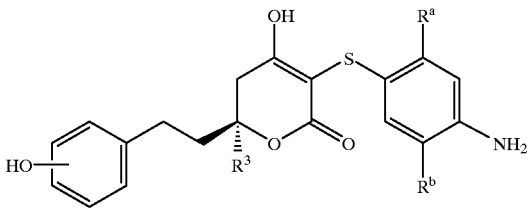

In a preferred embodiment,

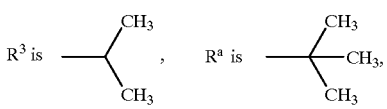

$R^b$ is —CH₃, and $R^d$ is hydrogen.

In another preferred embodiment, the sulfonating agent

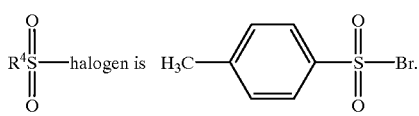

In another preferred embodiment, the acid is HCl.
In another preferred embodiment, in Step h in base is sodium hydroxide.
In another preferred embodiment, in Step o the base is potassium hydroxide.
Also provided are the compounds (+/−)-3-[2-(4-Acetylamino-phenyl)-ethyl]-3-hydroxy-4-methyl-pentanoic acid benzyl ester;

(S)-N-{4-[3-Hydroxy-3-(2-imidazol-1-yl-2-oxo-ethyl)-4-methyl-pentyl]-phenyl}-acetamide;

(S)-3-[2-(4-Benzyloxy-phenyl)-ethyl]-3-hydroxy-1-imidazol-1-yl-4-methyl-pentan-1-one;

4-Methyl-1-(4-nitro-phenyl)-pent-1-en-3-one;

(S)-5-(3-Benzyloxy-phenyl)-3-cyclopentyl-3-hydroxy-1-imidazol-1-yl-pentan-1-one;

(+/−)-3-[2-(4-N-Acetylaminophenyl)ethyl]-3-hydroxy-4-methylpentanoic acid; and (5-tert-Butyl-4-mercapto-2-methyl-phenyl)-carbamic acid tert-butyl ester.

DETAILED DESCRIPTION OF THE INVENTION

The present invention relates to methods of making dihydropyrone HIV protease inhibitors. The methods involve a coupling reaction of two intermediates to form the product HIV protease inhibitor. This coupling reaction can be used with various intermediates to form HIV protease inhibitors.

The specific syntheses disclosed herein are intended to exemplify certain embodiments of the invention, and are not intended to limit the scope of the specification or claims in any matter.

The term "alkyl" means a straight or branched chain hydrocarbon having from 1 to 8 carbon atoms. Examples of alkyl groups include methyl, ethyl, propyl, isopropyl, butyl, tert-butyl, octyl, and the like.

The term "acylating agent" means a chemical reagent that reacts with a compound to add an acyl group

to the compound. An acyl group is an organic radical derived from an organic acid by the removal of the hydroxyl group. Representative examples of acylating agents include, but are not limited to acetic anhydride, formic acetic anhydride, methyl formate, ethyl chloroformate, benzyl chloroformate, and isobutyl chloroformate.

The term "Lewis acid catalyst" means a Lewis acid that is used as a catalyst for a chemical reaction. A Lewis acid is an electron pair acceptor. Examples of Lewis acid catalysts include, but are not limited to, $AlCl_3$, $AlBr_3$, $ZnCl_2$, $BF_3$, and $TiCl_4$.

The term "halogen" means chlorine, fluorine, bromine, or iodine.

The term "reducing agent" means a chemical reagent that is readily oxidized by reducing another chemical. Examples of reducing agents include, but are not limited to, hydrogen, $LiAlH_4$, and $NaBH_4$.

The term "base" means a chemical reagent that yields a hydroxyl ion in aqueous solution and which reacts with an acid to form water and a salt. Another definition of a base is a chemical reagent that is an electron donor. Examples of bases include, but are not limited to, potassium hydroxide, sodium hydroxide, $NaHCO_3$, $Na_2CO_3$ $K_2CO_3$, $KHCO_3$, pyridine, and triethylamine.

The term "acid" means a chemical reagent that yields a proton ($H^+$) in aqueous solution and which reacts with a base or metals to form water and a salt. Another definition of an acid is a chemical reagent that is an electron pair acceptor. Examples of acids include, but are not limited to, hydrochloric acid, hydrobromic acid, hydriodic acid, and acetic acid.

The term "sulfonating agent" means a chemical reagent that can substitute a hydrogen atom on a compound with a —$SO_3H$ group or —$SO_3R$ group. Examples of sulfonating agents include, but are not limited to,

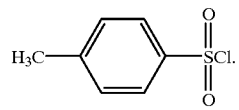

The term "protecting group" is an organic group that has converted a reactive functional group on a compound into an unreactive functional group so that a reaction can be run on the compound without the reactive functional group interfering with the reaction. Examples of reactive functional groups that can be protected include, but are not limited to, alcohols, aldehydes, ketones, carboxylic acids (—$CO_2H$), and amines. The protecting group used depends on the functional group to be protected. For example, amines can be protected by acetyl groups.

A comprehensive guide to protecting groups can be found in Greene T. W., *"Protective Groups in Organic Synthesis,"* John Wiley & Sons, Inc, New York, 1981, which is hereby incorporated by reference.

The following abbreviations are used throughout this application.

| | |
|---|---|
| Ac | acetyl |
| Me | methyl |
| Et | ethyl |
| Ph | phenyl |
| HPLC | high-pressure liquid chromatography |
| GC | gas chromatography |
| MeOH | methanol |
| ppt | precipitate |
| HOAc | acetic acid |
| MTBE | methyl tert-butyl ether |
| THF | tetrahydrofuran |
| psi | pounds per square inch |
| ROI | residue on ignition |
| TEGDME | tetraethylene glycol dimethyl ether |
| $Ac_2O$ | acetic anhydride |
| LDA | lithium diisopropyl amide |
| EtOAc | ethyl acetate |
| LOD | loss on drying |
| t-Bu | tert-butyl |
| BOC | tertiary butyloxy carbonyl |
| RI | refractive index |

Synthesis of (S)-3-(4-Amino-2-tert-butyl-5-methyl-phenylsulfanyl)-4-hydroxy-6-[2-(4-hydroxy-phenyl)-ethyl]-6-isopropyl-5,6-dihydropyran-2-one Step 1 Knoevenagel Condesation
Reaction Scheme

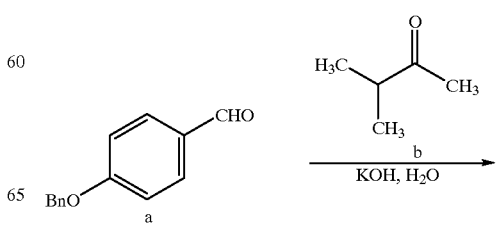

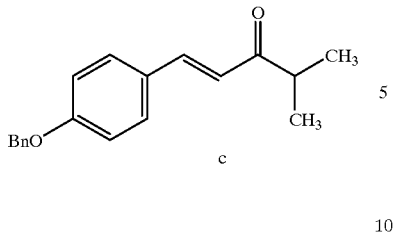

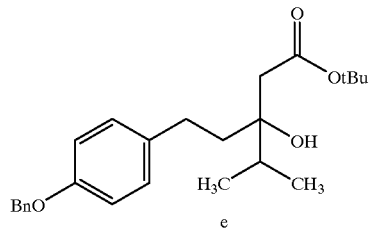

EXPERIMENTAL

To a 1 L flask was charged 100 g (474 mmol) of 4-benzyloxy-benzaldehyde (a) followed by 10 g of potassium hydroxide and 200 mL of ethanol. The reaction mixture was cooled to −5° C. and a solution of 3-methylbutan-2-one (b) (48.7 g, 565 mmol) in 170 mL of ethanol was added over a period of 4 hours. After 120 hours, the reaction was acidified by the addition of 300 mL of 0.83N HCl. The product was extracted into a mixture of 500 mL toluene and 50 mL ethyl acetate. The organics were washed with 100 mL water and concentrated to 132.3 g of an oil (c) (82% pure).

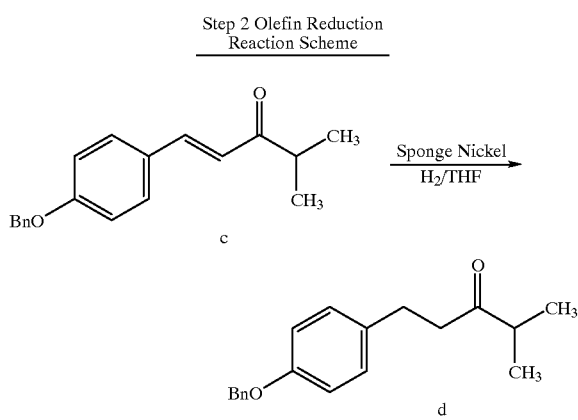

EXPERIMENTAL

To a 2 L Paar hydrogenator was charged 100 g (357 mmol) of (c), 4 g of Raney Nickel A7000 (Activated Metals & Chemicals, Inc., Sevierville, Tenn.) (50% water wet), and 1 L of tetrahydrofuran. The mixture was hydrogenated at 20° C. and 20 psi. The reaction was monitored by HPLC and was run for 22 hours. The catalyst was filtered and the resulting solution was concentrated under reduced pressure at 60° C. to afford 95.8 g of a clear oil (d).

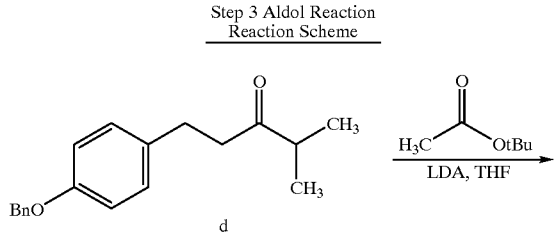

EXPERIMENTAL

To a 5 L flask was charged 126.5 g (1.25 mmol) diisopropylamine followed by 833 mL of tetrahydrofuran. The solution was cooled to −10° C. and a solution of n-butyl lithium (2.5 M in hexanes, 500 mL, 1.25 mmol) was added maintaining the reaction temperature around −10° C. The reaction was cooled to −40° C. and 146.6 g (1.26 mmol) of t-butyl acetate was added maintaining the temperature below −35° C. To the reaction was charged 234.4 g (830 mmol) of (d) maintaining the temperature at −40 to −50° C. After the addition, the reaction was allowed to stir 15 minutes. The reaction was quenched with 153.9 g (2.56 mol) of acetic acid maintaining the temperature below −25° C. The reaction was warmed to ambient temperature. To this was charged 2 L of ethyl acetate and a solution of 100 g of ammonium chloride in 450 mL of water.

The phases were separated and the aqueous phase was extracted again with 500 mL of ethyl acetate. The combined organic phases were washed with 250 mL of 10% aqueous sodium bicarbonate. The organics were concentrated under reduced pressure to afford 334 g of an oil (e) which was 88.2% pure.

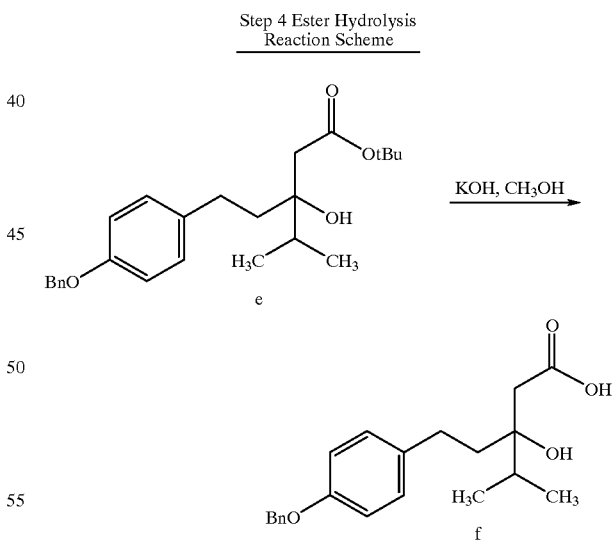

EXPERIMENTAL

To a 250 mL flask was charged 20 g (50 mmol) of (e) and 103 mL of methanol. To this was added a solution of 4 g potassium hydroxide dissolved in 21 mL water. The reaction was heated to reflux for 4 hours and then cooled to ambient temperature. The methanol was removed under reduced pressure. The residue was partitioned between water (350 mL) and methyl t-butyl ether (MTBE) (200 mL).

The organics were separated and the aqueous was washed with another 50 mL of MTBE. The combined organics were washed with water (50 mL). The combined aqueous layers were acidified to pH=4 with 37% aqueous hydrochloric acid and extracted with 2×100 mL ethyl acetate. This solution was charged to 200 g of heptane. After azeodrying under Dean-Stark conditions, the solution was cooled to ambient temperature. The crystals which precipitated were filtered and dried to afford 13.5 g of (f) (96% pure).

Step 5 Resolution Reaction Scheme

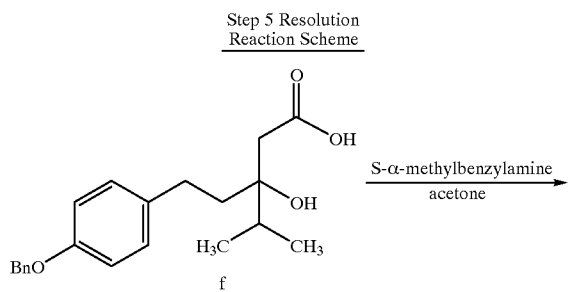

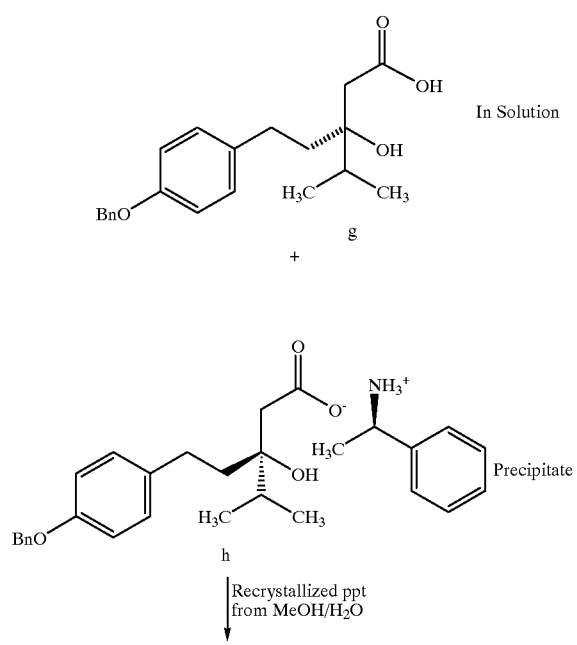

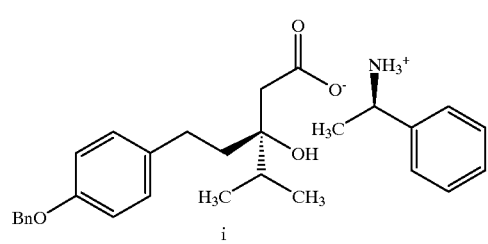

EXPERIMENTAL

To a 3 L flask was charged 330 g (963 mmol) of racemic acid (f) and 2.0 L of acetone. The solution was warmed to 42° C. To this was charged 58.4 g (480 mmol) of S-α-methylbenzylamine in one portion. The solution was cooled to 0° C. at ~10° C./hour and held at that temperature for at least 2 hours. The solids were filtered. (Note 1) The solids were dissolved in 1.8 L of methanol and then warmed to 50–55° C. Slowly added 1.2 L of water such that the temperature remained above 50° C. The solution was cooled at ~10° C./hour to 20° C. Held for at least 2 hours and filtered solids. The precipitate was dried at 50° C. in vacuo. This afforded 144 g (34%) of a white powder (i).

Notes

1) The S/R enantiomer ratio at this point is generally 94:6 although material as low as 66:34 cleans up well in the subsequent precipitation (multiple attempts may be required however). The enantiomers are separated using the following HPLC conditions: Chiracel OF column (Chiral Technologies, Inc., Exton, Pa.), 900:100:1 hexanes:2-propanol:HOAc, 1 mL/min, 230 nm. Retention times are 9.9 minutes (S) and 13.4 minutes (R).

Step 6 Acidification of Salt Reaction Scheme

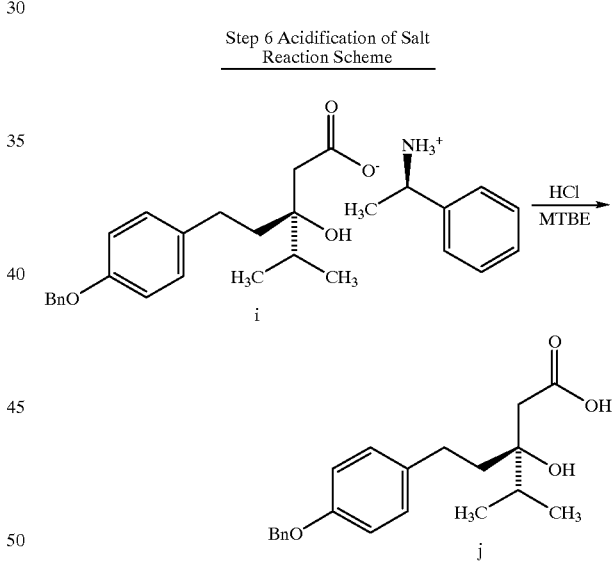

EXPERIMENTAL

Charged 325 g of resolved salt (i) to a 3 L flask. Charged 1.2 L of methyl t-butyl ether (MTBE) and 600 mL of water followed by a slow (15 minute) addition of 420 mL of 2N aqueous hydrochloric acid. The reaction was stirred until homogenous. The organic layer was separated, washed with 300 mL of 0.2N aqueous HCl and 600 mL of water. The organic layer was concentrated under reduced pressure and the resulting solid was dried in vacuo at 50° C. This afforded 131 g (98%) of a white solid (j). Purity was generally >99%.

Step 7 Dihydropyridone Formula Reaction Scheme

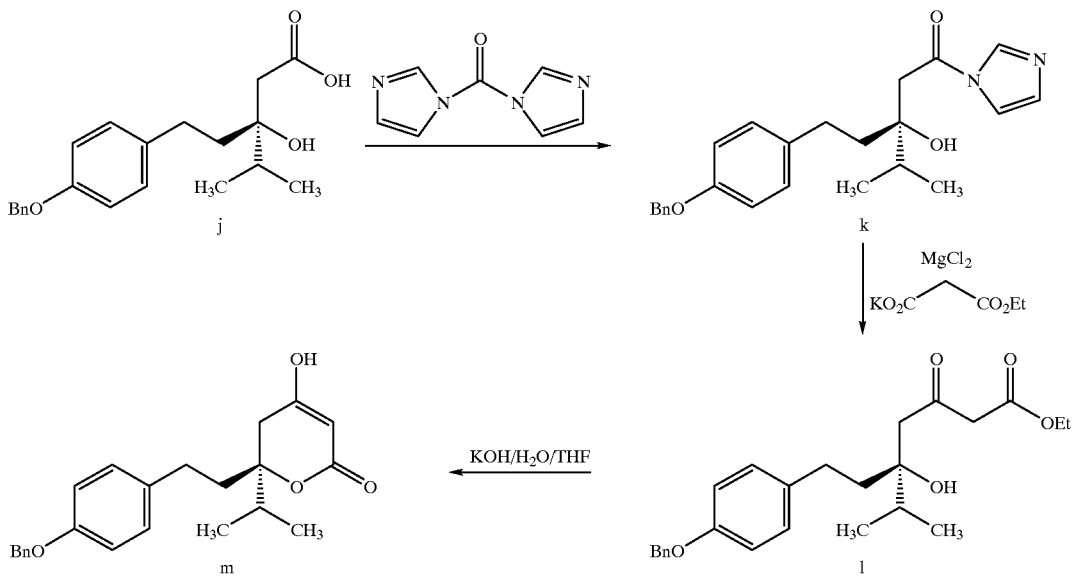

EXPERIMENTAL

To a 1 L flask was charged 100 g (292 mmol) of hydroxy acid (j) followed by 600 mL of tetrahydrofuran. To this was added 56.8 g of carbonyl diimidazole (350 mmol). This clear solution was stirred at ambient temperature for 4 hours. To a separate flask was charged 199 g (1.16 mol) of potassium ethyl malonate followed by 500 mL of acetonitrile and 200 mL of tetrahydrofuran. A 55.6 g (584 mmol) amount of magnesium chloride was added portionwise maintaining the temperature at less than 40° C. The reaction was stirred at 40° C. for 3 hours. After cooling this solution to 20° C., the imidazolide solution was charged. This solution was stirred at 25° C. overnight. The solvent was removed under reduced pressure. To the residue was charged 500 mL methyl t-butylether and 200 mL of water. The resulting solution was adjusted to pH=4 with 2N HCl (725 mL). The organics were separated, washed with 300 mL water and then with 200 mL 10% aqueous sodium bicarbonate. The organics were concentrated under reduced pressure.

The residue was dissolved in a mixture of 300 mL tetrahydrofuran and 900 mL 1N potassium hydroxide. The solution was stirred at ambient temperature for 3 hours. The solution was adjusted to pH=4 with concentrated HCl. The product was extracted with 500 mL ethyl acetate. The organics were concentrated under reduced pressure. To the residue was charged 150 mL of ethyl acetate followed by the slow addition of 400 mL of hexanes. The slurry was stirred for 4 hours and filtered. This yielded 58.9 g (56%) of benzyl dihydropyrone (m) as a white powder (96% purity).

Step 8 Debenzylation Reaction Scheme

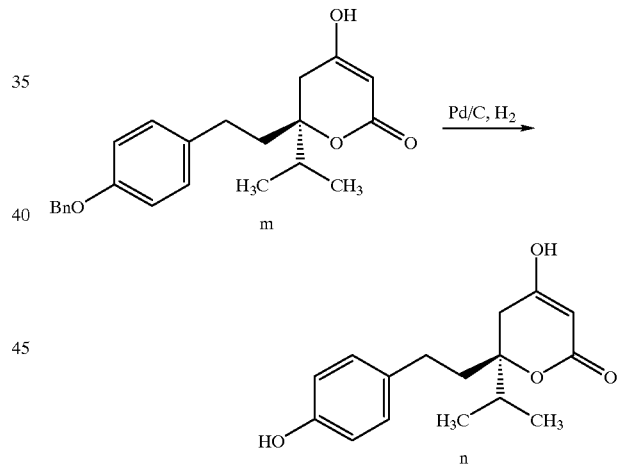

EXPERIMENTAL

To a 2 L Paar reactor was charged 105 g of the dihydropyrone benzyl ether (m) followed by 10 g of 10% palladium on carbon. The reactor was pressurized to 40 psi and the reaction was continued until no more hydrogen uptake was observed. The catalyst was filtered and the solution was concentrated to an oil. To the residue was added 100 g of methyl t-butyl ether and the solution was stirred for 12 hours. The resulting crystals were filtered and dried under reduced pressure at ambient temperature to afford 67.9 g (86%) of white crystalline (n).

Step 9 Coupling Reaction
Reaction Scheme

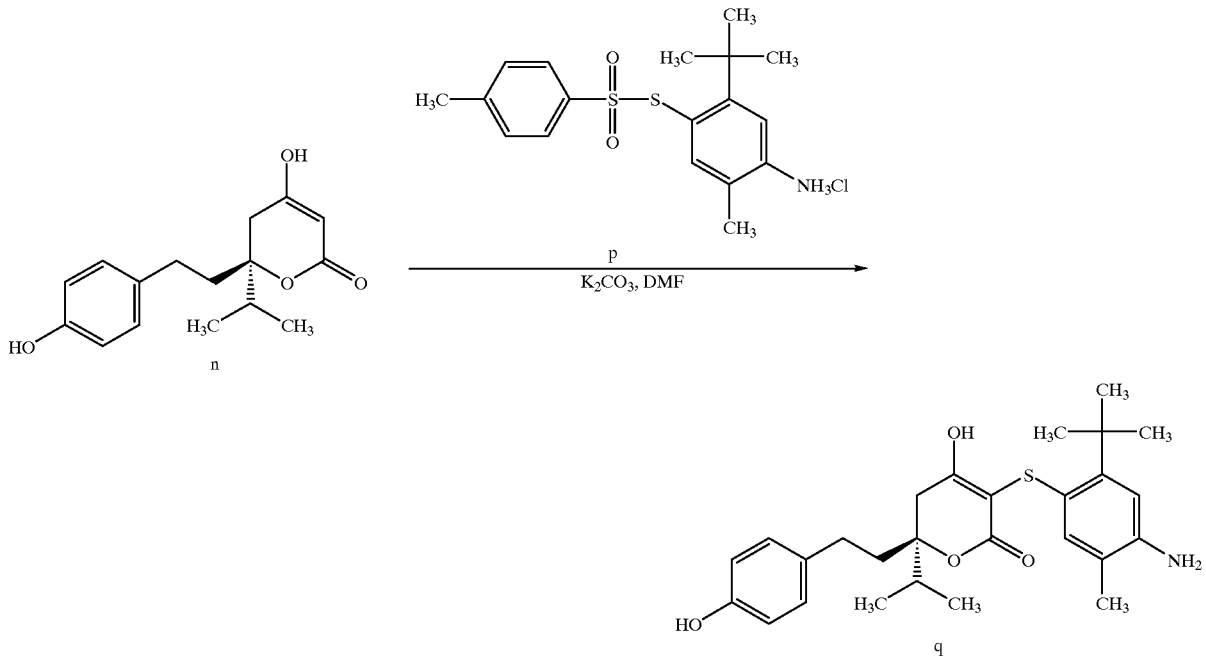

EXPERIMENTAL

A 78.4 g (203 mmol) amount of the tosylate hydrochloride salt (p) was charged to a 2 L flask under nitrogen. To this was charged 700 mL of ethyl acetate followed by 700 mL of saturated aqueous sodium bicarbonate. The reaction was stirred at ambient temperature until both layers were homogeneous. The layers were separated and the organics were washed with 200 mL of half saturated aqueous sodium chloride. The organics were concentrated under reduced pressure. To the residue was charged 120 mL of N,N-dimethylformamide. This was warmed to 35° C. under vacuum for 15 minutes to remove residual solvents and water. This solution was poured into a 250 mL flask.

To the flask was charged 76 g (550 mmol) of potassium carbonate followed by 50.1 g (181 mmol) of the dihydropyrone (n). The reaction was warmed to 35° C. and stirred until the starting material was not more than 0.2%. The reaction was poured into a mixture of 2 L of water and 1 L of methyl t-butyl ether. The layers were separated and the aqueous layer was washed with an additional 1 L of methyl t-butyl ether. The aqueous layer was cooled to 5° C. The pH of the solution was adjusted to 5.4 by slow addition of 1N HCl. A 7 L amount of ethyl acetate was warmed to 40° C. and then added to the slurry. The layers were separated and the organics were washed with 2×2 L of deionized water (pH 5–6).

The organics were concentrated under reduced pressure. To the residue was charged 700 mL of ethyl acetate and this slurry was stirred for 1 hour. To this was slowly charged 700 mL of hexanes and stirring was continued for 30 minutes. The solids were filtered and dried at 40° C. under reduced pressure. This afforded 71.6 g (84%) of (q) as a white solid.

Step 10 Disodium Salt Formation
Reaction Scheme

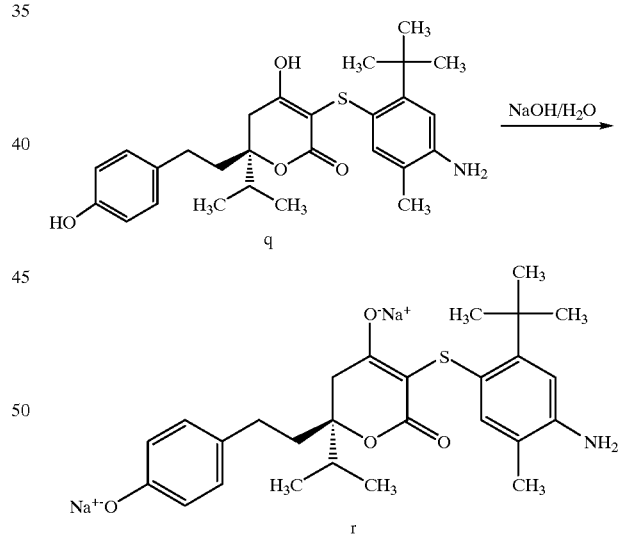

EXPERIMENTAL

A 25.0 g (53 mmol) amount of (q) was slurried in 50 mL of water and cooled to 5° C. To this was added dropwise 10.6 mL of 10N NaOH. The reaction was allowed to warm to ambient temperature and was stirred until homogeneous. The solution was filtered and concentrated at reduced pressure at not more than 50° C. The residue was dried in vacuo at 50° C. for 24 hours. The resulting glassy material was sieved through a 300 μm screen to produce 26.6 g (97%) of a tan powder, (r).

Synthesis of (S)-6-[2-(4-Aminophenyl)-ethyl]-3-(2-tert-butyl-4-hydroxymethyl-5-methylphenylsulfanyl)-4-hydroxy-6-isopropyl-5,6-dihydropyran-2-one and related compounds A Process for the Preparation of 5-tert-Butyl-4-hydroxy-2-methylbenzaldehyde 5-tert-Butyl-4-hydroxy-2-methylbenzaldehyde (1) is a key starting material required for the synthesis of 2-tert-butyl-4-hydroxymethyl-5-methylthiophenol and its S-arylsulfonyl and S-alkylsulfonyl derivatives (2). The latter are required intermediates needed for the synthesis of (S)-6-[2-(4-Amino-phenyl)-ethyl]-3-(2-tert-butyl-4-hydroxymethyl-5-methyl-phenylsulfanyl)-4-hydroxy-6-isopropyl-5,6-dihydro-pyran-2-one and related dihydropyrone HIV protease inhibitors

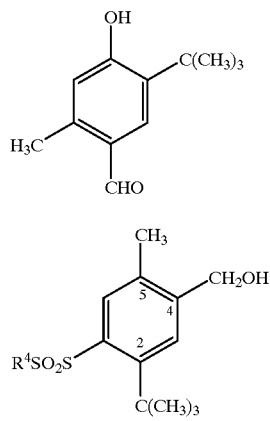

wherein $R^4$ is tolyl, phenyl, or methyl.

A Vilsmeier procedure has been used previously to prepare 1 from 2-tert-butyl-5-methylphenol in low yield (S. Morimura et. al., *Bull. Chem. So. Jpn.*, 50:2189 (1970); Cardillo et al., *Chem. Ind. (Milan)*, 49:630 (1967)). Formylation of phenols to produce various hydroxybenzaldehyde derivatives using triethyl orthoformate or dichloromethyl methyl ether in the presence of Lewis acid catalysts has been reported in the literature (e.g., see H. Gross, A. Rieche, G. Matthey, *Chem. Ber.*, 96:308 (1963); H. Meier, H. Kretzschmann, H. Kolshorn, *J. Org. Chem.*, 57:6847 (1992)). Using modifications of these methods, two efficient processes were developed for the synthesis of 5-tert-butyl-4-hydroxy-2-methylbenzaldehyde from the readily available and inexpensive starting material, 2-tert-butyl-5-methylphenol. All citations made throughout this application, including patents, applications, and journal articles, are hereby incorporated by reference.

General Description Procedure I

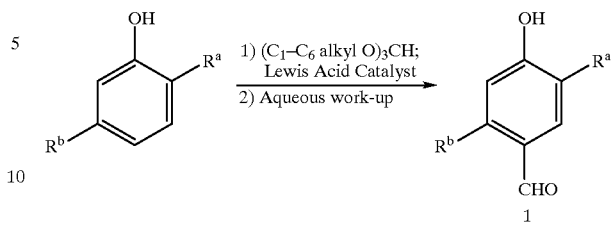

wherein $R^a$ and $R^b$ are independently $C_1$–$C_6$ alkyl.

A dialkyl phenol is allowed to react with a suitable trialkyl orthoformate such as triethyl orthoformate in the presence of a suitable Lewis acid catalyst such as $AlCl_3$ in a suitable solvent such as chlorobenzene, methylene chloride, toluene or a related solvent or solvent mixture in order to afford, after aqueous work-up and isolation, a dialkyl hydroxy benzaldehyde.

Specific Example

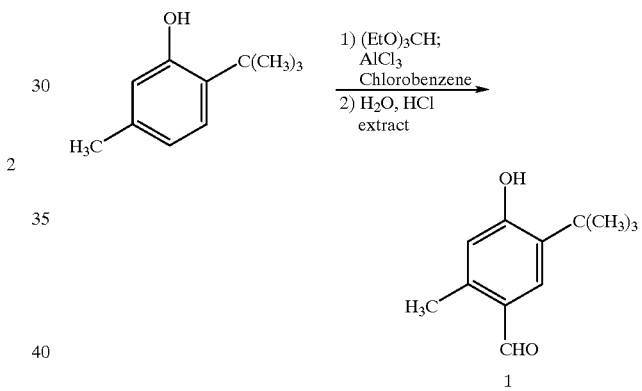

5-tert-Butyl-4-hydroxy-2-methylbenzaldehyde (1)

Aluminum chloride (26.6 gm, 200 mmol) was added to chlorobenzene (40 mL) and the mixture stirred and cooled to −10° C. A solution of 2-tert-butyl-5-methylphenol (16.4 gm, 100 mmol) in triethyl orthoformate (32.5 gm, 220 mmol) was added dropwise. On completion of the addition, the reaction mixture was warmed to 0–5° C. and held for 6 hours. Hydrochloric acid (100 mL of a 5% solution) was added to the reaction mixture. The mixture was extracted with (1:1) ethyl acetate/toluene (200 mL). The organic phase was extracted with 23% potassium hydroxide (3×50 mL) and water (25 mL) and the water extract combined with the three potassium hydroxide extracts. The pH of the combined extracts was adjusted to 4 with 37% hydrochloric acid. The resulting precipitate was collected and washed with water (3×50 mL) and vacuum dried 55° C. to give 5-tert-butyl-4-hydroxy-2-methylbenzaldehyde (1): 14.8 g (77 mmol, 77%): mp: 171–172° C.

General Description of Procedure II
Procedure II

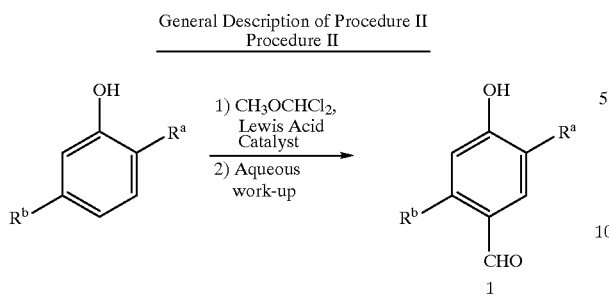

A dialkyl phenol is allowed to react with dichloromethyl methyl ether in the presence of a suitable Lewis acid catalyst such as $TiCl_4$ in a suitable solvent such as chlorobenzene, methylene chloride, toluene or a related solvent or solvent mixture in order to afford after aqueous work-up and isolation, a dialkyl hydroxy benzaldehyde (1).

SPECIFIC EXAMPLE

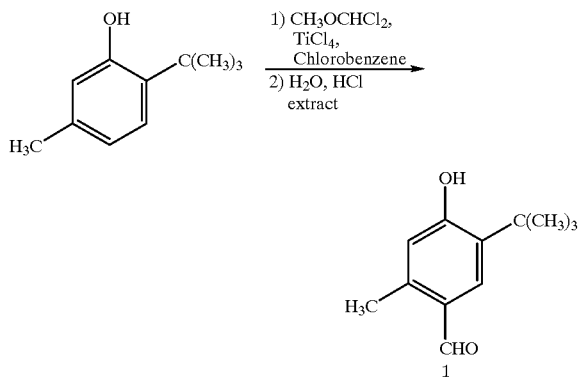

5-tert-Butyl-4-hydroxy-2-methylbenzaldehyde (1)

Chlorobenzene (100 mL) and 2-tert-butyl-5-methylphenol (20.6 gm, 125 mmol) were combined and the mixture stirred and cooled to 5° C. Titanium tetrachloride (27.5 mL) and dichloromethyl methyl ether (19 mL, 210 mmol) were added separately and simultaneously over 45 minutes while holding the reaction temperature between 4 and 7° C. The resulting mixture was stirred at 0–5° C. for 3 hours. Water (100 mL) was cautiously added over 18 minutes to the reaction mixture while holding the temperature below 14° C. The mixture was extracted with ethyl acetate (200 mL) and the resulting organic layer was extracted with 12% hydrochloric acid (2×75 mL). The combined aqueous acid layers were diluted with water (50 mL) and back extracted with ethyl acetate (100 mL). This extract was combined with the first ethyl acetate extract and the whole extracted with 15% KOH (3×100 mL). The KOH extracts were combined and the pH adjusted to 3 with 37% hydrochloric acid (62.8 gm). The resulting mixture was extracted with 1:1 ethyl acetate/toluene (2×150 mL). These organic extracts were combined and back extracted with water (2×50 mL) and the organic solution concentrated to approximately 75 mL. 5-tert-Butyl-4-hydroxy-2-methylbenzaldehyde seed crystals were added and the mixture stirred and cooled to 25° C. The mixture was filtered and the product washed with toluene (30 mL) and vacuum dried at 40° C. to give 5-tert-butyl-4-hydroxy-2-methylbenzaldehyde (1): 15 g (78 mmol, 62%): mp: 168–170° C.

A Process for the Preparation of 2-tert-Butyl-4-hydroxymethyl-5-methylthiophenol and S-arylsulfonyl and S-alkylsulfonyl Derivatives S-Arylsulfonyl and S-alkylsulfonyl derivatives (2) of 2-tert-butyl-4-hydroxymethyl-5-methylthiophenol are key intermediates for the synthesis of (S)-6-[2-(4-Aminophenyl)-ethyl]-3-(2-tert-butyl-4-hydroxymethyl-5-methyl-phenylsulfanyl)-4-hydroxy-6-isopropyl-5,6-dihydro-pyran-2-one and related dihydropyrone HIV protease inhibitors. In this process, the arysulfonyl group or alkylsulfonyl group is displaced as a leaving group in a coupling reaction of 2 with the nucleophilic center at the 3 position of the pyrone ring associated with a suitably substituted intermediate such as 24.

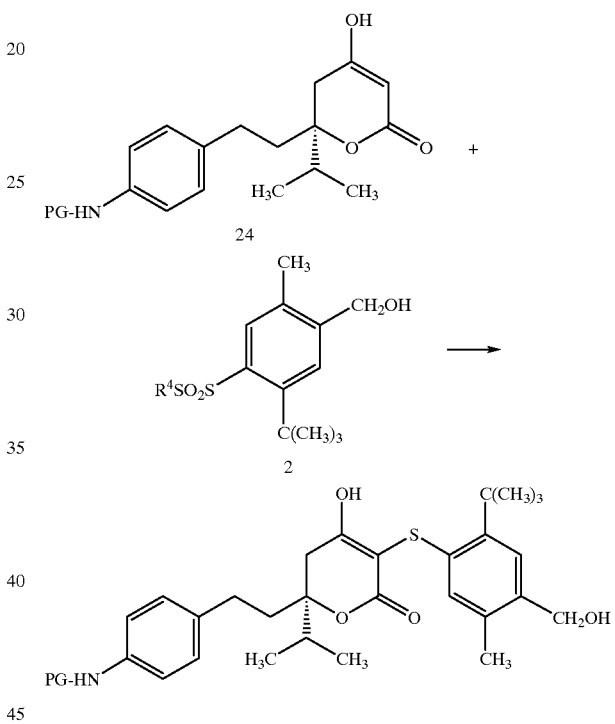

PG and $R^4$ are as defined herein.

A new, efficient process is proposed here for the synthesis of 2-tert-butyl-4-hydroxymethyl-5-methylthiophenol and its S-arylsulfonyl and S-alkylsulfonyl derivatives beginning with 5-tert-butyl-4-hydroxy-2-methylbenzaldehyde (1). Two procedures involving a total of five steps are required to prepare 2.

General Description of the Process

Procedure I

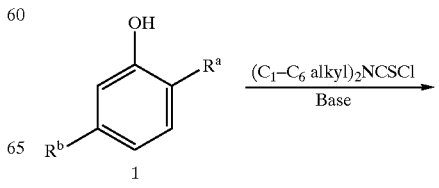

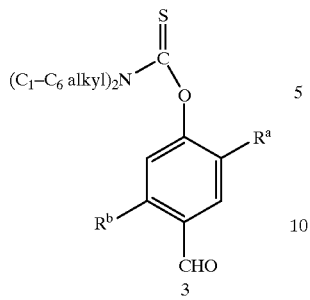

A dialkyl hydroxy benzaldehyde is allowed to react in a Schotten-Baumann reaction with a suitable N,N-dialkyl substituted thiocarbamoyl chloride such as N,N-dimethylthiocarbamoyl chloride in the presence of a suitable base such as potassium hydroxide or sodium hydroxide in a suitable organic-aqueous solvent system such as THF—H$_2$O to produce after work-up and isolation of the derivative (3).

Procedure II

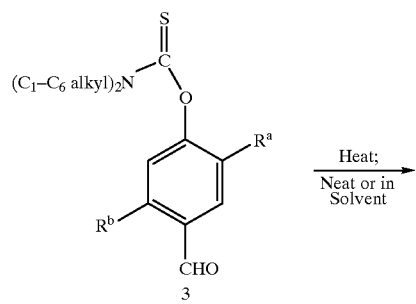

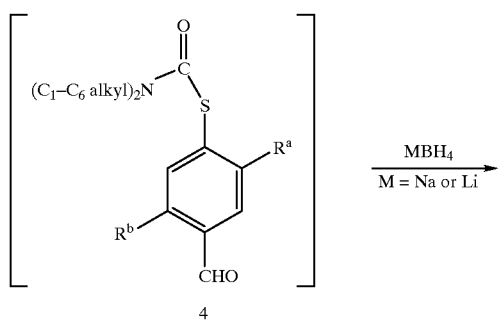

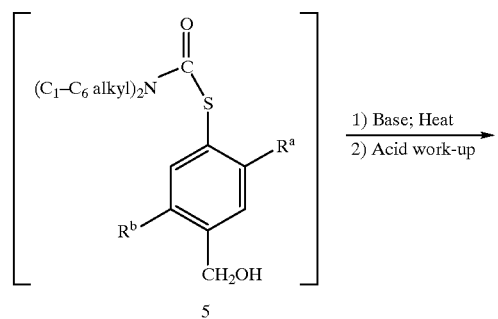

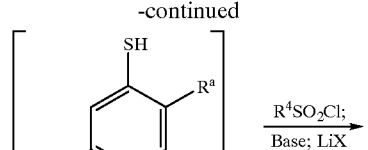

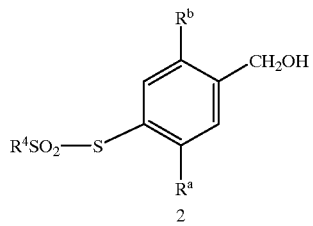

wherein X is a halogen.

In Procedure II, the derivatives (3) may be converted in 4 steps into the desired S-arylsulfonyl or S-alkylsulfonyl derivatives (2). The first step in this procedure is thermal rearrangement of (3) at 220–300° C. either neat or in a suitable high boiling solvent such as phenyl ether or tetraethyleneglycol dimethyl ether to give the corresponding ester derivatives (4). In the second step (4) is reduced with a suitable reducing agent such as NaBH$_4$ or LiBH$_4$ in a suitable solvent such as THF or MeOH to give the ester derivatives (5). In the third step (5) is hydrolyzed with heat using a suitable base such as NaOH or KOH in a suitable aqueous solvent system such as THF—H$_2$O or MeOH—H$_2$O to give, after acidification and work-up (6). Intermediate (6) is treated in a fourth step with a suitable sulfonating reagent such as toluenesulfonyl chloride, benzenesulfonyl chloride or methanesulfonyl chloride in the presence of a suitable base such as pyridine or triethylamine and a suitable catalyst such as LiBr or LiI in a suitable solvent system comprised of toluene and/or ethyl acetate and/or THF or related solvents to give, after work-up and isolation, the desired S-arylsulfonyl or S-alkylsulfonyl derivatives (2).

SPECIFIC EXAMPLES

Procedure I

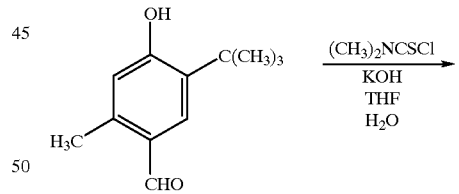

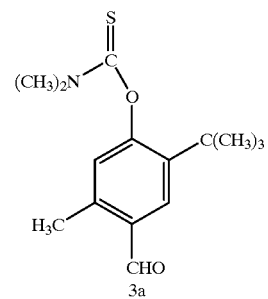

Dimethylthiocarbamic acid O-(2-tert-Butyl-4-formyl-5-methylphenyl) Ester (3a)

To a solution of 5-tert-butyl-4-hydroxy-2-methylbenzaldehyde (33.7 Kg, 162 mol correcting for a GC purity of 92.5%) in water (60 L) and THF (45 L) under a nitrogen atmosphere was added potassium hydroxide (5.0 Kg of a 45% aqueous solution) to adjust the pH of the solution to pH 12. The resulting solution was stirred at 10–19° C. while a solution of dimethylthiocarbamoyl chloride (28.7 Kg) in THF (36 L) was added over a 2.5 hour period with simultaneous addition of 45% KOH (22.2 Kg) in order to hold the pH of the reaction mixture between 11.8 and 12.1. The vessel containing the dimethylthiocarbamoyl-THF solution was rinsed with THF (5 L) and the rinse combined with the whole. Additional 45% KOH (3.8 Kg) was added to the mixture over a 2 hour period at 15–19° C. in order to maintain a basic pH in the range 11.7–11.8. Stirring at 18–19° C. was continued for another 70 minutes. Ethyl acetate (45 Kg) and heptane (34 Kg) were added to the reaction mixture. Phase separation was assisted by the addition of NaCl (22 Kg) in water (60 L). After separation the aqueous layer was extracted with a solution of ethyl acetate (23 Kg) and heptane (17 Kg). The combined organic layers were diluted with ethyl acetate (50 Kg) and extracted with 10% KOH (2×35 L) followed by 10% aqueous sodium chloride solution (2×33 Kg). The organic product solution was concentrated to a volume of approximately 45 L. This was treated with 45% KOH (50 gm) and diluted with methanol (40 L) and the resulting solution cooled to 43° C. Water (7 L) was added over 15 to 30 minutes while maintaining the temperature between 40 and 45° C. The solution was cooled slowly with addition of dimethylthiocarbamic acid O-(2-tert-butyl-4-formyl-5-methylphenyl) ester seed crystals. Crystallization began at 40° C. The mixture was stirred and cooled over several hours to 2° C. The mixture was filtered and the solid washed with a solution of methanol (25 L) and water (6 L) followed by water (20 L) and vacuum dried at 40–45° C. overnight until the water content was 0.03%. This gave dimethylthiocarbamic acid O-(2-tert-butyl-4-formyl-5-methylphenyl) ester (3a): 34.8 Kg (125 mol, 77%): mp: 79.5–81° C.; Assay (HPLC): 100.0 area %; ROI: 0.03%.

Dimethylthiocarbamic acid O-(2-tert-Butyl-4-formyl-5-methylphenyl) Ester (3a)

Potassium hydroxide (80 mL of a 10% aqueous solution) was added to a mixture of 5-tert-butyl-4-hydroxy-2-methylbenzaldehyde (99.0 g, 515 mmol) in water (180 mL) and THF (135 mL). This mixture was stirred at room temperature and a solution of dimethylthiocarbamoyl chloride (86.1 g) in THF (108 mL) added slowly over a 2 hour period with simultaneous addition of 10% KOH in order to hold the pH of the reaction mixture between 12.0 and 12.3. After approximately 70% of the dimethylthiocarbamoyl chloride-THF solution had been added, vacuum was applied to the reaction mixture to remove THF solvent and thus increase the rate of the bimolecular reaction. During the distillation, the simultaneous additions of 10% KOH and the dimethylthiocarbamoyl chloride-THF solution were continued while maintaining the pH range between 12.0 and 11.6 and the reaction temperature between 23–25° C. The distillation was continued for 10 minutes after all the dimethylthiocarbamoyl chloride-THF solution had been added and then stopped. Stirring at ambient pressure and temperature was continued for another 90 minutes. During this time the pH was stable between 11.6 and 11.75. A solution of ethyl acetate (150 mL) and heptane (150 mL) was added to the reaction mixture and after stirring and settling the layers were separated and the aqueous layer extracted with 1:1 heptane/ethyl acetate (150 mL). The combined organic extracts were extracted with 10% KOH (2×105 mL) and water (2×90 mL) and concentrated to an oil (210 gm). This was diluted with methanol (120 mL). The solution was warmed to 45° C. and water (20 mL) added. The solution was cooled to 25° C. and 50% NaOH (170 mg) was added. The resulting solution was concentrated to an oil (160 gm). This was redissolved in methanol (120 mL) at 50° C. and water (15 mL) added. The solution was cooled slowly with addition of dimethylthiocarbamic acid O-(2-tert-butyl-4-formyl-5-methylphenyl) ester seed crystals. Crystallization began at 43° C. The mixture was stirred and cooled over several hours to −5° C. The mixture was filtered and the solid washed with 4:1 methanol/water (75 mL) and vacuum dried at 40° C. overnight to give dimethylthiocarbamnic acid O-(2-tert-butyl-4-formyl-5-methylphenyl) ester (3a): 121.5 g (435 mmol, 84%): mp: 80–81° C.; assay (HPLC): 99.7 area %.

Procedure II

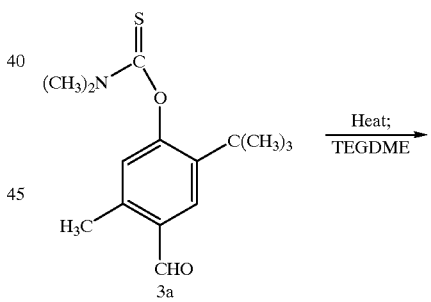

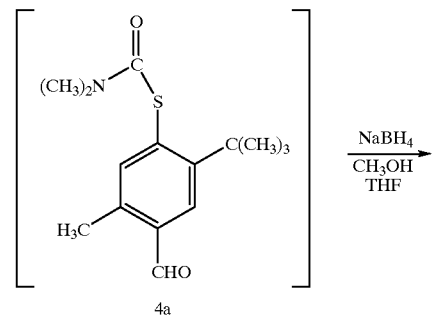

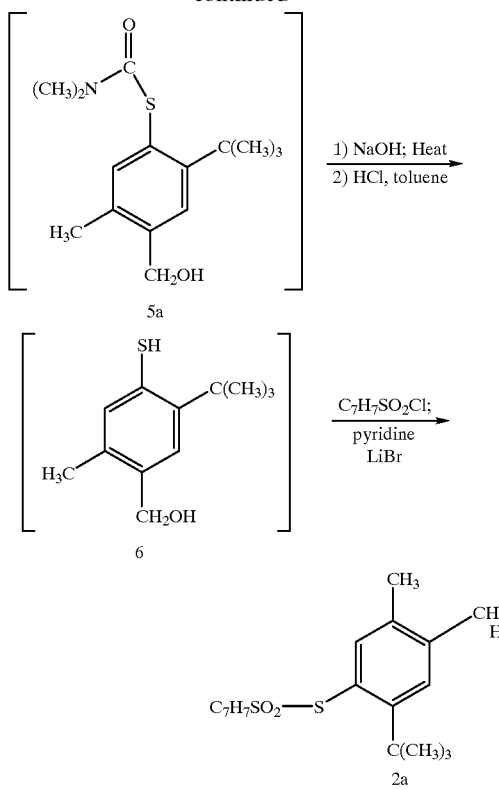

Toluene-4-thiosulfonic Acid S-(2-tert-Butyl-4-hydroxymethyl-5-methyl-phenyl) Ester (2a)

Dimethylthiocarbamic acid O-(2-tert-butyl-4-formyl-5-methylphenyl) ester (3a) (24.0 g, 85.9 mmol) was treated with tetraethylene glycol dimethyl ether (65 g) and the mixture stirred and heated under an argon atmosphere to 275° C. where the solution was maintained for 30 minutes. The solution was cooled and water (250 mL) was added to give a precipitate. The mixture was cooled to 0° C. and filtered and the solid washed with water to give dimethylthiocarbamic acid S-(2-tert-butyl-4-formyl-5-methylphenyl) ester (4a) as a water wet solid (35.2 g). (4a) (35.2 g) was treated with methanol (40 mL) and THF (30 mL) followed by slow addition over 20 minutes of NaBH$_4$ (14.1 g of a 12 weight percent solution in 14 M aqueous sodium hydroxide) while maintaining the temperature below 8° C. The resulting solution was allowed to stir at 20–25° C. for 80 minutes. Sodium hydroxide 50% aqueous solution (4 g) was added and the mixture heated to reflux where it was maintained for 3 hours. The solution was cooled to 20° C. and water (110 mL) and toluene (70 mL) and acidified with 37% hydrochloric acid (26 g) to pH 4.0. The aqueous layer was separated and extracted with toluene (2×15 mL). The combined toluene extracts containing 2-tert-butyl-4-hydroxymethyl-5-methylthiophenol (6) were treated with pyridine (6.12 g) and the resulting toluene solution slowly added over 3 hours at 40° C. to a prestirred (1 hour) solution of toluenesulfonyl chloride (16.6 gm) and lithium bromide (8.0 gm) in THF (75 mL). The resulting mixture was allowed to stir at 40° C. for 2 hours and then overnight at room temperature. Water (70 mL) and ethyl acetate (30 mL) were added. After mixing and settling the layers were separated and the organic layer extracted with 10% HCl (2×50 mL) followed by water (50 mL). The organic layer was concentrated under vacuum to a weight of 45 g which was warmed to 60° C. Heptane (20 mL) was added slowly resulting in a precipitate. The mixture was stirred and cooled to 10° C. The mixture was filtered and the product washed with 1:1 toluene/heptane (40 mL) and vacuum dried at 40° C. to give toluene-4-thiosulfonic acid S-(2-tert-butyl-4-hydroxymethyl-5-methylphenyl)ester (2a) (19.4 gm, 53.2 mmol, 62% yield for the 4 steps): mp: 121–122° C.; Assay (HPLC): 96.3 area %.

Dimethylthiocarbamic Acid S-(2-tert-Butyl-4-formyl-5-methylphenyl) Ester (4a)

Dimethylthiocarbamic acid O-(2-tert-butyl-4-formyl-5-methylphenyl) ester (3a) (100 gm, 358 mmol) was treated with tetraethylene glycol dimethyl ether (66.7 gm) and the mixture stirred and heated under an argon atmosphere to 250° C. where it was maintained for 2 hours. The solution was stirred and cooled to 25° C. and methanol (500 mL) was added. The resulting solution was slowly added to water (500 mL) at 0–5° C. The mixture was stirred for 1 hour and filtered and the solid washed with water (200 mL) and vacuum dried overnight at 40–50° C. to give crude dimethylthiocarbamic acid S-(2-tert-butyl-4-formyl-5-methylphenyl) ester (4a). This was recrystallized from toluene (40 mL) and heptane (100 mL) and the product vacuum dried at 50° C. to give dimethylthiocarbamic acid S-(2-tert-butyl-4-formyl-5-methylphenyl) ester (4a): (50.0 gm, 179 mmol, 50%): mp: 107–108° C.; HPLC: 97.6%.

Dimethylthiocarbamic Acid S-(2-tert-Butyl-4-hydroxymethyl-5-methyl-phenyl) Ester (5a)

Dimethylthiocarbamic acid S-(2-tert-butyl-4-formyl-5-methylphenyl) ester (4a) (6.0 gm, 21 mmol) was dissolved in THF and treated with lithium borohydride (0.8 gm) in portions. The mixture was cooled in an ice bath and stirring continued for 1.5 hours. Toluene (25 mL) and water (10 mL) were added followed by cautious addition of 37% hydrochloric acid (2.8 gm) to destroy excess borohydride and adjust the pH to 6.5. The aqueous layer was separated and the organic layer extracted with 1 N NaOH (2×10 mL) and water (10 mL) and concentrated to a solid. This was recrystallized from toluene and heptane and the crystals vacuum dried at 40° C. to give dimethylthiocarbamic acid S-(2-tert-butyl-4-hydroxymethyl-5-methylphenyl) ester (5a) (5.6 gm): mp: 135.9–136.4° C.; HPLC: 99.1%.

A Process for the Preparation of (+/−)-3-[2-(4-N-Protectedaminophenyl)ethyl]-3-hydroxy-4-methylpentanoic acid derivatives (+/−)-3-[2-(4-N-Protectedaminophenyl)ethyl]-3-hydroxy-4-methylpentanoic acids (11) are key intermediates required for the synthesis of (S)-6-[2-(4-amino-phenyl)-ethyl]-3-(2-tert-butyl-4-hydroxymethyl-5-methyl-phenylsulfanyl)-4-hydroxy-6-isopropyl-5,6-dihydro-pyran-2-one and related dihydropyrone HIV protease inhibitors.

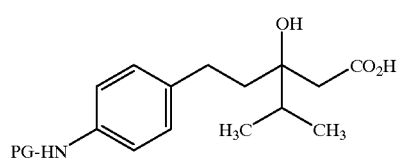

11

Disclosed here are two efficient, high yield methods for the preparation of racemic 3-[2-(N-protectedaminophenyl)

ethyl]-3-hydroxy-4-methylpentanoic acid derivatives (11) starting with readily available and inexpensive raw materials including p-nitrobenzaldehyde, methyl isobutyrylacetate and benzyl acetate. Both of these methods are six step procedures and both begin with a Schopf reaction of p-nitrobenzaldehyde with isobutyrylacetic acid to produce (+/−)-1-hydroxy-4-methyl-1-(4-nitrophenyl)pentan-3-one (12) using a method closely related to a procedure described previously for related compounds by Grayson and Tuite (*J. Chem. Soc. Perkin I,* 2137 (1986)). In both processes described below, five additional steps are required to convert (12) into the required (+/−)-3-[2-(4-N-protectedaminophenyl)ethyl]-3-hydroxy-4-methylpentanoic acids derivative (11).

General Description of the Process: Procedure I

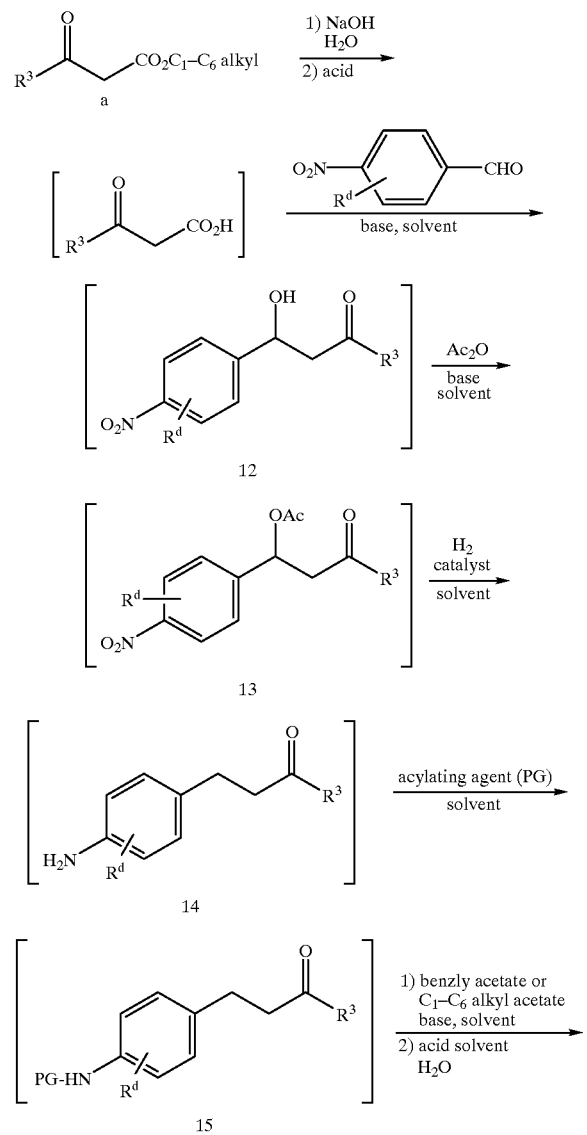

wherein $R^3$ is $C_1$–$C_6$ alkyl or $C_2$–$C_8$ cycloalkyl, $R^d$ is hydrogen, halogen, or $C_1$–$C_6$ alkyl,

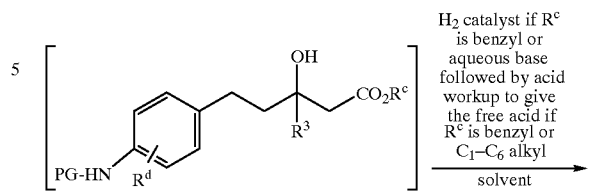

wherein $R^c$ is benzyl or $C_1$–$C_6$ alkyl

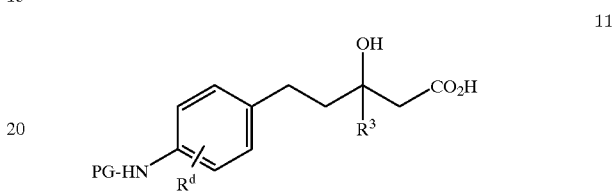

p-Nitrobenzaldehyde is allowed to react with (a) (c.f., Grayson and Tuite, *J. Chem. Soc. Perkin I,* 2137 (1986)) in a suitable solvent (such as methyl tert-butyl ether or the reaction may be run without solvent) in the presence of a suitable base such as pyridine, to provide after work-up (12) as a solution in a mixture of the base (e.g., pyridine) and solvent (e.g., methyl tert-butyl ether and/or toluene). This solution containing (12) is treated with acetic anhydride in order to form the acetate derivative of (12) namely (13). Following work-up involving extraction with aqueous acid (e.g., HCl) to remove the base (e.g., pyridine), there is obtained a solution of (13) in solvent. The latter is diluted with a suitable water miscible solvent such as THF and the whole subjected to hydrogenation over a suitable catalyst such as palladium to produce after work-up by filtration to remove catalyst, a solution of (14) in solvent. The solution of (14) in a suitable solvent (e.g., toluene) is treated with a suitable acylating reagent such as acetic anhydride, formic acetic anhydride, methyl formate, ethyl chloroformate, benzyl chloroformate, isobutyl chloroformate, etc. (if necessary in some cases a suitable base such as pyridine, triethylamine, sodium carbonate, etc. may be included), in order to form after work-up (to remove salts, excess acylating reagent and/or base, and solvent), the N-protected derivative of (14), (15). A solution of (15) in a suitable polar, aprotic solvent such as THF is added at low temperature (−30 to −80° C.) to a solution of an excess (24 equivalents) of the lithium enolate anion derivative of benzyl acetate (prepared from benzyl acetate and a suitable base such as lithium diisopropylamide) in a suitable aprotic solvent system such as THF or THF-hexanes. Following quench of this reaction mixture using a suitable acid such as acetic acid and extraction into a suitable solvent system (such as toluene or toluene-ethyl acetate), a solution of (16) is obtained. The latter is debenzylated by base induced saponification of the ester function or alternatively by hydrogenolysis of the benzyl ester over a suitable catalyst (e.g., palladium) which affords after work-up and isolation, the desired derivative (11).

SPECIFIC EXAMPLES

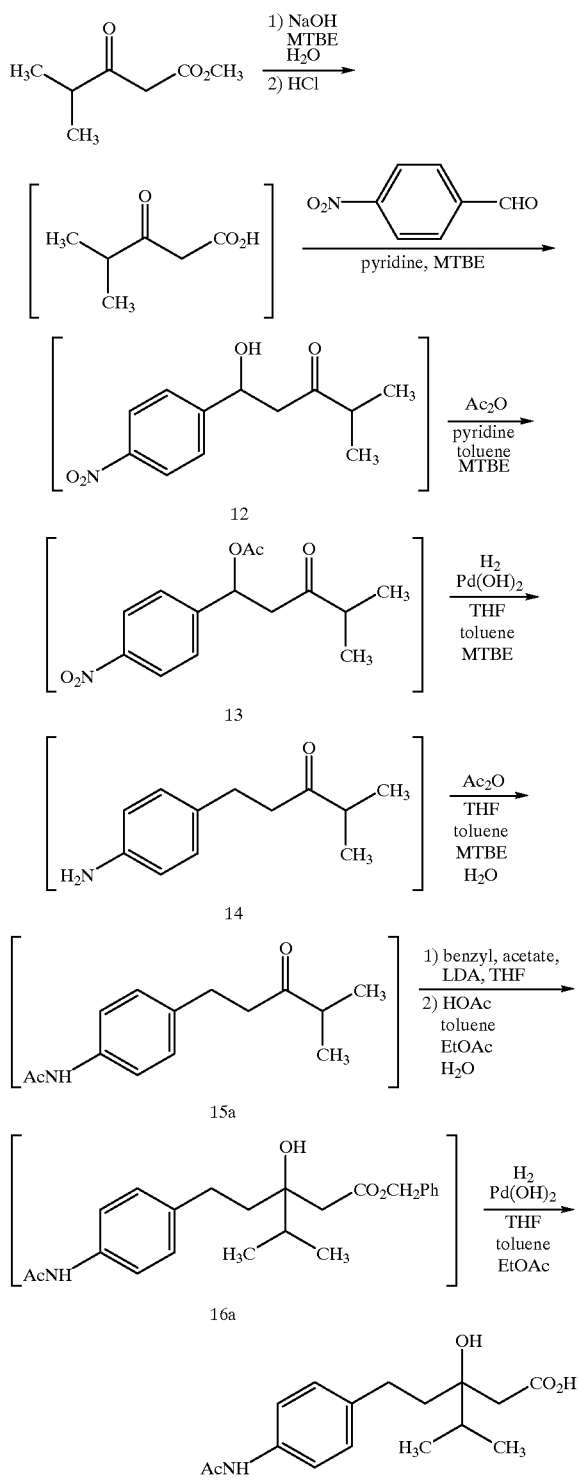

(+/−)-3-[2-(4-Acetylaminophenyl)ethyl]-3-hydroxy-4-methylpentanoic Acid (11a)

Methyl isobutyrylacetate (40.0 Kg), methyl tert-butyl ether (10 L) and water (60 L) were charged to a still under an inert atmosphere and the mixture stirred and cooled to 17° C. Sodium hydroxide (60 Kg of a 50% aqueous solution) was added over 2 hours while maintaining the temperature between 18 and 25° C. The mixture was stirred overnight at 22–35° C. and then cooled to 1° C. Hydrochloric acid (77 Kg of a 37% aqueous solution) was added while maintaining the temperature below 10° C. to adjust the pH to 0.2. After settling the aqueous layer was separated and treated with sodium chloride (5 Kg) and extracted with methyl tert-butyl ether (5 L). The combined organic layers were added to a mixture of p-nitrobenzaldehyde (26.0 Kg, 172 mmol) and pyridine (49 Kg) over 35 minutes while maintaining the temperature between 1 and −4° C. The resulting mixture was stirred overnight at 2–3° C. and then warmed to 30–35° C. where it was held for 3.5 hours. Toluene (60 L) was charged to the mixture which was then cooled to 8° C. and extracted with a solution of sodium carbonate (3 Kg) in water (30 L) followed by a solution of sodium chloride (12 Kg) in water (30 L). The remaining organic layer was dried over sodium carbonate (10 Kg). After filtration to remove the sodium carbonate, the carbonate salt was washed with toluene (60 L) and the wash combined with the filtrate to provide a solution of (+/−)-1-hydroxy-4-methyl-1-(4-nitrophenyl)pentan-3-one (12) in toluene, pyridine and methyl tert-butyl ether. This was cooled to 0° C. and acetic anhydride (33.0 Kg) added over 40 minutes while maintaining the temperature between 0 and −2° C. The resulting mixture was stirred overnight while maintaining the temperature between 2 and 3° C. Water (80 L) was added with stirring. After settling, the aqueous layer was separated and the organic layer extracted twice with a solution 37% hydrochloric acid (22 Kg) and water (50 L) while including 10 L of toluene to aid in transfer of the organic solution of the product. The latter was extracted with water (40 L) to give a solution of (+/−)-1-acetoxy-4-methyl-1-(4-nitrophenyl)pentan-3-one (13) in toluene and methyl tert-butyl ether. This solution was added to 4.4 Kg of 20% palladium hydroxide on carbon, 50% water wet, in tetrahydrofuran (50 L) and toluene (40 L) and the mixture hydrogenated at 14–25° C. under 50 psi hydrogen gas. The mixture was filtered to remove catalyst and the catalyst washed with toluene (30 L) and this combined with the whole. The resulting solution containing 1-(4-aminophenyl)-4-methylpentan-3-one (14) was cooled to 3° C. and treated with acetic anhydride (24.0 Kg) while holding the temperature below 20° C. This solution was stirred overnight at 15–20° C. 4-Dimethylaminopyridine (0.4 Kg) and water (4 L) were added and the resulting solution distilled under vacuum to a volume of 190–200° F. The remaining solution was cooled to 2° C. and extracted with a solution of 26 Kg 50% sodium hydroxide in 58 L water followed by extraction with a solution of 13 Kg 50% sodium hydroxide in 29 L water, a solution of 7 Kg 37% hydrochloric acid in 15 L water and finally a solution of 12 Kg sodium chloride in 30 L water. The remaining organic layer was concentrated under vacuum to remove solvent while holding the batch temperature below 53° C. The residue was dissolved in tetrahydrofuran (155 L) to give 172 Kg of a solution of 1-(4-N-acetylaminophenyl)-4-methylpentan-3-one (15a) in THF. A solution of the lithium enolate anion of benzyl acetate was prepared starting with 29.0 Kg diisopropylamine in 350 L THF followed by treatment of this solution with 20.7 Kg of 10 m n-butyl lithium in hexanes at −9 to −35° C. followed by addition of 40.0 Kg benzyl acetate to the resulting solution of lithium diisopropylamide at −63 to −69° C. A 86.8 Kg portion of the solution of 15a in THF was added to this lithium enolate of benzyl acetate over a 1.5 hour period at −56 to −70° C. After stirring an additional 15–20 minutes at −52 to −56° C., the mixture was quenched by addition to a cold (0–5° C.) solution of toluene (43 L), ethyl acetate (43 L), acetic acid (34 L), and water (65 L) while holding the temperature below 5° C. The low temperature reaction vessel was rinsed with tetrahydrofuran (5 L) and the rinse added to the quench solution. After mixing, the solution was allowed to settle and the aqueous layer separated and discarded. This provides a solution of (+/−)-3-[2-(N-acetylaminophenyl)ethyl]-3-hydroxy-4-methylpentanoic acid benzyl ester (16a) in toluene, THF, and ethyl acetate. In a similar way a second part lot of (16a) was prepared using the remaining amount (85.1 Kg) of 15a in THF by addition to the lithium enolate anion of benzyl acetate (prepared from 29.0 Kg diisopropylamine in 350 L THF followed by treatment with 20.0 Kg of 10 M n-butyl lithium in hexanes followed by addition of 40.0 Kg benzyl acetate) and finally quenching into (43 L), ethyl acetate (43 L), acetic acid (34 L), and water (65 L) and separation of the aqueous layer. The combined part lots of 16a in toluene, THF and ethyl acetate were extracted with a solution of acetic acid (8 Kg) in water (110 L) followed by extraction with water (65 L). The remaining organic layer was concentrated under vacuum at 25–30° C. to 200–220° L and then added to 4.0 Kg of 20% palladium hydroxide on carbon, 50% water wet, in tetrahydrofuran (30 L), and toluene (30 L) and the mixture hydrogenated at 18–24° C. under 50 psi hydrogen gas. The mixture was filtered to remove the catalyst and the catalyst washed with tetrahydrofuran (40 L) and this combined with the whole which was then cooled to 6° C. The resulting solution was extracted with three separate portions of a solution of 45% potassium hydroxide (23 Kg) dissolved in water (64 L). The combined basic extracts were back extracted with toluene (30 L) and then treated with ethyl acetate (80 L). This ethyl acetate/aqueous KOH solution was acidified to pH 4.2 using 42.7 Kg of 37% hydrochloric acid while holding the temperature below 20° C. The layers were separated and the aqueous layer extracted with ethyl acetate (80 L). The combined ethyl acetate extracts were washed with water (30 L) and concentrated under vacuum to about 55 L while maintaining the temperature below 25° C. Additional ethyl acetate (13 Kg) was added back to the thick slurry of the product to assist agitation. The mixture was stirred and cooled overnight to 20° C. and filtered on a centrifuge. The product was washed with ethyl acetate (40 L and 10 L) and vacuum dried at 20–42° C. until the LOD was less than 0.5%. This gave 34.9 Kg (119 mmol, 69% yield for the six steps) of (+/−)-3-[2-N-acetylaminophenyl)ethyl]-3-hydroxy-4-methylpentanoic acid (11a): mp: 158–162° C.; Assay (HPLC): 98.8 area %; ROI: 0.07%.

Purification of (+/−)-1-Hydroxy-4-methyl-1-(4-nitrophenyl)pentan-3-one (12)

A portion of the (+/−)-1-hydroxy-4-methyl-1-(4-nitrophenyl)pentan-3-one (12) solution in toluene, pyridine and methyl tert-butyl ether was concentrated to a solid. This was recrystallized from toluene and heptane to give (+/−)-1-hydroxy-4-methyl-1-(4-nitrophenyl)pentan-3-one (12): mp: 64–65° C.; HPLC: 99.2 area %.

Purification of (+/−)-1-Acetoxy-4-methyl-1-(4-nitrophenyl)pentan-3-one (13)

A portion of the (+/−)-1-acetoxy-4-methyl-1-(4-nitrophenyl)pentan-3-one (13) solution in toluene and methyl tert-butyl ether was concentrated to an oil. On standing, crystals were formed. A portion of these crystals were recrystallized from toluene and heptane to give (+/−)-1-acetoxy-4-methyl-1-(4-nitrophenyl)pentan-3-one (13): mp: 54–55° C.; HPLC: 99.6 area %.

Purification of 1-(4-N-Acetylaminophenyl)-4-methylpentan-3-one (15a)

Crude 1-(4-N-acetylaminophenyl)-4-methylpentan-3-one (15a) was recrystallized form ether followed by recrystallization from ether and heptane: mp: 76–77° C.; HPLC: 97.2 area %.

General Description of the Process: Procedure II

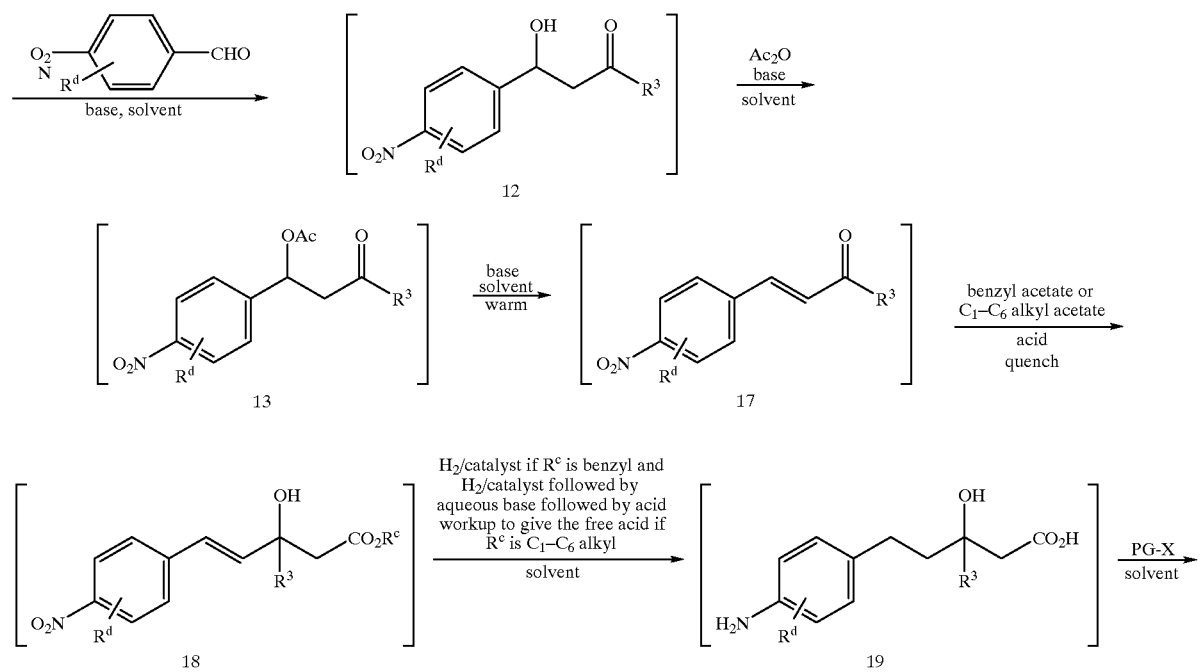

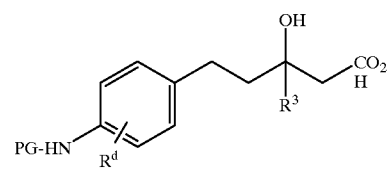

p-Nitrobenzaldehyde is allowed to react with (a) (c.f., Grayson and Tuite, *J. Chem. Soc. Perkin I*, 2137 (1986)) in a suitable solvent (e.g., methyl tert-butyl ether or related solvent; the reaction may also be run without solvent) in the presence of a suitable base such as pyridine, to provide after work-up (12) as a solution in a mixture of the base (e.g., pyridine) and solvent (e.g., methyl tert-butyl ether and/or toluene). This solution containing (12) is treated with acetic anhydride in order to form the acetate derivative of (12), namely (13). The resulting mixture is then heated to 50–90° C. to induce elimination of acetic acid. This leads to formation of (17). After work-up involving extraction with aqueous acid (e.g., HCl) to remove the base (e.g., pyridine) followed by concentration under vacuum of the organic layer to remove solvent, (17) is obtained as a solid. The crude unsaturated ketone, (17) is dissolved in a suitable aprotic solvent such as tetrahydrofuran and the resulting solution added at low temperature (−30 to −80° C.) to a solution of an excess (1.05–1.5 equivalents) of the lithium enolate anion derivative of benzyl acetate (prepared from benzyl acetate and a suitable base such as lithium diisopropylamide) in a suitable aprotic solvent system such as THF or THF-hexanes. Following quench using a suitable acid (e.g., acetic acid), a solution of (18) in solvent is obtained. The latter may be diluted with a suitable protic solvent (e.g., methanol) and then hydrogenated over a suitable catalyst (e.g., palladium) thus providing (after filtration to remove the catalyst) a solution of (19). This is then treated with a suitable acylating reagent such as acetic anhydride, formic acetic anhydride, methyl formate or ethyl chloroformate (if necessary in some cases a suitable base such as pyridine, triethylamine, or sodium carbonate may be added) in order to form after work-up (to remove salts, excess acylating reagent and/or base, excess solvent) and isolation the desired N protected derivative of (18), namely (11).

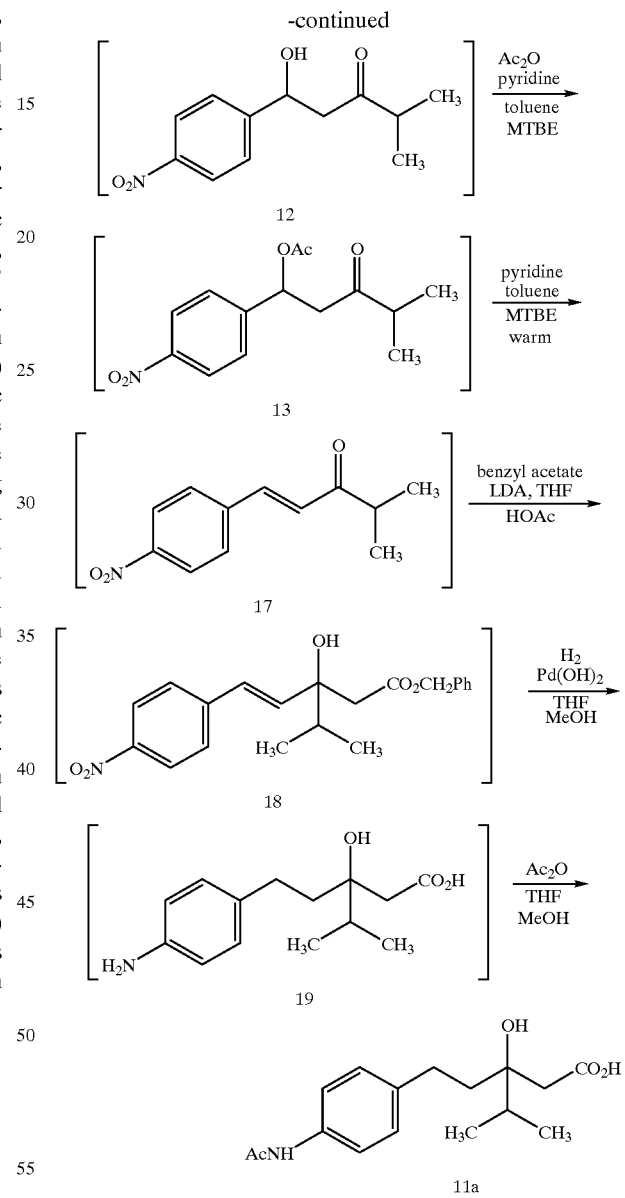

SPECIFIC EXAMPLES

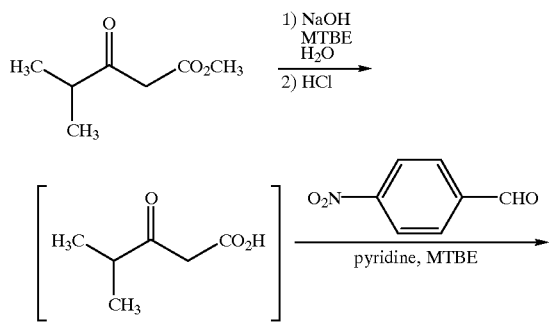

(+/−)-3-[2-(4-Acetylaminophenyl)ethyl]-3-hydroxy-4-methylpentanoic Acid (11a)

Methyl isobutyrylacetate (40.0 Kg), methyl tert-butyl ether (10 L) and water (60 L) were charged to a still under an inert atmosphere and the mixture stirred and cooled to 17° C. Sodium hydroxide (60 Kg of a 50% aqueous solution) was added over 2 hours while maintaining the temperature between 17 and 25° C. The mixture was stirred overnight at 24–25° C. and then cooled to 0° C. Hydrochloric acid (75 Kg of a 37% aqueous solution) was added while maintaining the temperature below 5° C. to adjust the pH to 0.9. After settling, the aqueous layer was separated and treated with sodium chloride (3 Kg) and extracted with methyl tert-butyl ether (5 L). The combined organic layers were added to a mixture of E-nitrobenzaldehyde (26.0 Kg, 172 mmol) and pyridine (51 Kg) over 2.5 hours while maintaining the temperature between 2 and −4° C. The resulting mixture was stirred over the weekend at −1 to 4° C. and then warmed to 30–35° C. where it was held for 5 hours. Toluene (60 L) was charged to the mixture which was then cooled to 15° C. and extracted with a solution of sodium carbonate (3 Kg) in water (30 L) followed by a solution of sodium chloride (12 Kg) in water (30 L). The remaining organic layer was dried over sodium carbonate (10 Kg). After filtration to remove the sodium carbonate, the salt was washed with toluene (60 L) and the wash combined with the filtrate to provide a solution of (+/−)-1-hydroxy-4-methyl-1-(4-nitrophenyl) pentan-3-one (12) in toluene, pyridine and methyl tert-butyl ether. This was cooled to 0° C. and acetic anhydride (33.0 Kg) added over 45 minutes while maintaining the temperature between 2 and −1° C. The resulting mixture was stirred overnight while maintaining the temperature between 2 and 1° C. thus providing a solution of (+/−)-1-acetoxy-4-methyl-1-(4-nitrophenyl)pentan-3-one (13) in toluene and methyl tert-butyl ether and pyridine. This was heated to 85–88° C. where it was held for 6 hours. After cooling to 15° C., water (40 L) was added with stirring. After settling, the aqueous layer was separated and the organic layer was extracted with a solution 37% hydrochloric acid (39 Kg) and water (75 L) while including a 10 L toluene rinse to aid in transfer of the organic solution of the product. The latter was treated with 37% hydrochloric acid (13 Kg), water (55 L), toluene (10 L), ADP carbon (4 Kg) and Supercel Hyflo (12 Kg). After stirring the mixture was filtered and the residue rinsed with toluene (30 L). The combined filtrate and rinse were allowed to settle and the aqueous layer separated from the organic layer. The latter was extracted with water (25 L) and concentrated under vacuum to remove solvent. This provides (E)-4-methyl-1-(4-nitrophenyl)-1-penten-3-one (17) as a solid. The 17 was dissolved in tetrahydrofuran (75 L). A solution of the lithium enolate anion of benzyl acetate was prepared starting with 21.0 Kg diisopropylamine in 65 L THF followed by treatment of this solution with 15.4 Kg 10 M n-butyl lithium in hexanes at −10 to −38° C. followed by addition of 28.8 Kg benzyl acetate to the resulting solution of lithium diisopropylamide at −61 to −70° C. The solution of 17 in THF was added to this benzyl acetate enolate anion solution over an 80 minute period while maintaining the temperature between −61 to −69° C. The mixture was stirred another 50 minutes at −61 to −63° C. and acetic acid (19 Kg) was added while maintaining the temperature between −57 to −64° C. Methanol (61 L) was added and the mixture stirred and warmed to 17° C. The mixture was treated with ADP carbon (8 Kg) and Supercel Hyflo (8 Kg) and diluted with THF (20 L) and methanol (20 L). The resulting mixture was stirred I hour at 20–30° C. and then concentrated under vacuum to a volume of 250–280 L. The mixture was filtered and the residue washed with a mixture of THF (50 L) and methanol (40 L). The combined filtrates containing (+/−)-3-hydroxy-3-isopropyl-5-(4-nitrophenyl)-4-pentenoic acid benzyl ester (18) in methanol-THF solvent were hydrogenated over 5.5 Kg 20% palladium hydroxide catalyst 50% water wet at 26–37° C. under 50 psi hydrogen gas. The hydrogenation mixture was filtered to remove catalyst and the catalyst washed with methanol (40 L) and this combined with the whole to give a solution of (+/−)-3-[2-(4-aminophenyl)ethyl]-3-hydroxy-4-methylpentanoic acid (19) in THF and methanol. The latter was cooled to 3° C. and acetic anhydride (25.0 Kg) added over 30 minutes while maintaining the temperature below 16° C. The resulting solution was concentrated under vacuum to remove solvent and the residue treated with toluene (20 L), methyl tert-butyl ether (10 L) and water (150 L). Sodium hydroxide 50% aqueous solution (34.6 Kg) was added to adjust the pH to 12.1 while maintaining the temperature below 19° C. The resulting mixture was heated to 60–80° C. where it was held overnight. The mixture was cooled to 18° C. and the layers separated and the organic layer extracted with water (20 L) and then discarded. The combined aqueous layers were treated with ethyl acetate (90 L) and 37% hydrochloric acid (55.8 Kg) was added to bring the pH to 2.7 while maintaining the temperature below 16° C. The aqueous layer was separated and extracted with ethyl acetate (70 L) and then discarded. The combined ethyl acetate extracts were washed twice with a solution of 3 Kg 37% hydrochloric acid in 30 L water followed by 30 L water and then concentrated under vacuum to a volume of 50–80 L. Toluene (80 L) was charged to the still and the vacuum distillation continued to reduce the volume again to 50–80 L. Ethyl acetate (30 L) was added to the still and the mixture stirred and cooled overnight to 6° C. The mixture was filtered and the solid washed with ethyl acetate (40 L and 30 L) and vacuum dried at 35–55° C. until the LOD was less than 0.5%. This provides 28.9 Kg (98.5 mmol, 57.3%) of (+/−)-3-[2-(N-acetylaminophenyl)ethyl]-3-hydroxy-4-methylpentanoic acid (11a); mp: 160–161° C.; Assay (HPLC): 98.7 area %; ROI: 0. 18%. A second crop was isolated from the mother liquors: 1.3 Kg (4.4 mmol, 2.6%); mp: 158–160° C.; Assay (HPLC): 97.4 area %; ROI: 0.04%.

(+/−)-3-Hydroxy-3-isopropyl-5-(4-nitrophenyl)-4-pentenoic acid benzyl ester (18)

A small portion of the crude (+/−)-3-hydroxy-3-isopropyl-5-(4-nitrophenyl)-4-pentenoic acid benzyl ester (18) obtained form the above sequence was partitioned between toluene and water. The toluene solution was extracted with water and concentrated to an oil that solidified on standing. The solid was recrystallized from toluene and heptane to give (+/−)-3-hydroxy-3-isopropyl-5-(4-nitrophenyl)-4-pentenoic acid benzyl ester (18): mp: 64–65° C.; HPLC: 99.2 area %.

(+/−)-3-[2-(4-Aminophenyl)ethyl]-3-hydroxy-4-methylpentanoic acid (19)

A portion of the (+/−)-3-[2-(4-aminophenyl)ethyl]-3-hydroxy-4-methylpentanoic acid (19) solution in THF and methanol was concentrated under vacuum to remove solvent. The residue (12 g) was treated with water (8 mL) to give a solution. This was treated with methylene chloride (30 mL) and the mixture extracted with water (3×30 mL). The combined water extracts were allowed to stand in a beaker several days with slow evaporation to give crystals. These were collected, washed with water and recrystallized from methanol-water to give (+/−)-3-[2-(4-aminophenyl)-ethyl]-3-hydroxy-4-methylpentanoic acid (19).

A Process for the Resolution of (+/−)-3-[2-(4-N-Protectedaminophenyl)ethyl]-3-hydroxy-4-methylpentanoic Acid Derivatives (S)-3-[2-(4-N-Protectedaminophenyl)ethyl]-3-hydroxy-4-methylpentanoic acids (23) are key intermediates required for the synthesis of (S)-6-[2-(4-amino-phenyl)-ethyl]-3-(2- tert-butyl-4-hydroxymethyl-5-methyl-phenylsulfanyl)-4-hydroxy-6-isopropyl-5,6-dihydro-pyran-2-one and related dihydropyrone HIV protease inhibitors.

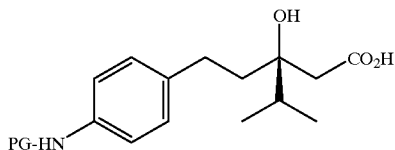

23

We report here an efficient, high yield method for resolution of racemic 3-[2-(N-protectedaminophenyl)ethyl]-3-hydroxy-4-methylpentanoic acid (11) by treatment with (S)-N-benzyl-α-methylbenzylamine (21) to form selectively the salt (22) of (S)-N-benzyl-α-methylbenzylamine with the (S) isomer of 3-[2-(4-N-protectedaminophenyl)ethyl]-3-hydroxy-4-methylpentanoic acid (23):

General Description of the Process the crystallized salts (22) by filtration followed by treatment of the salt with potassium or sodium hydroxide in water mixed with a water imiscible solvent such as toluene and subsequent separation of the aqueous and organic layers provide an aqueous solution of the corresponding alkali metal salt of the (23a). Further extraction of this aqueous solution of the alkali metal salt with a water imiscible solvent such as toluene permits removal of all or most of the (S)-N-benzyl-α-methylbenzylamine (21) resolving agent, which can be recovered for reuse in subsequent resolution runs. The remaining aqueous solution of the metal salt may then be acidified with a suitable acid such as hydrochloric acid in order to afford (23). If necessary, the latter may be purified by extraction into a suitable solvent such as ethyl acetate and the resulting solution concentrated in order to crystallize out the purified (23). Suitable protecting groups for this process may be acetyl, formyl, propionyl, benzoyl, methyl carbamoyl, ethylcarbamoyl, benzyl carbamoyl, n-butyl carbamoyl or a related nitrogen protecting group.

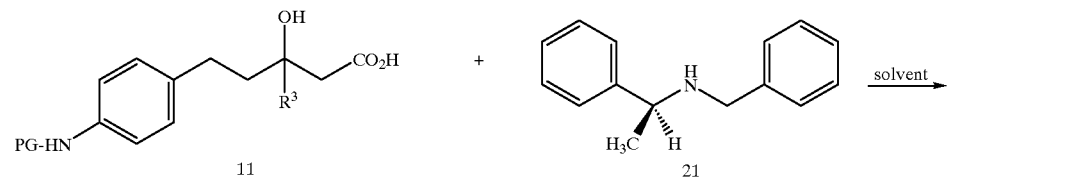

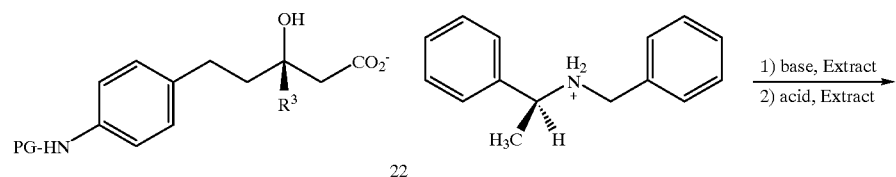

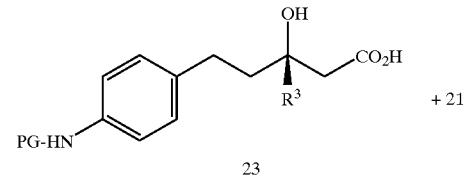

The above salts (22) may be formed by treatment of racemic (11) with 0.5 to 2 equivalents of (S)-N-benzyl-α-methylbenzylamine (21) (Becalski, Cullen, and Fryzuk, *Inorg. Chem.*, 30:5002 (1991)) at 5–50° C. in a suitable solvent such as ethanol, methanol, acetonitrile, ethyl acetate, isopropanol, tetrahydrofuran, methyl isobutyl ketone, acetonitrile, or acetone or a suitable solvent mixture including one or more of the aforementioned solvents. Isolation of

SPECIFIC EXAMPLES

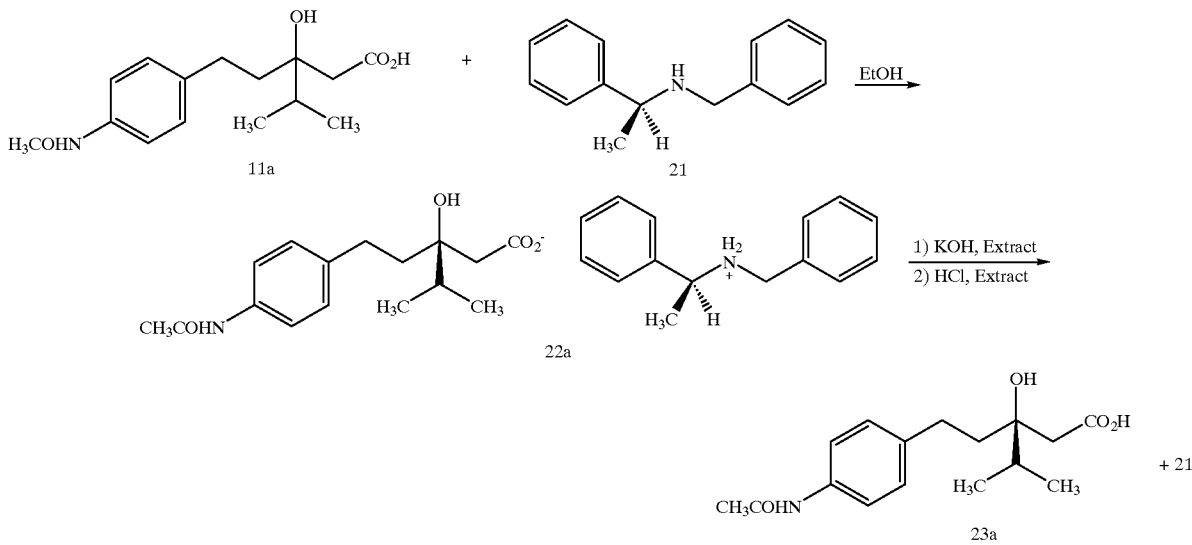

(S)-3-[2-(4-Acetylaminophenyl)ethyl]-3-hydroxy-4-methylpentanoic Acid (S)-N-Benzyl-α-methylbenzylamine Salt (22a)

Ethanol (125 g) was added to (+/−)-3-[2-(4-acetylaminophenyl)ethyl]-3-hydroxy-4-methylpentanoic acid (11a, 25 g, 85 mmol) and the resulting solution stirred at 20° C. (S)-N-Benzyl-α-methylbenzylamine (21, 22.5 g, 106 mmol) was added to the solution and the resulting mixture allowed to stir at 20° C. for 23 hours. The mixture was filtered and the product washed with ethanol (10 mL) and vacuum dried at ambient temperature to give (S)-3-[2-(4-acetylaminophenyl)ethyl]-3-hydroxy-4-methylpentanoic acid (S)-N-benzyl-α-methylbenzyl salt (22a): 18.6 g (36.8 mmol, 43% yield or 86% of theory); Chiral assay (HPLC): 99.2 area % (S) isomer 23a; mp: 152–154° C.

(S)-3-[2-(4-Acetylaminophenyl)ethyl]-3-hydroxy-4-methylpentanoic Acid (23a)

Water (60 g) and toluene (75 g) were added to (S)-3-[2-(4-acetylaminophenyl)ethyl]-3-hydroxy-4-methylpentanoic acid (S)-N-benzyl-α-methylbenzylamine salt (22a, 15 g, 30 mmol) and the pH of the resulting mixture was adjusted to 14 using 45% potassium hydroxide (5.6 mL). The mixture was stirred at ambient temperature for about 40 minutes. Agitation was stopped and the layers separated. The aqueous phase was extracted with toluene (2×20 g). Isopropyl acetate (130 g) and ethyl acetate (13 g) were added to the aqueous phase and the pH of the mixture was adjusted to 3 with 37% hydrochloric acid. The organic layer was separated from the aqueous phase and the latter extracted with ethyl acetate (15 g). The combined organic extracts were washed with saturated aqueous sodium chloride solution (25 mL). The organic product solution was heated to reflux and water removed by azeotropic distillation. When no more water was collected, the solution was distilled to afford 136 mL of distillate. The residual product mixture was stirred and cooled to ambient temperature. Stirring was continued for another 12 hours. Heptane (11 g) was added to the mixture. The slurry was cooled to 0–3° C. and held for 1 hour. The mixture was filtered and vacuum dried at 40° C. to give (S)-3-[2-(4-acetylaminophenyl)ethyl]-3-hydroxy-4-methylpentanoic acid (23a) as a white powder: 7.9 g (27 mmol, 90% yield): mp: 119–120° C.; Assay (HPLC): 99.8 area %; Chiral assay (HPLC): 98.9 area % (S) isomer; Water (KF): 0.16%.

A Process for the Preparation of N-protected (S)-6-[2-(4-aminophenyl)ethyl]-4-hydroxy-6-isopropyl-5,6-dihydropyran-2-one Derivatives N-Protected derivatives (24) of (S)-6-[2-(4-aminophenyl)ethyl]4-hydroxy-6-isopropyl-5,6-dihydropyran-2-one are key intermediates required for the synthesis of (S)-6-[2-(4-amino-phenyl)-ethyl]-3-(2-tert-butyl-4-hydroxymethyl-5-methyl-phenylsulfanyl)-4-hydroxy-6-isopropyl-5,6-dihydro-pyran-2-one and related dihydropyrone HIV protease inhibitors.

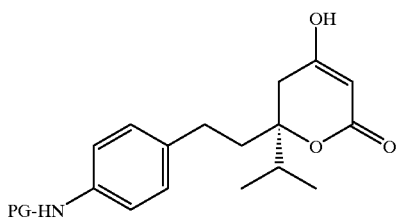

A new, high yield process is proposed here for the synthesis of (24) starting from (S)-3-[2-(N-protectedaminophenyl)ethyl]-3-hydroxy-4-methylpentanoic acid (23) derivatives using a two step procedure. The initial step is related to a process known to be useful for the conversion of carboxylic acids to β-keto esters reported initially by Masamune (*Angew. Chem. Int. Ed. Engl.*, 18:72 (1979)) but avoids the use of the relatively expensive reagent used by Masamune, namely the magnesium salt of malonic acid mono ethyl ester. In the new process presented here we find that the required (and relatively unstable) γ-hydroxy-β-keto ester intermediate (26) can be generated in high yield by reacting (23) with carbonyl diimidazole in order to activate the carboxylic acid function and give (25), followed by treatment of (25) with a complex obtained from the inexpensive reagents, potassium ethyl malonate and magnesium chloride. Once formed (26) is converted directly, without isolation, into the desired pyrone derivatives (24) using sodium or potassium hydroxide followed by acid work-up. Suitable nitrogen protecting groups for this process include: acetyl, formyl, propionyl, benzoyl, methyl carbamoyl, ethyl carbamoyl, benzyl carbamoyl and related nitrogen protecting groups.

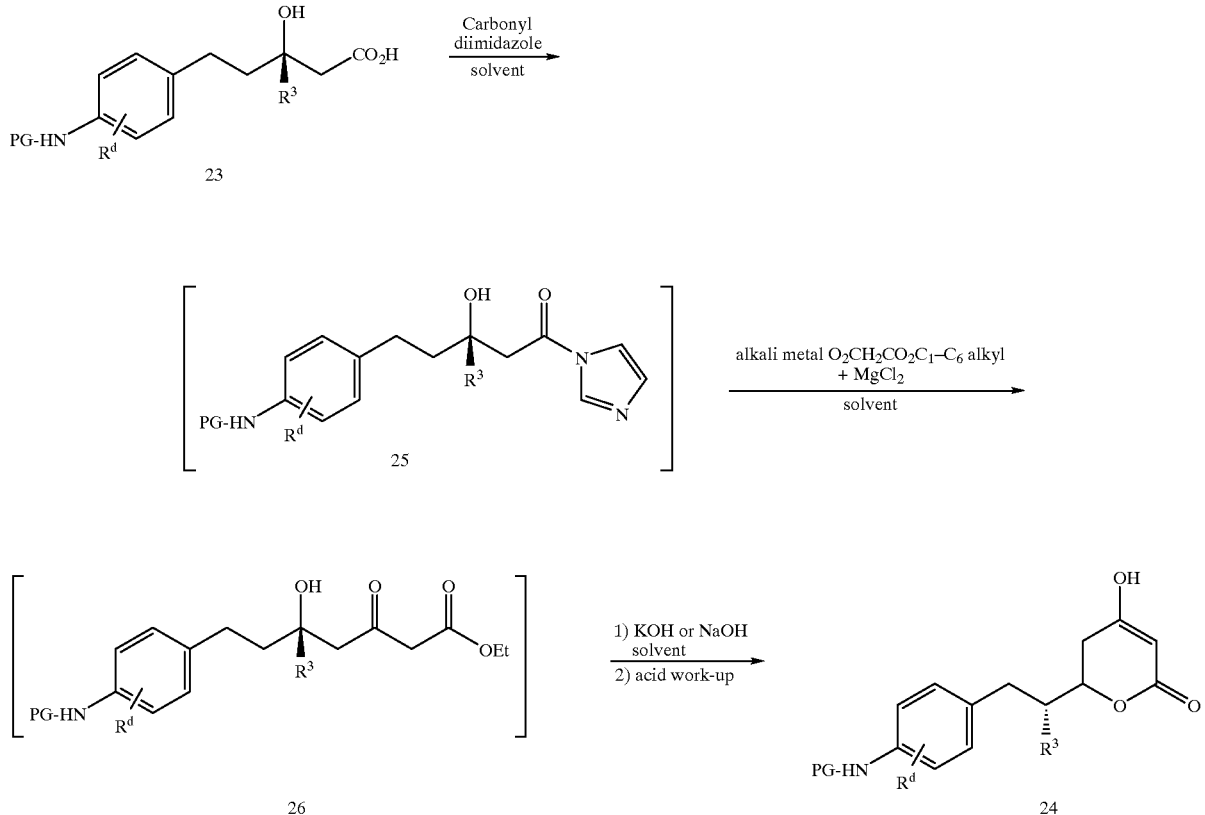

The above process provides superior yields and substantially improved economy. PG, $R^d$, and $R^3$ are as defined above.

General Description of the Process

Magnesium chloride is allowed to react with a compound of the formula

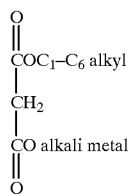

in a suitable polar, aprotic solvent system such as acetonitrile or acetonitrile-THF to generate a magnesium complex of malonic acid mono $C_1$–$C_6$ alkyl ester. In a separate reactor a solution of the required acyl imidazolide (25) is prepared by adding carbonyl diimidazole to the corresponding carboxylic acid (23) in a suitable polar, aprotic solvent such as THF. The latter solution is then added to the magnesium complex of malonic acid mono ethyl ester in the first reactor. The resulting mixture is stirred at room temperature to complete the reaction and then concentrated under vacuum to remove solvent. Work up involving acidification and extraction with a suitable acid such as hydrochloric acid followed by extraction with a suitable base such as aqueous sodium bicarbonate and concentration of the remaining organic layer provides the intermediate γ-hydroxy-β-keto ester intermediate (26). The latter is not isolated but treated directly with a suitable base such as NaOH or KOH in a suitable solvent system such as methanol or THF-water. Work-up involving extraction to remove impurities and finally acidification with a suitable acid such as acetic acid and isolation of the product gives the required derivative (24).

SPECIFIC EXAMPLES

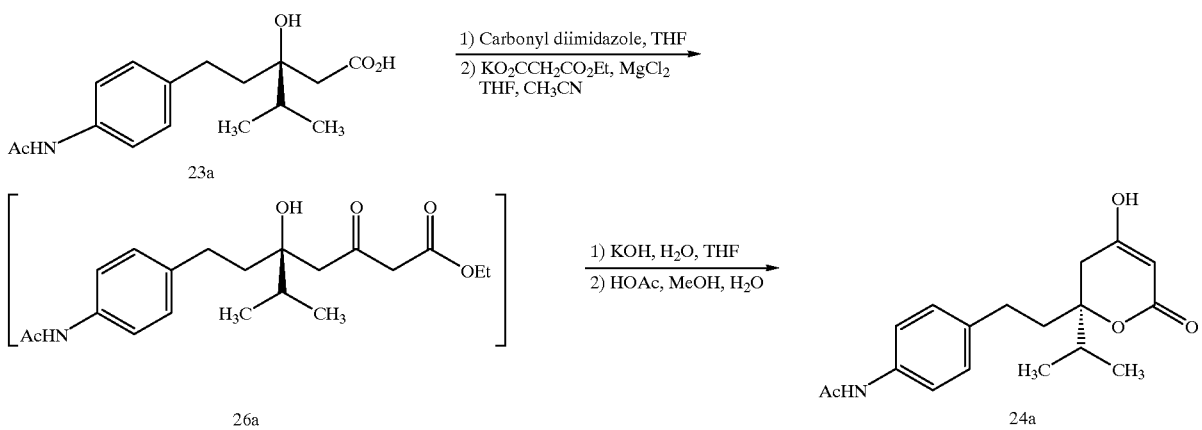

(S)-6-[2-(4-Acetylaminophenyl)ethyl]-4-hydroxy-6-isopropyl-5,6-dihydropyran-2-one (24a)

Potassium ethyl malonate (12.9 Kg) and magnesium chloride (7.6 Kg) are charged to a still under an inert atmosphere followed by acetonitrile (70 L) and tetrahydrofuran (45 L) and the resulting mixture stirred at 8–20° C. for 70 minutes followed by an additional 3.5 hours at 23–25° C. at which point the mixture is diluted with additional tetrahydrofuran (10 L). To a second reactor is added (S)-3-[2-(N-acetylaminophenyl)ethyl]-3-hydroxy-4-methylpentanoic acid (23a) (9.5 Kg, 31 mol correcting for 4.9% water content) and tetrahydrofuran (296 L) and this mixture stirred at ambient temperature. Carbonyl diimidazole (8.0 Kg) is added while maintaining the temperature below 23° C. The resulting solution is stirred at 23–26° C. for 3.5 hours and then added over a 2.5 hour period at 23–26° C. to the potassium ethyl malonate-magnesium chloride complex in the first still. The resulting mixture is stirred overnight at 22–26° C. and then concentrated under vacuum to remove solvent while maintaining the temperature below 21° C. Cold ethyl acetate (116 L) and cold water (60 L) are added to the residue followed by 37% hydrochloric acid (7 Kg) with agitation while maintaining the temperature below 10° C. The layers are allowed to settle and the aqueous layer separated. The organic layer is extracted twice with a solution of 37% hydrochloric acid (2.5 Kg) in water (22 L) followed by a solution of sodium bicarbonate (2 Kg) in water (20 L). The remaining organic layer is concentrated under vacuum to remove solvent while maintaining the batch temperature below 51° C. Tetrahydrofuran (48 L) is added to the residue and the mixture stirred and cooled to 13° C. A solution of 8.4 Kg 45% aqueous potassium hydroxide in water (59 L) is added and the resulting solution stirred at 22–26° C. for 2 days. Ethyl acetate (80 L) is added to the solution and the lower aqueous layer separated. The organic layer is extracted with a solution of 2 Kg 45% aqueous potassium hydroxide in water (15 L) and the combined aqueous extracts concentrated in the first still under vacuum to a volume of 70–85 L while maintaining the temperature below 24° C. The resulting solution is added over 1.5 hours to a solution of 3.9 Kg acetic acid in methanol (20 L) and water (35 L) in the second reactor at 23–26° C. The still is rinsed with water (8 L) and the rinse transferred to the reactor. The mixture is stirred and cooled overnight to 2° C. and filtered and the solid washed with water (80 L) and vacuum dried at 45–57° C. to give 7.6 Kg (22 mol; 71% correcting for HPLC purity and also water content) of (S)-6-[2-(4-acetylaminophenyl)ethyl]-4-hydroxy-6-isopropyl-5,6-dihydropyran-2-one (24a): Assay (HPLC): 95.4%; Water (KF): 4.7%. A small sample of (24a) was recrystallized from acetonitrile: mp: 171° C. (dec); Assay (HPLC): 99.0 area %.

(S)-6-[2-(4-Acetylaminophenyl)ethyl]-4-hydroxy-6-isopropyl-5,6-dihydropyran-2-one (24a)

Potassium ethyl malonate (12.9 g) and magnesium chloride (7.6 g) are added to a flask followed by acetonitrile (70 mL) and tetrahydrofuran (45 mL) and the resulting mixture stirred at 15° C. for 3 hours under an inert atmosphere. To a second flask is added (S)-3-[2-(N-acetylaminophenyl)ethyl]-3-hydroxy-4-methylpentanoic acid (23a) (9.6 g, 31 mmol correcting for 4.9% water content) and tetrahydrofuran (296 mL) followed by carbonyl diimidazole (8.0 g) and the resulting solution stirred at ambient temperature for 3 hours. The latter solution is then added over a 2 hour period to the potassium ethyl malonate-magnesium chloride complex in the first flask and the resulting mixture stirred overnight at 20° C. The mixture was concentrated under vacuum to remove solvent while maintaining the temperature below 40° C. Cold ethyl acetate (116 mL) and water (60 mL) are added to the residue followed by 37% hydrochloric acid (7 g) with agitation while maintaining the temperature below 10° C. The layers are allowed to settle and the aqueous layer separated. The organic layer is extracted twice with a solution of 37% hydrochloric acid (2.5 g) in water (22 mL) followed by a solution of sodium bicarbonate (2 g) in water (20 mL). The remaining organic layer is concentrated under vacuum to remove solvent. The residue is dissolved in methanol (10 mL) and a solution of sodium hydroxide pellets (3.0 g) dissolved in methanol (25 mL) is added and the resulting solution stirred at ambient temperature for 3 days. The solution was concentrated under vacuum to remove solvent. Water (60 mL) was added to the residue and then removed by concentrating under vacuum while maintaining the temperature below 45° C. The remaining oil is dissolved in water (60 mL) and the resulting solution added over 45 minutes to a solution of 3.9 g acetic acid in methanol (10 mL) and water (10 mL). The mixture is stirred overnight at ambient temperature and then cooled to 5° C. and filtered and the solid washed with water (100 mL) and vacuum dried at 60° C. to give 8.0 g (23 mmol; 74% correcting for HPLC purity and water content) of (S)-6-[2-(4-acetylaminophenyl)ethyl]-4-hydroxy-6-isopropyl-5,6-dihydropyran-2-one (24a): HPLC: 95.1 %; Water (KF): 4.4%.

Purification of (S)-5-[2-(4-Acetylaminophenyl)ethyl]-5-hydroxy-6-methyl-3-oxoheptanoic Acid Ethyl Ester (26a)

Crude (S)-5-[2-(4-acetylaminophenyl)ethyl]-5-hydroxy-6-methyl-3-oxoheptanoic acid ethyl ester (26a) may be purified by recrystallization from ethyl acetate: mp: 97–99° C.; Assay (HPLC): 99.3 area %.

A Process for the Preparation of (S)-6-[2-(4-aminophenyl)ethyl]-3-(2-tert-butyl-4-hydroxymethyl-5-methylphenylsulfanyl)-4-hydroxy-6-isopropyl-5,6-dihydropyran-2-one (S)-6-[2-(4-Aminophenyl)ethyl]-3-(2-tert-butyl-4-hydroxymethyl-5-methylphenyl-sulfanyl)-4-hydroxy-6-isopropyl-5,6-dihydropyran-2-one and related compounds have useful antiviral activity as HIV protease inhibitors. 6-[2-(4-amino-phenyl)-ethyl]-3-(2-tert-butyl-4-hydroxymethyl-5-methyl-phenylsulfanyl)-4-hydroxy-6-isopropyl-5,6-dihydro-pyran-2-one has been prepared in low yield by coupling the N-BOC protected derivative of (S)-6-[2-(4-aminophenyl)ethyl]-4-hydroxy-6-isopropyl-5,6-dihydropyran-2-one (24b) with toluene-4-thiosulfonic acid S-(2-tert-butyl-4-hydroxymethyl-5-methylphenyl ester (2a) followed by treatment of the coupled intermediate with acid in order to remove the BOC protecting group:

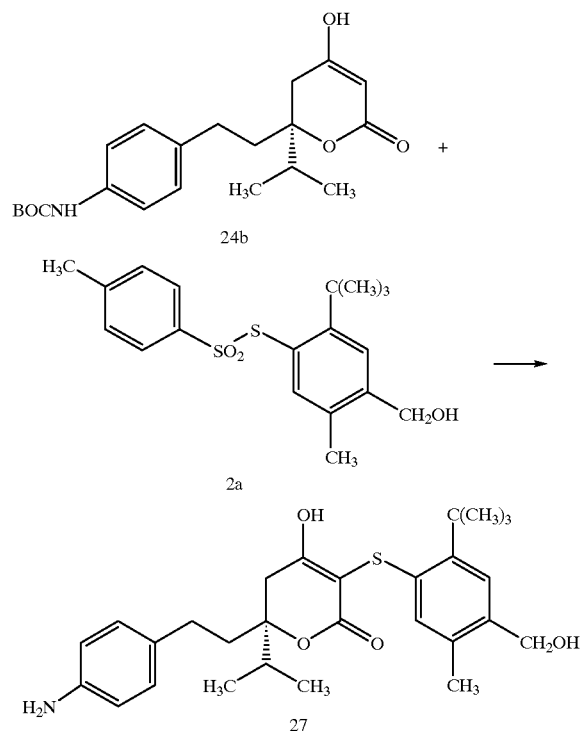

A new, high yield process is described here for the synthesis of (S)-6-[2-(4-amino-phenyl)-ethyl]-3-(2-tert-butyl-4-hydroxymethyl-5-methyl-phenylsulfanyl)-4-hydroxy-6-isopropyl-5,6-dihydro-pyran-2-one which employs nitrogen protecting groups that may be removed in the final step under basic conditions rather than the acidic conditions used in the old method. This coupling method can be used to synthesize the specific dihydropyrone HIV protease inhibitors disclosed herein and others using the appropriate two components. The acidic conditions that are required in the removal of BOC protecting groups cause extensive decomposition of (S)-6-[2-(4-amino-phenyl)-ethyl]-3-(2-tert-butyl-4-hydroxymethyl-5-methyl-phenylsulfanyl)-4-hydroxy-6-isopropyl-5,6-dihydro-pyran-2-one. In this new process, the base labile nitrogen protecting groups that may be used to protect the nitrogen function in intermediate 24b include: acetyl, formyl, propionyl, benzoyl, methyl carbamoyl, ethyl carbamoyl, benzyl carbamoyl and related nitrogen protecting groups. A second aspect of this process entails the use of improved reaction conditions for the coupling step used to prepare the N-protected of 6-[2-(4-amino-phenyl)-ethyl]-3-(2-tert-butyl-4-hydroxymethyl-5-methyl-phenylsulfanyl)-4-hydroxy-6-isopropyl-5,6-dihydro-pyran-2-one derivatives, 27a. These reaction conditions involve the use of a tertiary amine base in a low boiling, polar, aprotic solvent. These conditions allow the coupling step to proceed in high yield with the formation of the 27a coupled intermediate in high purity.

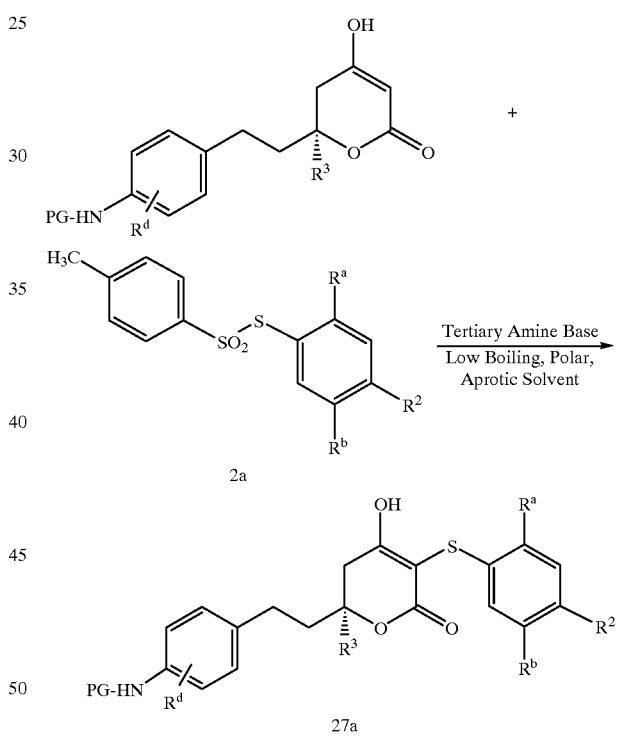

$R^d$ is hydrogen, halogen, or $C_1$–$C_6$ alkyl, $R^a$ and $R^b$ are independently $C_1$–$C_6$ alkyl, $R^2$ is —$NH_2$ or —$CH_2OH$, and PG is as defined above.

In the second part of this process, intermediate 27a is allowed to react with a suitable base such as sodium or potassium hydroxide, sodium methoxide, aqueous ammonia or a related base in order to remove the nitrogen protecting group and form (S)-6-[2-(4-amino-phenyl)-ethyl]-3-(2-tert-butyl-4-hydroxymethyl-5-methyl-phenylsulfanyl)-4-hydroxy-6-isopropyl-5,6-dihydro-pyran-2-one in high yield.

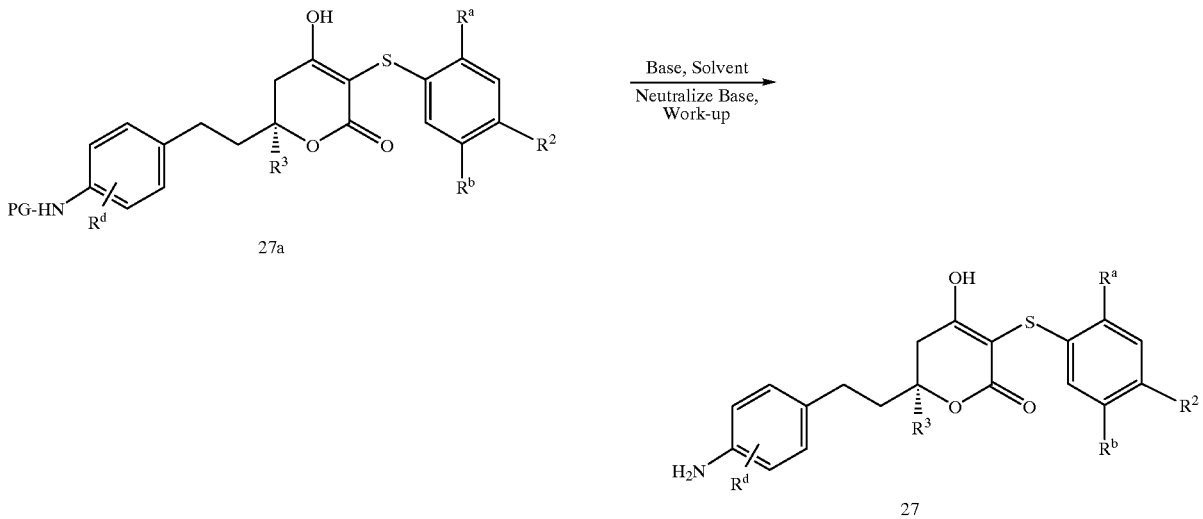

General Description of the Process (S)-6-[2-(4-Amino-phenyl)-ethyl]-3-(2-tert-butyl-4-hydroxymethyl-5-methyl-phenylsulfanyl)-4-hydroxy-6-isopropyl-5,6-dihydro-pyran-2-one is prepared using two procedures beginning with two key starting materials, namely the toluene4-thiosulfonic acid S-(2-tert-butyl-4-hydroxymethyl-5-methylphenyl) ester (2a) and a suitable N-protected (S)-6-[2-(4-aminophenyl)ethyl]-4-hydroxy-6-isopropyl-5,6-dihydropyran-2-one derivative (24).

In Procedure I, the toluene-4-thiosulfonic acid S-(2-tert-butyl-4-hydroxymethyl-5-methylphenyl) ester (2a) is allowed to react with the N-protected (S)-6-[2-(4-aminophenyl)ethyl]-4-hydroxy-6-isopropyl-5,6-dihydropyran-2-one derivative (24) in the presence of a suitable tertiary amine base such as triethylamine in a suitable polar, low boiling, aprotic solvent such as acetonitrile or THF. Work-up involving (1) extraction with a suitable nonpolar solvent such as heptane or heptane-ethyl acetate to remove organic impurities, (2) extraction with a suitable base such as aqueous sodium bicarbonate to remove the toluenesulfinic acid by-product and (3) extraction with a suitable buffered, nonnucleophilic acid such as aqueous sodium dihydrogen phosphate to remove the tertiary amine base followed by isolation involving crystallization of the product from a suitable solvent system provides the desired N-protected (S6-[2-(4-aminophenyl)ethyl]-3-(2-tert-butyl-4-hydroxymethyl-5-methylphenylsulfanyl)-4-hydroxy-6-isopropyl-5,6-dihydropyran-2-one derivative (27a).

In Procedure II, the N-protected (S)-6-[2-(4-aminophenyl)ethyl]-3-(2-tert-butyl-4-hydroxymethyl-5-methylphenylsulfanyl)-4-hydroxy-6-isopropyl-5,6-dihydropyran-2-one derivative (27a) is allowed to react with a suitable base such as sodium hydroxide, potassium hydroxide, ammonia, sodium methoxide etc. in a suitable solvent such as ethanol, aqueous ethanol, methanol, or tetrahydrofuran followed, after completion of the deprotection reaction, by neutralization of the base with a suitable nonnucleophilic acid such as acetic acid and finally isolation of the product by crystallization from a suitable solvent to give the desired (S)-6-[2-(4-aminophenyl)-ethyl]-3-(2-tert-butyl-4-hydroxymethyl-5-methylphenylsulfanyl)-4-hydroxy-6-isopropyl-5,6-dihydropyran-2-one (27).

SPECIFIC EXAMPLES

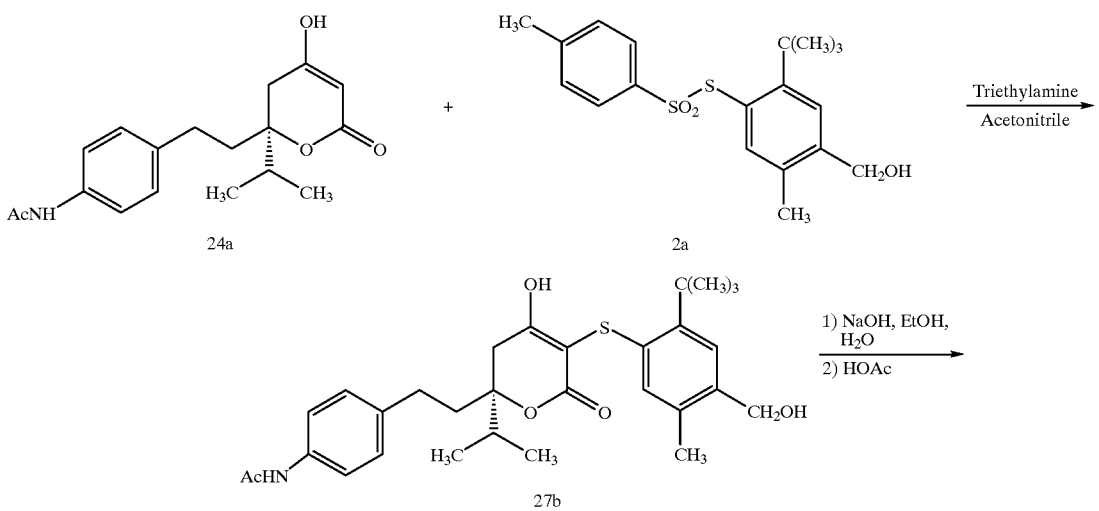

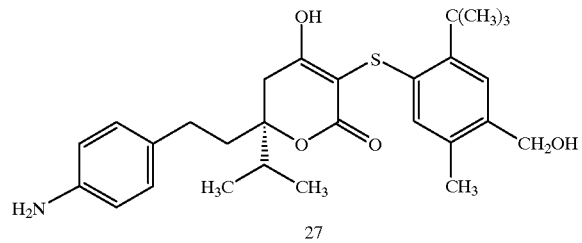

Procedure I: (S)-N-(4-{2-[5-(2-tert-Butyl-4-hydroxymethyl-5-methylphenylsulfanyl)-4-hydroxy-2-isopropyl-6-oxo-3,6-dihydro-2H-pyran-2-yl]ethyl}phenyl)acetamide (27b)

(S)-6-[2-(4-Acetylaminophenyl)ethyl]-4-hydroxy-6-isopropyl-5,6-dihydropyan-2-one (24a) (7.12 Kg, 20.4 mol adjusting for HPLC purity of 95.4%/ and a water content of 4.7%), toluene-4-thiosulfonic acid S-(2-tert-butyl-4-hydroxymethyl-5-methylphenyl) ester (2a) (7.77 Kg, 21.3 mol), acetonitrile (19 L) and triethylamine (4.7 Kg, 46.5 mol) were added to a reactor under an inert atmosphere and the mixture stirred at 22–26° C. for 24 hours. A solution of sodium bicarbonate (2.5 Kg) in water (35 L) followed by ethyl acetate (18 L) and heptane (19 L) were added to the reactor. After agitation the three layers were allowed to settle and the lower aqueous layer separated and retained. The upper solvent layer was separated (and discarded) from the remaining, middle product layer. The latter was extracted with a solution of sodium bicarbonate (2.6 Kg) in water (31 L) and this aqueous extract combined with the first aqueous sodium bicarbonate extract. The remaining product layer was extracted with a solution of heptane (5 L) in ethyl acetate (12 L) and the heptane-ethyl acetate extract discarded. The combined aqueous bicarbonate extracts were extracted with a solution of ethyl acetate (17 L) in tetrahydrofuran (39 L). The aqueous bicarbonate extracts were then discarded and the ethyl acetate-THF extract combined with the product layer. The latter solution was then extracted initially with a solution of potassium dihydrogen phosphate (5.1 Kg) in water (35 L) followed by three extractions using in each case a solution of potassium dihydrogen phosphate (8.5 Kg) in hot water (35 L). All of the aqueous potassium dihydrogen phosphate extracts were discarded and the remaining organic product layer dried over anhydrous magnesium sulfate. The salt was separated by filtration and the salt washed with tetrahydrofuran (60 L). The filtrate and tetrahydrofuran wash were combined and concentrated under vacuum to remove solvent while maintaining the batch temperature below 48° C. The warm residue was treated with ethyl alcohol (2 L) and ethyl acetate (6 L) and the resulting mixture stirred at 40–9° C. while 95 L ethyl acetate was added slowly over 3 hours to precipitate the product. The mixture was stirred and cooled to 0° C. and filtered and the solid washed with ethyl acetate (2×30 L) and vacuum dried overnight at 45° C. until the LOD was less than 0.5%. This provided 9.1 g (82% yield, 17 mol correcting for HPLC purity) of (S)-N-(4-{2-[5-(2-tert-butyl-4-hydroxymethyl-5-methylphenylsulfanyl)-4-hydroxy-2-isopropyl-6-oxo-3,6-dihydro-2H-pyran-2-yl]ethyl}phenyl) acetamide (27b): mp: 185° C. (dec.); Assay (HPLC): 96.8 area %; LOD: 0.20 w/w %.

Procedure II: (S)-6-[2-(4-Aminophenyl)ethyl]-3-(2-tert-butyl-4-hydroxymethyl-5-methylphenylsulfanyl)-4-hydroxy-6-isopropyl-5,6-dihydropyran-2-one (27)

(S)-N-(4-{2-[5-(2-tert-Butyl-4-hydroxymethyl-5-methylphenylsulfanyl)-4-hydroxy-2-isopropyl-6-oxo-3,6-dihydro-2H-pyran-2-yl]ethyl}phenyl)acetamide (27b) (8.90 Kg, 16.4 mol correcting for HPLC purity of 96.8%), water (43 L) and cold ethyl alcohol (76 L) were added to a reactor under an inert atmosphere. Sodium hydroxide, 50% aqueous solution (31 Kg) and water (27 L) were added and the vessel sealed. The mixture was stirred and heated to 108° C. Stirring was continued at 108–112° C. for 2.5 hours. The mixture was cooled to 65° C. and the pH adjusted to 6.9 by addition of 23.7 Kg glacial acetic acid over 40 minutes while maintaining the batch temperature between 65 and 69° C. The solution was transferred to a second reactor containing 3 Kg ADP carbon. The first reactor was rinsed with ethyl alcohol (5 L) and the rinse transferred to the second reactor. The resulting mixture was stirred at 65–67° C. for 15 minutes and then filtered with the aid of Supercel Hyflo (5 Kg) into a still. The second reactor and the filter were rinsed with a solution of water (5 L) in ethyl alcohol (25 L) and the rinse combined with the product solution in the still which was then concentrated under vacuum at 40–46° C. to remove 18–20 L solvent. Seed crystals were added to the remaining solution in the still and the mixture stirred and cooled to 0° C. and filtered. The product was washed with water (40 L) and vacuum dried overnight at 61° C. to give (S)-6-[2-(4-aminophenyl)-ethyl]-3-(2-tert-butyl-4-hydroxymethyl-5-methylphenylsulfanyl)-4-hydroxy-6-isopropyl-5,6-dihydropyran-2-one (27) (7.00 Kg, 13.4 mol, 82% yield correcting for HPLC purity, ethanol and water content): mp: 140° C. (dec); Assay (HPLC): 99.2 area%; Chiral assay (HPLC): 99.7 area % (S) isomer; Ethanol (GC): 6.7 w/w %; Water (KF): 0.32 w/w %. This material is suitable for use in the preparation of pharmaceutically acceptable salts.

Synthesis of Toluene4-thiosulfonic acid S-(4-amino-2-tert-butyl-5-methylphenyl)ester hydrochloride

A Process for the Preparation of S-arylsulfonyl and S-alkylsulfonyl derivatives of 4-Amino-2-tert-butyl-5-methylthiophenol S-Arylsulfonyl and S-alkylsulfonyl derivatives (29) of 2-tert-butyl-4-mercapto-5-methylphenylamine are key intermediates required for the synthesis of 3-(4-amino-2-tert-butyl-5-methyl-phenylsulfanyl)-4-hydroxy-6-[2-(4-hydroxy-phenyl)-ethyl]-6-isopropyl-5,6-dihydro-pyran-2-one and related dihydropyrone HIV protease inhibitors. In this process the arysulfonyl group or alkylsulfonyl group is displaced as a leaving group in a coupling reaction of 29 with the nucleophilic center at the 3 position of the pyrone ring associated with a suitably substituted intermediate such as 28.

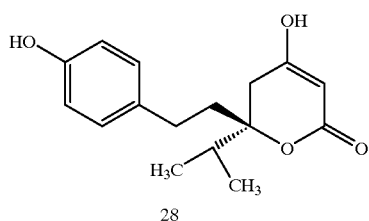

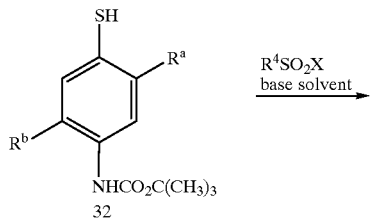

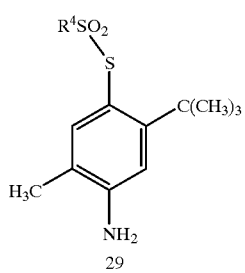

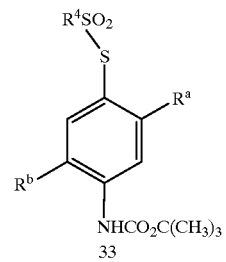

$R^a$ and $R^b$ are independently $C_1$–$C_6$ alkyl, $R^4$ is as defined above.

Procedure III:

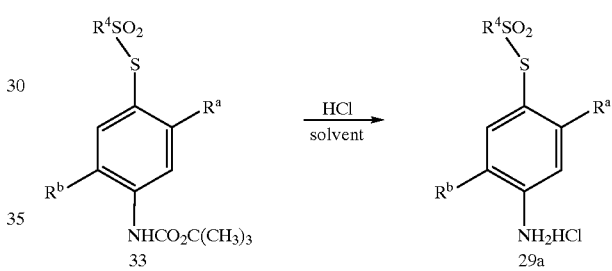

A new, high yield process is proposed here for the synthesis of 2-tert-butyl-4-mercapto-5-methylphenylamine and its S-arylsulfonyl and S-alkylsulfonyl derivatives beginning with 5-tert-butyl-2-methyl-4-thiocyanatophenylamine (30). Three procedures involving a total of 4 steps are required to convert 5-tert-butyl-2-methyl4-thiocyanatophenylamine (30) into (29) which is isolated as its hydrochloride salt (29a).

General Description of the Process

Procedure I:

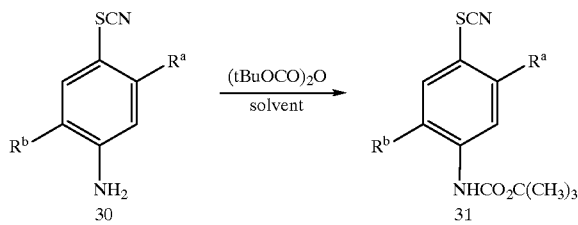

Procedure II:

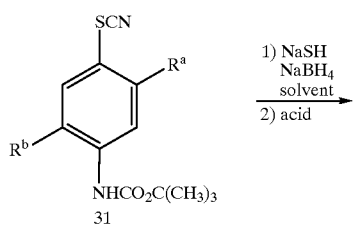

Procedure I: (30) is treated with di-tert-butyl dicarbonate in a suitable nonpolar, aprotic solvent such as heptane and the mixture heated until the reaction is complete. The product is isolated by cooling and filtration to give (31).

Procedure II: (31) is allowed to react with a mixture of sodium hydrogen sulfide and sodium borohydride in a suitable solvent system such as methanol or methanol-water or methanol-THF-water to form the sodium salt of (32). The product mixture is acidified with a suitable acid such as acetic acid and following work-up to remove salts, the desired intermediate, (32) is isolated. The latter is treated with a suitable base such as pyridine in a suitable aprotic solvent such as toluene and the resulting solution added to a suitable sulfonating agent such as toluenesulfonyl chloride, toluenesulfonyl bromide, or methanesulfonyl chloride. Work-up of the product mixture to remove salts followed by isolation of the product provides the desired S substituted aryl- or alkanesulfonyl derivatives (33) of(32).

Procedure III: The S substituted aryl- or alkanesulfonyl derivative (33) is dissolved in a suitable solvent such as ether or methylene chloride and the solution treated with a suitable acid such as hydrogen chloride in order to remove the BOC protecting group. Work-up and isolation of the reaction mixture provides the desired S substituted arylsulfonyl or alkanesulfonyl derivatives (29a), which are usually isolated as a suitable amine salt such as the hydrochloride salt.

SPECIFIC EXAMPLES

Procedure I:

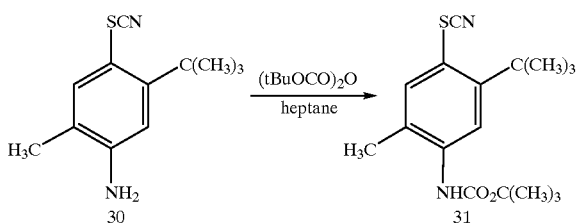

Procedure II:

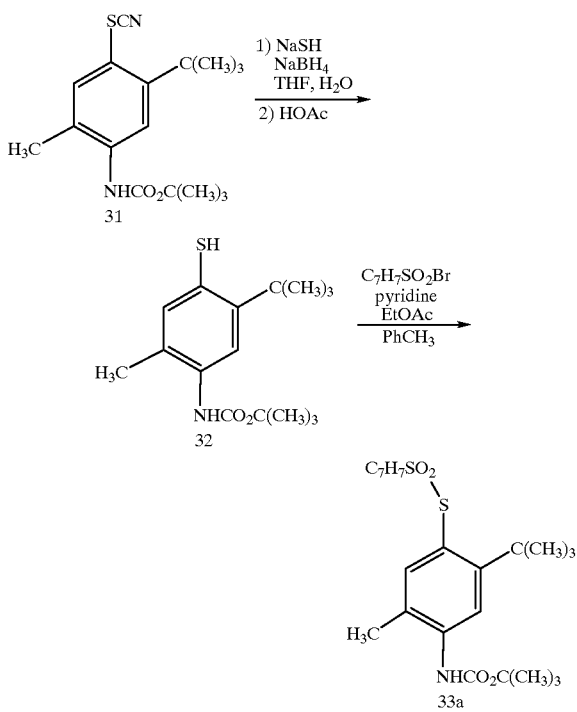

Procedure III:

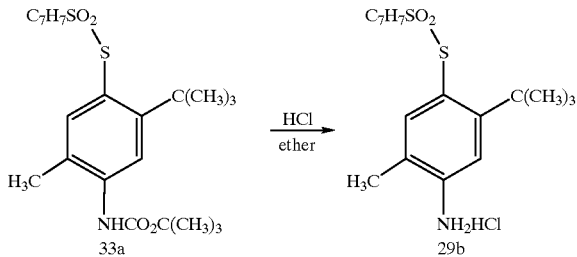

Procedure I: N-(5-tert-Butyl-2-methyl-4-thiocyanatophenyl)carbamic Acid tert-Butyl Ester (31)

Heptane (275 mL) was added to 5-tert-butyl-2-methyl-4-thiocyanatophenylamine (30) (52.3 g, 237 mmol) and di-tert-butyl dicarbonate (62.2 g). The mixture was stirred overnight at 90° C. The mixture was allowed to cool to 30° C. and a small amount of N-(5-tert-butyl-2-methyl-4-thiocyanatophenyl)carbamic acid tert-butyl ester seed crystals added. The mixture was stirred and cooled to 0–5° C. where it was held for 1 hour. The mixture was filtered and the solid washed with heptane (2×25 mL) and vacuum dried at 50° C. to give N-(5-tert-butyl-2-methyl-4-thiocyanatophenyl)carbamic acid tert-butyl ester (31) (68.8 g, 215 mmol, 90% yield): mp: 100–111° C.; Assay (HPLC): 100.0 area %.

Procedure II: Toluene-4-thiosulfonic Acid S-(4-tert-Butoxycarbonylamino-2-tert-butyl-5-methylphenyl) Ester (33a)

N-(5-tert-Butyl-2-methyl-4-thiocyanatophenyl)carbamic acid tert-butyl ester (31) (114 g, 356 mmol) was treated with sodium hydrosulfide hydrate (57.5 g), sodium borohydride (76.8 g), and tetrahydrofuran (1.24 L) under a nitrogen atmosphere. The mixture was stirred and cooled to 0–5° C. and a solution of water (180 mL) and methyl alcohol (300 g) added dropwise over 75 minutes at 5–10° C. The mixture was stirred at 5–15° C. for 5 hours and then at 15–25° C. for 10 hours. Water (1.25 L) and toluene (1.25 L) were added and the mixture stirred and cooled to 5° C. Glacial acetic acid (250 mL) was added slowly at 5–10° C. over 1.5 hours (caution! foaming with hydrogen gas evolution). The organic phase was separated and the aqueous phase discarded. The organic layer was washed with water (2×1.2 L) and then concentrated under vacuum to give N-(5-tert-butyl-4-mercapto-2-methylphenyl)carbamic acid tert-butyl ester (32) which was used without further purification in the next step. The N-(5-tert-butyl-4-mercapto-2-methylphenyl)carbamic acid tert-butyl ester (32) was dissolved in toluene (500 mL) and pyridine (32.0 g) added. The resulting solution was added dropwise over 3 hours and 45 minutes to a cold (8–13° C.) solution of p-toluenesulfonyl bromide (95.3 g) in ethyl acetate (750 mL). The resulting mixture was agitated at 10–15° C. for 3 hours. Water (800 mL) was added to the mixture and the organic phase separated and washed with 1N hydrochloric acid (2×500 mL) and then with water (500 mL). The organic layer was concentrated under vacuum to give 188 g crude toluene-4-thiosulfonic acid S-(4-tert-butoxycarbonylamino-2-tert-butyl-5-methylphenyl). This was treated with heptane (440 mL) and toluene (25 mL) and the resulting solution treated with S-(4-tert-butoxycarbonylamino-2-tert-butyl-5-methyl-phenyl) ester seed crystals. The mixture was stirred and cooled overnight to −5° C. The mixture was filtered and the product washed with cold heptane (2×125 mL) and vacuum dried at 40° C. to give 136 g (302 mmol, 85% yield) toluene-4-thiosulfonic acid S-(4-tert-butoxycarbonylamino-2-tert-butyl-5-methyl-phenyl) ester (33a): mp: 106–108° C.; Assay (HPLC): 99.2 area %.

Procedure III: Toluene-4-thiosulfonic Acid S-(4-Amino-2-tert-butyl-5-methyl-phenyl) Ester Hydrochloride (29b)

Toluene-4-thiosulfonic acid S-(4-tert-butoxycarbonylamino-2-tert-butyl-5-methylphenyl) ester (33a) (70.0 grams, 156 mmol) was dissolved in ethyl ether (500 mL). Anhydrous hydrogen chloride gas was bubbled through the solution while maintaining the temperature between 12 and 17° C. A precipitate formed after about 1 hour. The hydrogen chloride gas treatment was continued for an additional 3 hours at 17–25° C. The resulting mixture was allowed to stir overnight at room temperature and filtered and the product washed with ethyl ether (1.2) and vacuum dried at 40° C. to give 59 g (0.15 mmol, 96% yield) toluene-4-thiosulfonic acid S-(4-amino-2-tert-butyl-5-methylphenyl) ester hydrochloride (29b): mp: 169° C. (dec); Assay (HPLC): 99.8 area %.

What is claimed is:
1. The compound dimethylthiocarbamic acid O-(2-tert-butyl-4-formyl-5-methylphenyl) ester.

2. The compound dimethylthiocarbamic acid S-(2-tert-butyl-4-formyl-5-methylphenyl) ester.

3. The compound dimethylthiocarbanic acid S-(2-tert-butyl-4-hydroxymethyl-5-methylphenyl) ester.

4. A method of making

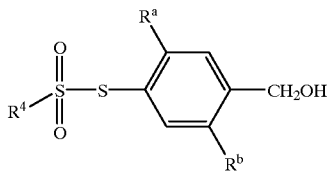

wherein $R^4$ is tolyl, phenyl, or methyl, and $R^a$ and $R^b$ are independently $C_1$–$C_6$ alkyl, the method comprising the steps of:

a. reacting

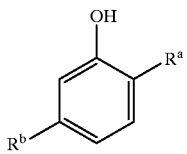

with a Lewis acid catalyst, and tri-$C_1$–$C_6$ alkyl orthoformate or dichloromethyl methyl ether to form

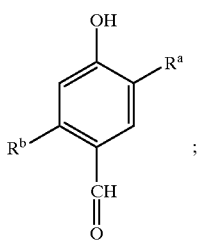

b. reacting

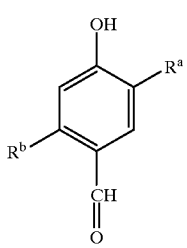 with 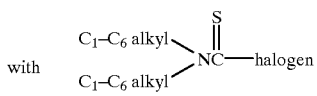

to give

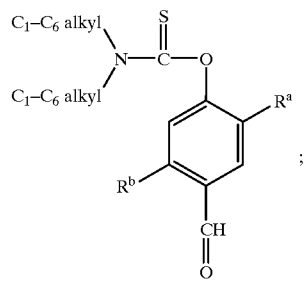

c. heating

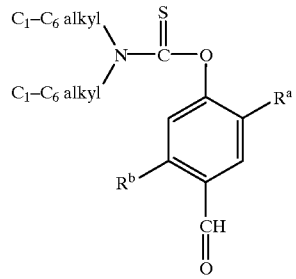

to produce

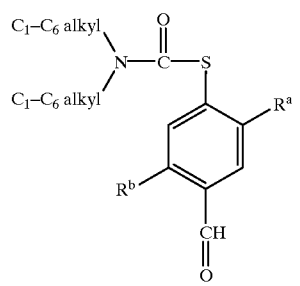

d. reacting

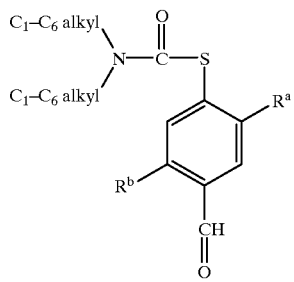

with a reducing agent to give

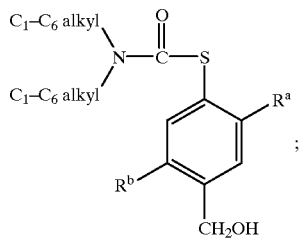

e. heating

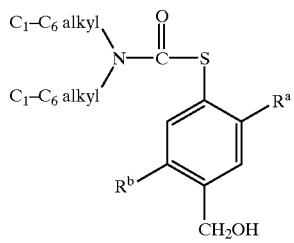

with a base to give

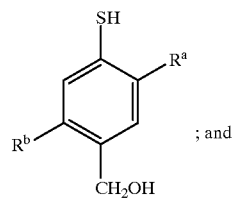

; and f. reacting the

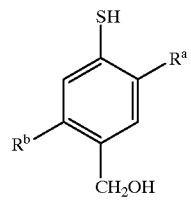

with a sulfonating agent $R^4SO_2$ halogen to give

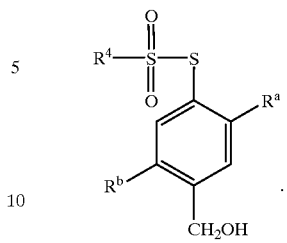

5. The method of claim 4 wherein the reducing agent is sodium borohydride or lithium borohydride.

6. The method of claim 4 wherein the sulfonating agent $R^4SO_2$halogen is toluenesulfonyl chloride, benzenesulfonyl chloride, methanesulfonyl chloride, or toluenesulfonylbromide.

7. The method of claim 4 wherein the Lewis acid catalyst is $AlCl_3$.

8. The method of claim 4 wherein

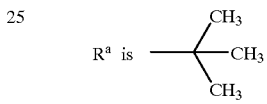

and $R^b$ is —$CH_3$.

9. A method of making

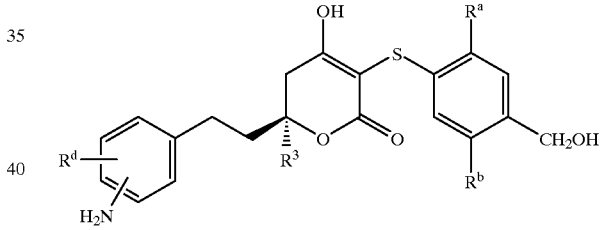

wherein $R^3$ is $C_2$–$C_8$ alkyl or $C_1$–$C_6$ alkyl, $R^a$ and $R^b$ are independently $C_1$–$C_6$ alkyl, and $R^d$ is hydrogen, halogen, or $C_1$–$C_6$ alkyl, the method comprising the steps of:

a. reacting

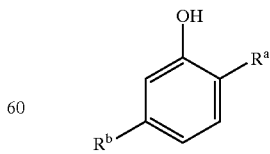

with a Lewis acid catalyst, and tri-$C_1$–$C_6$ alkyl orthoformate or dichloromethyl methyl ether to form

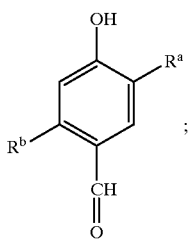
b. reacting
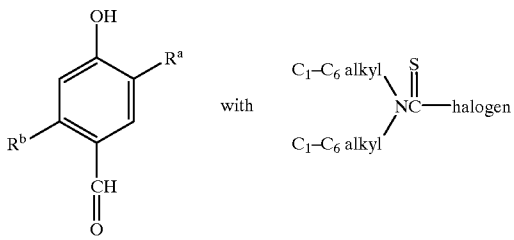
to give
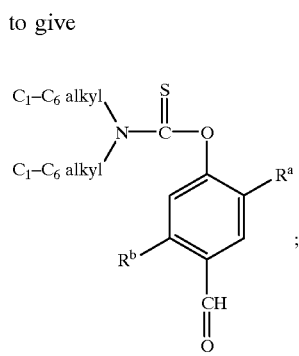
c. heating
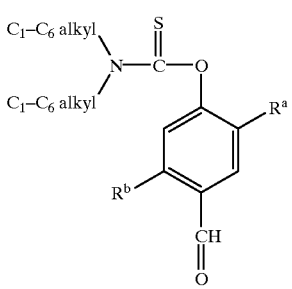
to produce
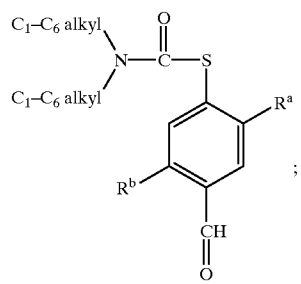
d. reacting
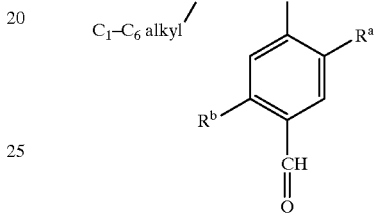
with a reducing agent to give
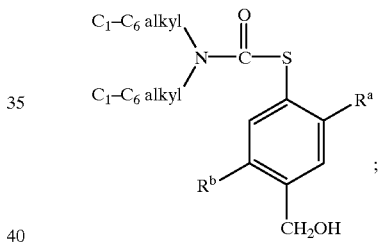
e. heating
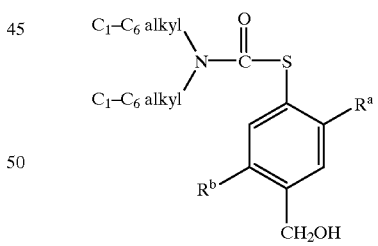
with a base to give
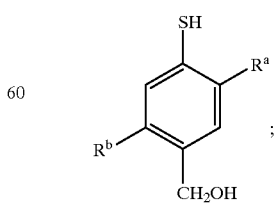

f. reacting the

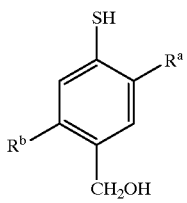

with a sulfonating agent $R^4SO_2$-halogen wherein $R^4$ is tolyl, phenyl, or methyl to give

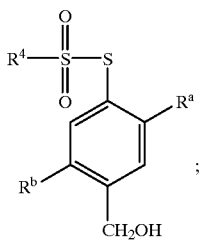

;

g. reaction

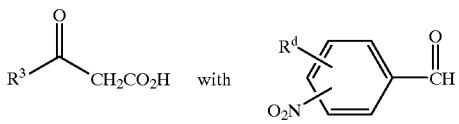

to form

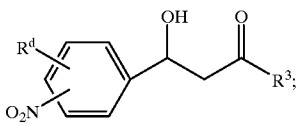

;

h. reacting

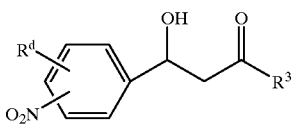

with acetic anhydride to form

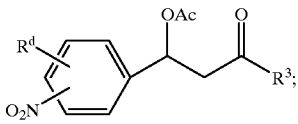

;

i. reacting

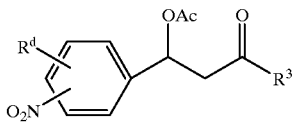

with a base to form

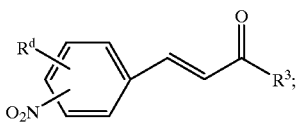

;

j. reacting

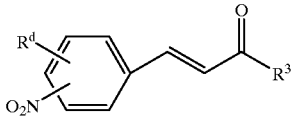

with benzyl acetate or $C_1$–$C_6$ alkyl acetate to form

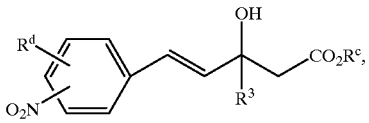

wherein $R^c$ is benzyl or $C_1$–$C_6$ alkyl;

k. reacting

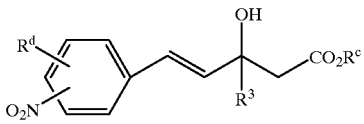

with $H_2$ when $R^c$ is benzyl or $H_2$ followed by aqueous base when $R^c$ is $C_1$–$C_6$ alkyl to give

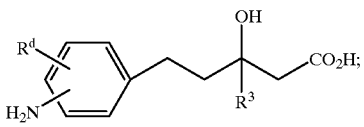

;

l. reacting

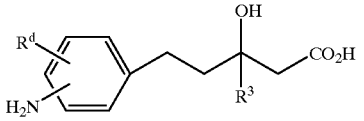

with an acylating agent to form

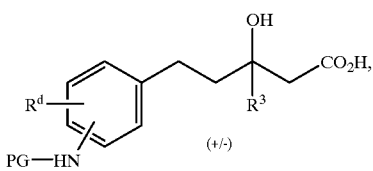

wherein PG is a protecting group selected from acetyl, formnyl, propionyl, benzoyl, methyl carbarnoyl, ethyl carbamoyl, benzyl carbarnoyl, trifluoroacetyl, or isobutyl carbamoyl;

m. treating the

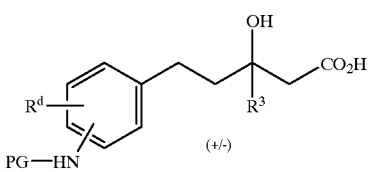

with (S)-N-benzyl-α-methyl benzylamine;

n. allowing crystals to form;
o. collecting the crystals;
p. isolating

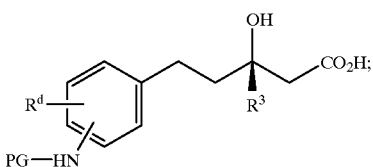

q. reacting

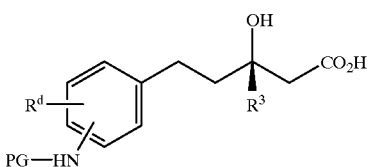

with carbonyl diimidazole to form

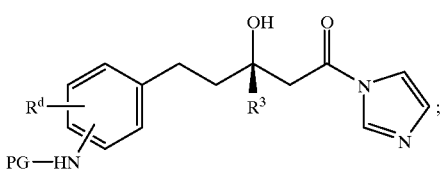

r. reacting the

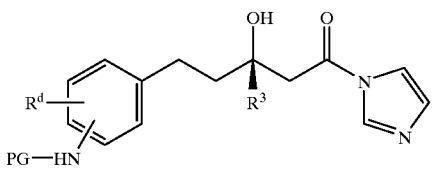

with a compound of the formula

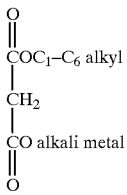

and $MgCl_2$ to form

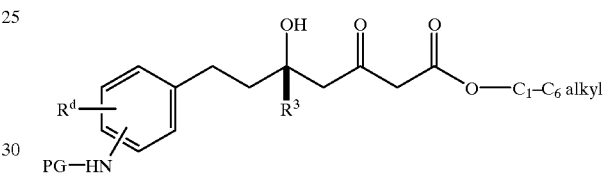

s. reacting the

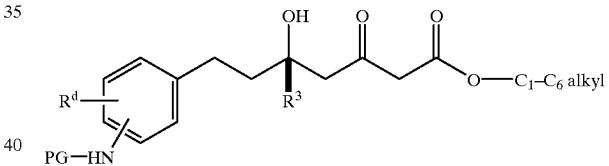

with a base to form

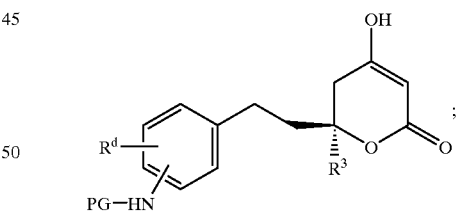

t, reacting

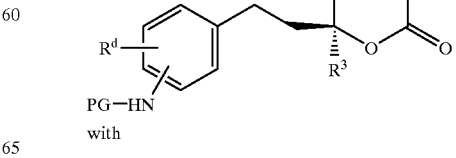

with

-continued

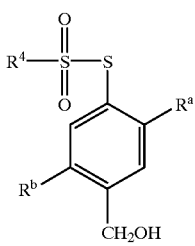

in the presence of a tertiary amine base to give

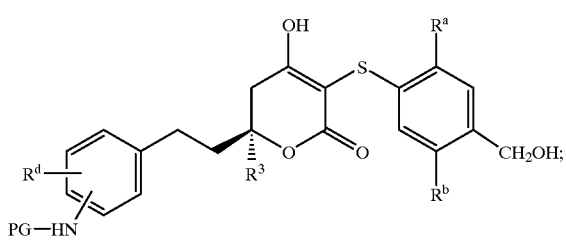

u. reacting

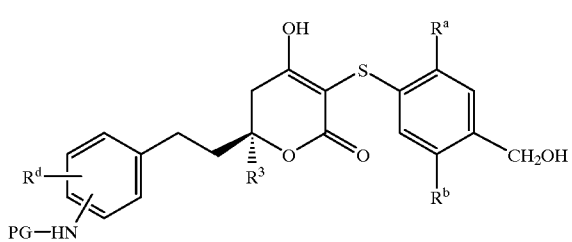

with a base to form

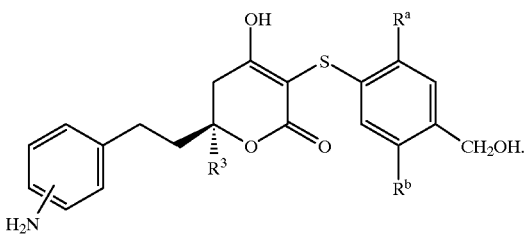

10. The method of claim 9 wherein

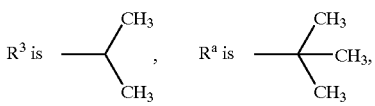

$R^b$ is —$CH_3$, and $R^d$ is hydrogen.

11. The method of claim 9 wherein in Step a the Lewis acid catalyst is $AlCl_3$ and the tri-$C_1$–$C_6$ alkyl orthoformate is triethyl orthoformate.

12. The method of claim 9 wherein in Step b the

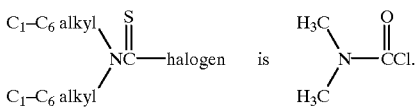

13. The method of claim 9 wherein in Step d the reducing agent is $NaBH_4$.

14. The method of claim 9 wherein in Step e the base is sodium hydroxide.

15. The method of claim 9 wherein in Step f the sulfonating agent $R^4$—$SO_2$-halogen is

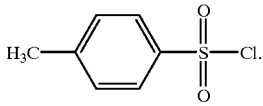

16. The method of claim 9 wherein in Step l the acylating agent is acetic anhydride.

17. The method of claim 9 wherein in Step t the tertiary amine base is triethyl amine.

18. The method of claim 9 wherein in Step u the base is sodium hydroxide.

* * * * *